(12) United States Patent
Goldberg et al.

(10) Patent No.: US 11,000,547 B2
(45) Date of Patent: May 11, 2021

(54) COMPOSITIONS RELATED TO RNA IN CIRCULARIZED FORM

(71) Applicant: Dana-Farber Cancer Institute, Inc., Boston, MA (US)

(72) Inventors: Michael Goldberg, Brookline, MA (US); Ellese Carmona, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1 day.

(21) Appl. No.: 15/579,322

(22) PCT Filed: Jun. 6, 2016

(86) PCT No.: PCT/US2016/036045
§ 371 (c)(1),
(2) Date: Dec. 4, 2017

(87) PCT Pub. No.: WO2016/197121
PCT Pub. Date: Dec. 8, 2016

(65) Prior Publication Data
US 2018/0169146 A1 Jun. 21, 2018

Related U.S. Application Data

(60) Provisional application No. 62/303,116, filed on Mar. 3, 2016, provisional application No. 62/171,538, filed on Jun. 5, 2015.

(51) Int. Cl.
| | | |
|---|---|---|
| *A61K 35/17* | (2015.01) | |
| *C07K 14/435* | (2006.01) | |
| *C12N 15/11* | (2006.01) | |
| *A61P 35/00* | (2006.01) | |
| *A61K 48/00* | (2006.01) | |
| *C07K 14/005* | (2006.01) | |
| *C07K 14/195* | (2006.01) | |
| *C12N 5/0783* | (2010.01) | |

(52) U.S. Cl.
CPC .......... *A61K 35/17* (2013.01); *A61K 48/0075* (2013.01); *A61K 48/0091* (2013.01); *A61P 35/00* (2018.01); *C07K 14/005* (2013.01); *C07K 14/195* (2013.01); *C07K 14/435* (2013.01); *C12N 5/0636* (2013.01); *C12N 15/111* (2013.01); *C12N 2320/51* (2013.01)

(58) Field of Classification Search
CPC . A61K 2039/5156; A61P 35/00; C12N 15/62; C12N 15/63; C12N 15/67
See application file for complete search history.

(56) References Cited

U.S. PATENT DOCUMENTS

| | | |
|---|---|---|
| 5,948,902 A | 9/1999 | Honkanen et al. |
| 7,303,901 B2 | 12/2007 | Hjorleifsdottir et al. |
| 2008/0131899 A1 | 6/2008 | Landegren et al. |
| 2016/0083747 A1* | 3/2016 | Kruse ................. C12N 15/115 514/44 R |
| 2017/0204422 A1* | 7/2017 | Nelson .................. C07H 21/02 |

FOREIGN PATENT DOCUMENTS

| | | |
|---|---|---|
| WO | WO 2010/084371 A1 | 7/2010 |
| WO | WO 2016/197121 A1 | 12/2016 |

OTHER PUBLICATIONS

International Search Report and Written Opinion for Application No. PCT/US2018/027665 dated Sep. 4, 2018.
International Preliminary Report on Patentability for Application No. PCT/US2016/036045 dated Dec. 14, 2017.
International Search Report and Written Opinion for Application No. PCT/US2016/036045 dated Sep. 27, 2016.
Beaudry et al., An efficient strategy for the synthesis of circular RNA molecules. Nucleic Acids Res. Aug. 11, 1995;23(15):3064-6.
Chen et al., Internal ribosome entry sites tests with circular mRNAs. Methods Mol Biol. 1998;77:355-63.
Ho et al., Bacteriophage T4 RNA ligase 2 (gp24.1) exemplifies a family of RNA ligases found in all phylogenetic domains. Proc. Natl. Acad. Sci. USA Oct. 1, 2002;99(20):12709-14. doi: 10.1073/pnas.192184699.
Moore et al., Site-specific modification of pre-mRNA: the 2'-hydroxyl groups at the splice sites. Science. May 15, 1992;256(5059):992-7.
Puttaraju et al., Group I permuted intron-exon (PIE) sequences self-splice to produce circular exons. Nucleic Acids Res. Oct. 25, 1992;20(20):5357-64.
Rychlik et al., Optimization of the annealing temperature for DNA amplification in vitro. Nucleic Acids Res. Nov. 11, 1990;18(21):6409-12. Erratum in Nucleic Acids Res Feb. 11, 1991;19(3):698.
Wang et al., Oligoribonucleotide circularization by 'template-mediated' ligation with T4 RNA ligase: synthesis of circular hammerhead ribozymes. Nucleic Acids Res. May 15, 1998;26(10):2502-4.
Zecherle et al., Purines are required at the 5' ends of newly initiated RNAs for optional RNA polymerase III gene expression. Mol cell Biol. Oct. 1996;16(10):5801-10.
Chen, C. et al. "Initiation of protein synthesis by the eukaryotic translational apparatus on circular RNAs", Science, 1995, vol. 268, p. 415-417.
Jeck, W. R. et al. "Circular RNAs are abundant, conserved, and associated with ALU repeats", RNA, 2013, vol. 19, No. 2, p. 141-157.
Valdmanis, P. et al. "The Expanding Repertoire of Circular RNAs", Molecular Therapy, 2013, vol. 21, No. 6, p. 1112-1114.
PCT/US2018/027665, Sep. 4, 2018, International Search Report and Written Opinion.
PCT/US2016/036045, Sep. 27, 2016, International Search Report and Written Opinion.
PCT/US2016/036045, Dec. 14, 2017, International Preliminary Report on Patentability.

(Continued)

*Primary Examiner* — Dana H Shin
(74) *Attorney, Agent, or Firm* — Baker Donelson

(57) ABSTRACT

The present invention provides circularized RNA and methods of making and using the same.

30 Claims, 39 Drawing Sheets

Specification includes a Sequence Listing.

(56) References Cited

OTHER PUBLICATIONS

U.S. Appl. No. 16/604,609, filed Oct. 11, 2019, Goldberg et al.
PCT/US2018/027665, Oct. 15, 2019, International Preliminary Report on Patentability.
International Preliminary Report on Patentability for Application No. PCT/US2018/27665, dated Oct. 15, 2019.
Breslauer et al., Predicting DNA duplex stability from the base sequence. Proc Natl Acad Sci. Jun. 1, 1986; 83(11): 3746-50.
Dumousseau et al., Melting, a flexible platform to predict the melting temperatures of nucleic acids. BMC Bioinformatics. Dec. 2012; 13(1): 101.
Freier et al., Improved free-energy parameters for predictions of RNA duplex stability. Proc Natl Acad Sci. Dec. 1, 1986; 83(24): 9373-7.
Kibbe, OligoCalc: an online oligonucleotide properties calculator. Nucleic Acids Res. Jul. 2007; 35 (Web Server Issue):W43-6.

\* cited by examiner

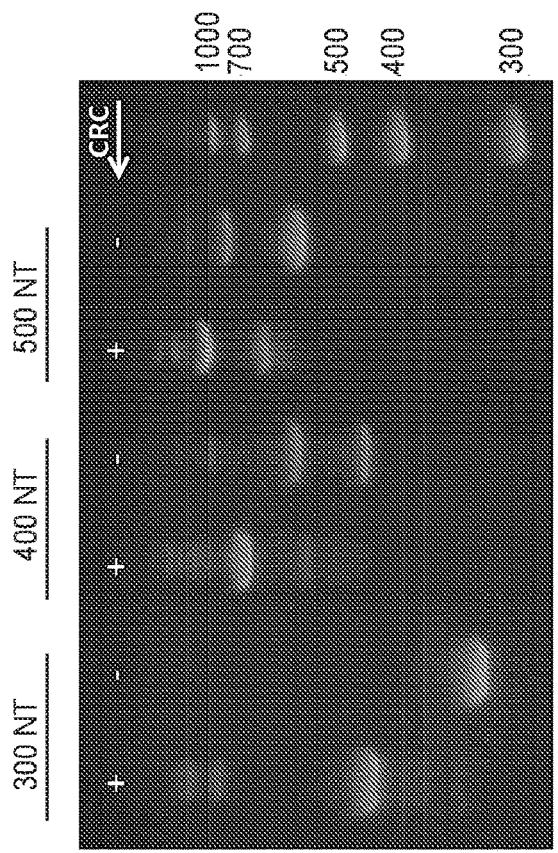
Figure 6A
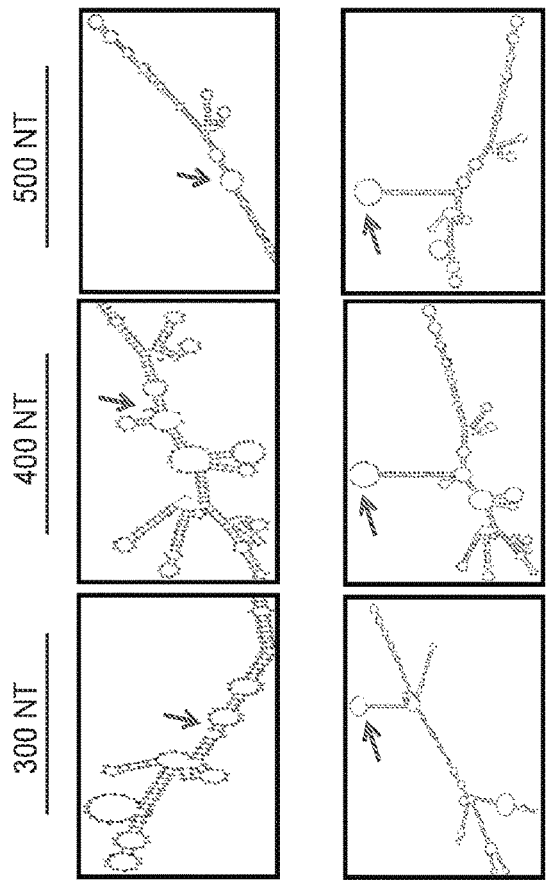
Figure 6B
Figure 6C

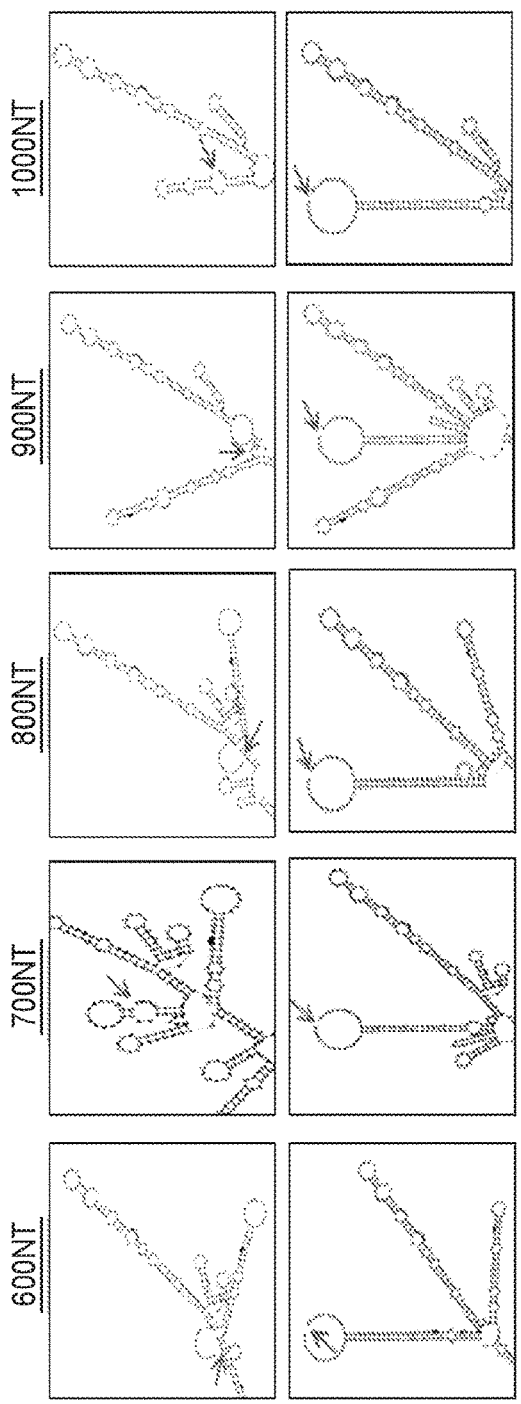
Figure 7A
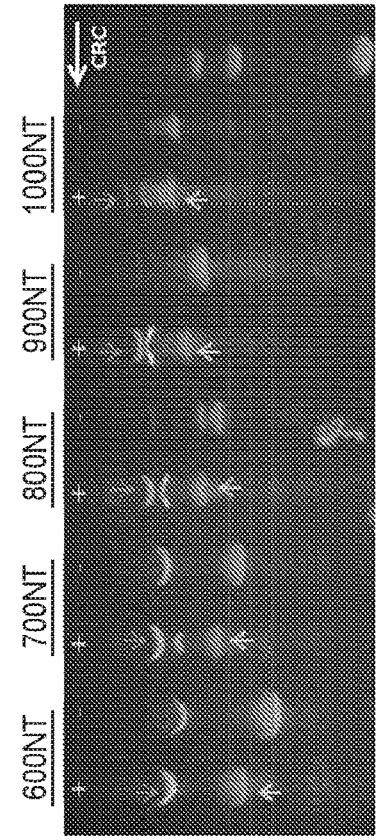
Figure 7B
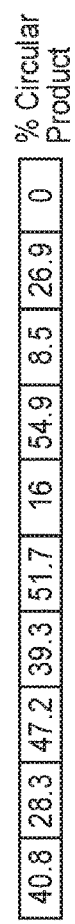
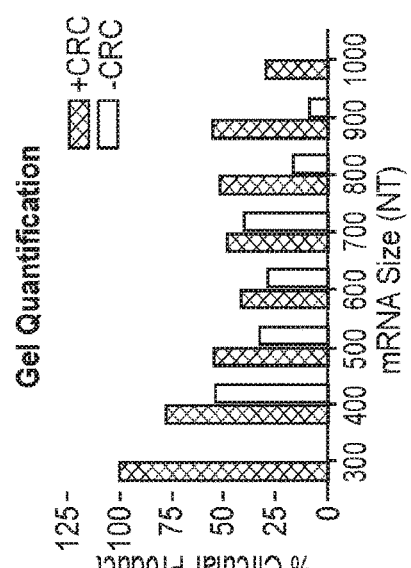
Figure 7D
Figure 7C

Figure 8

| A | B | C | D |
|---|---|---|---|
| Size (NT) | CRC Content | XRN-1 Specificity Control (%) | XRN-1 Efficiency Control (%) | Circularization Efficiency (%) |
| 1000 | Original (30NT) | 97 | 25 | 33 |
| 1000 | Hetero (40NT) | 91 | 16 | 39 |
| 1500 | Original (30NT) | 97 | 26 | 31 |
| 2500 | Original (30NT) | 69 | 30 | 22 |
| 2500 | Hetero (40NT) | 101 | 25 | 22 |
| 3000 | Original (30NT) | 92 | 25 | 30 |
| 3000 | Hetero (40NT) | 77 | 29 | 39 |

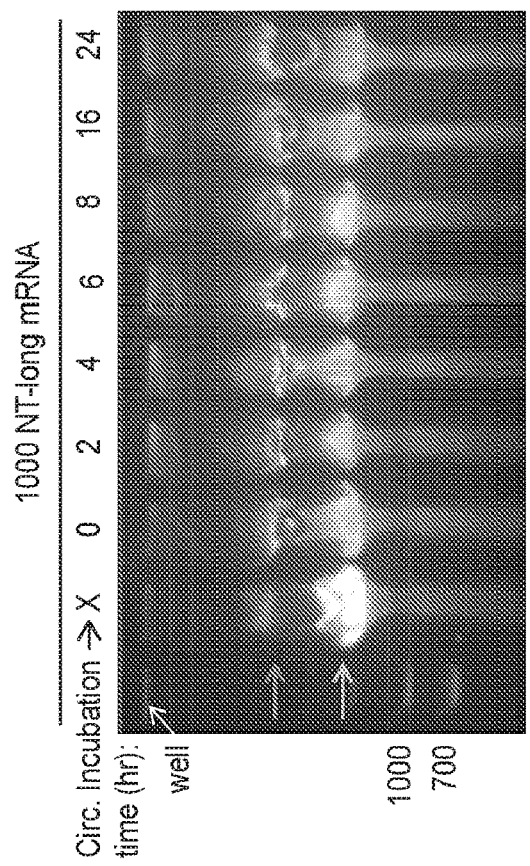
Figure 10C
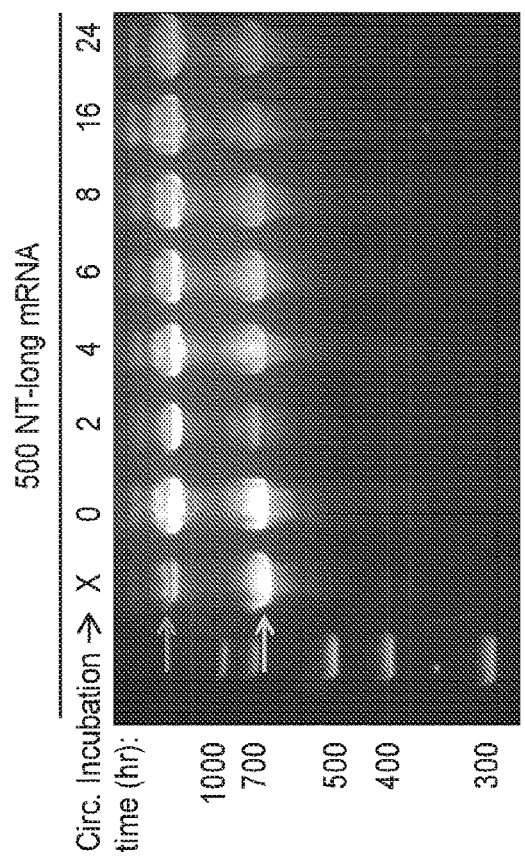
Figure 10A
Figure 10B
| % Circular Product | 33.7 | 51.2 | 67.9 | 54.8 | 55.1 | 60.3 | 68.1 | 62.4 |
|---|---|---|---|---|---|---|---|---|

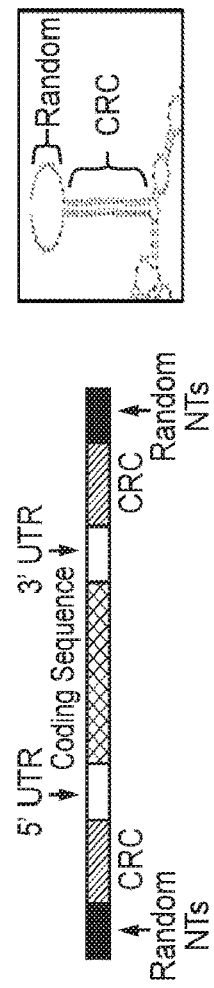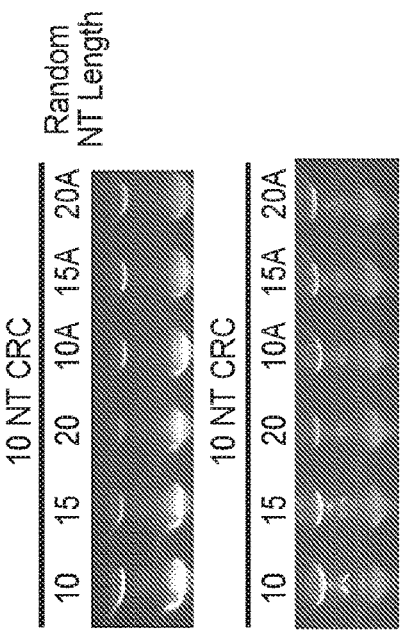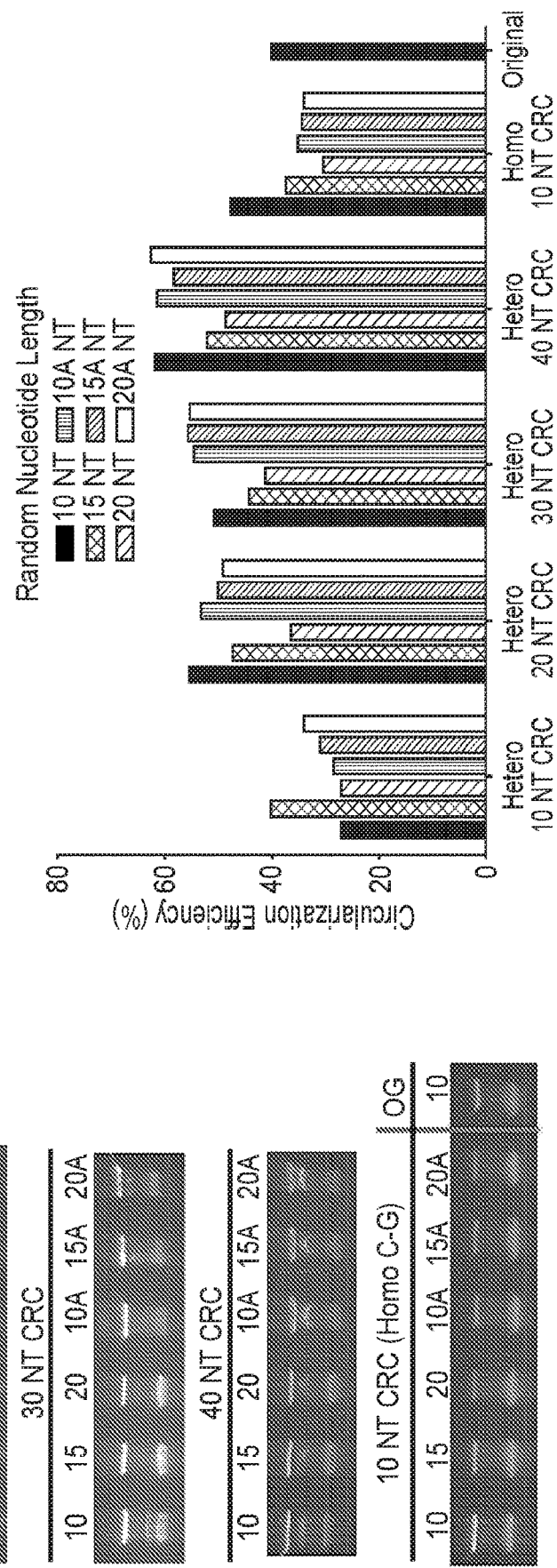
Figure 11A
Figure 11B
Figure 11C

Figure 14
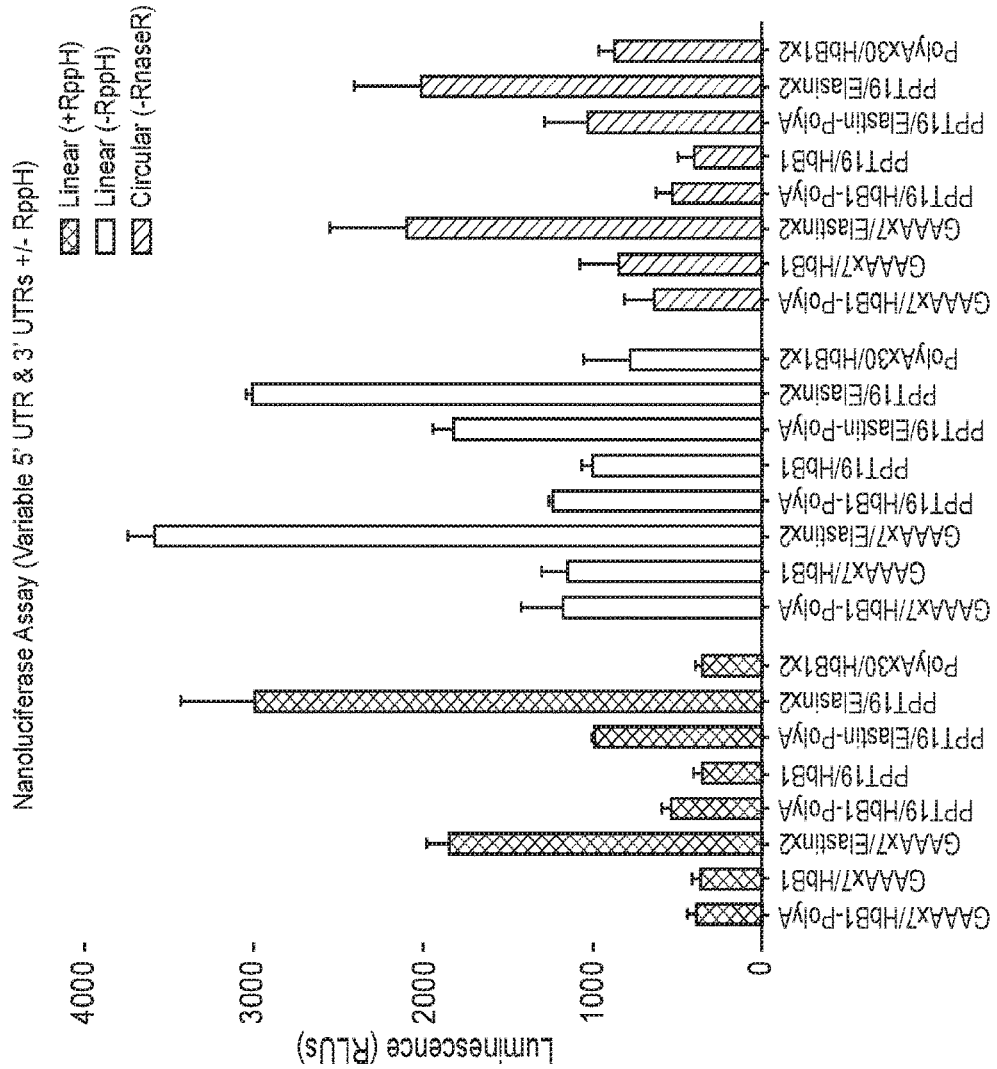
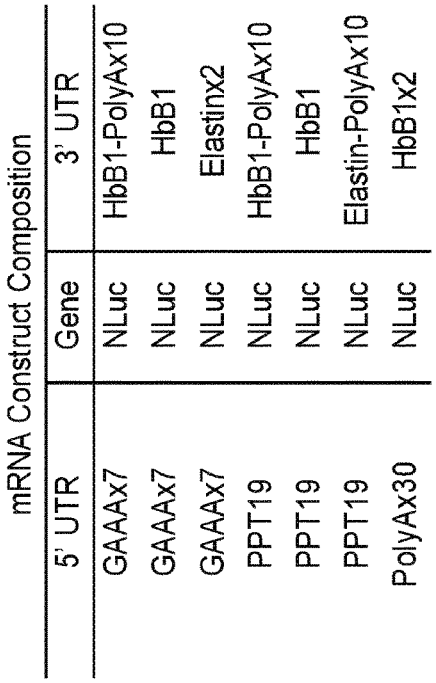

```
                            SEQUENCE LISTING

<160> NUMBER OF SEQ ID NOS: 69

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
tggctgcacg aattgcacaa                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
ttgtgcaatt cgtgcagcca                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
taatacgact cactataggg                                              20

<210> SEQ ID NO 4
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 4
ttatgataac                                                         10

<210> SEQ ID NO 5
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 5
agcgacttcg                                                         10

<210> SEQ ID NO 6
<211> LENGTH: 10
<212> TYPE: DNA
<213> ORGANISM: Artificial Sequence
<220> FEATURE:
<223> OTHER INFORMATION: Synthetic Polynucleotide
```

```
<400> SEQUENCE: 6
aaaagaagga                                                              10

<210> SEQ ID NO 7
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 7
gagggaggga                                                              10

<210> SEQ ID NO 8
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 8
cgaagtcgct tggctgcacg aattgcacaa tccctccctc                             40

<210> SEQ ID NO 9
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 9
taatacgact cactata                                                      17

<210> SEQ ID NO 10
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 10
cccccccccc                                                              10

<210> SEQ ID NO 11
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 11
cccccccccc cccccccccc cccccccccc cccccccccc                             40

<210> SEQ ID NO 12
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 12
gggggggggg                                                              10

<210> SEQ ID NO 13
<211> LENGTH: 40
```

```
<212> TYPE: DNA
<213> ORGANISM: Artificial Sequence
<220> FEATURE:
<223> OTHER INFORMATION: Synthetic Polynucleotide

<400> SEQUENCE: 13
gggggggggg gggggggggg gggggggggg gggggggggg                          40

<210> SEQ ID NO 14
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 14
aaaaaaaaaa                                                           10

<210> SEQ ID NO 15
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 15
aaaaaaaaaa aaaaa                                                     15

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
aaaaaaaaaa aaaaaaaaaa                                                20

<210> SEQ ID NO 17
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 17
accgacggca                                                           10

<210> SEQ ID NO 18
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 18
tgccgtcggt                                                           10

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
```
aacacgttat tgccgtcggt                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
accgacggca ataacgtgtt                                                    20

<210> SEQ ID NO 21
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 21
accgacggca ataacgtgtt ggtacgtaac                                         30

<210> SEQ ID NO 22
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 22
accgacggca ataacgtgtt ggtacgtaac cttcgaacct                              40

<210> SEQ ID NO 23
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 23
aggttcgaag gttacgtacc aacacgttat tgccgtcggt                              40

<210> SEQ ID NO 24
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 24
cggaatatag                                                               10

<210> SEQ ID NO 25
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 25
cggaatatag aagca                                                         15

<210> SEQ ID NO 26
<211> LENGTH: 20
<212> TYPE: DNA
<213> ORGANISM: Artificial Sequence

```
<220> FEATURE:
<223> OTHER INFORMATION: Synthetic Polynucleotide

<400> SEQUENCE: 26
cggaatatag aagcataaga                                                20

<210> SEQ ID NO 27
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 27
gggaaaaaaa                                                           10

<210> SEQ ID NO 28
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 28
gggaaaaaaa aaaaa                                                     15

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
gggaaaaaaa aaaaaaaaaa                                                20

<210> SEQ ID NO 30
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 30
gggaatcgac                                                           10

<210> SEQ ID NO 31
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 31
gggaatcgac tacag                                                     15

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
gggaatcgac tacaggagga                                                20
```

<210> SEQ ID NO 33
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 33
gttacgtacc aacacgttat tgccgtcggt                                    30

<210> SEQ ID NO 34
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 34
ctatattccg aacacgttat tgccgtcggt tccctccctc                          40

<210> SEQ ID NO 35
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 35
ctatattccg aggttcgaag gttacgtacc aacacgttat tgccgtcggt tccctccctc    60

<210> SEQ ID NO 36
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 36
ctatattccg cccccccccc tccctccctc                                    30

<210> SEQ ID NO 37
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 37
ctatattccg cccccccccc cccccccccc cccccccccc cccccccccc tccctccctc    60

<210> SEQ ID NO 38
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 38
ctatattccg gttacgtacc aacacgttat tgccgtcggt tccctccctc              50

<210> SEQ ID NO 39
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 39
ctatattccg tgccgtcggt tccctccctc                                        30

<210> SEQ ID NO 40
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 40
tcttatgctt ctatattccg aacacgttat tgccgtcggt tccctccctc                  50

<210> SEQ ID NO 41
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 41
tcttatgctt ctatattccg aggttcgaag gttacgtacc aacacgttat tgccgtcggt       60
tccctccctc                                                              70

<210> SEQ ID NO 42
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 42
tcttatgctt ctatattccg cccccccccc cccccccccc cccccccccc cccccccccc       60
tccctccctc                                                              70

<210> SEQ ID NO 43
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 43
tcttatgctt ctatattccg cccccccccc tccctccctc                             40

<210> SEQ ID NO 44
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 44
tcttatgctt ctatattccg gttacgtacc aacacgttat tgccgtcggt tccctccctc       60

<210> SEQ ID NO 45
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 45

```
tcttatgctt ctatattccg tgccgtcggt tccctccctc                          40
```

<210> SEQ ID NO 46
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 46

```
tgcttctata ttccgaacac gttattgccg tcggttccct ccctc                    45
```

<210> SEQ ID NO 47
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 47

```
tgcttctata ttccgaggtt cgaaggttac gtaccaacac gttattgccg tcggttccct    60
ccctc                                                                65
```

<210> SEQ ID NO 48
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 48

```
tgcttctata ttccgccccc cccccccccc cccccccccc cccctccct                60 ccctc                                                                65
```

<210> SEQ ID NO 49
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 49

```
tgcttctata ttccgccccc cccctccct ccctc                                35
```

<210> SEQ ID NO 50
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 50

```
tgcttctata ttccggttac gtaccaacac gttattgccg tcggttccct ccctc         55
```

<210> SEQ ID NO 51
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 51

```
tgcttctata ttccgtgccg tcggttccct ccctc                               35
```

```
<210> SEQ ID NO 52
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 52 ttttttttccc aacacgttat tgccgtcggt tccctccctc                              40

<210> SEQ ID NO 53
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 53
tttttttttt aggttcgaag gttacgtacc aacacgttat tgccgtcggt tccctccctc        60

<210> SEQ ID NO 54
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 54
tttttttttt cccccccccc cccccccccc cccccccccc cccccccccc tccctccctc        60

<210> SEQ ID NO 55
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 55
tttttttttt cccccccccc tccctccctc                                         30

<210> SEQ ID NO 56
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 56
tttttttttt gttacgtacc aacacgttat tgccgtcggt tccctccctc                   50

<210> SEQ ID NO 57
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 57
tttttttttt tgccgtcggt tccctccctc                                         30

<210> SEQ ID NO 58
<211> LENGTH: 45
<212> TYPE: DNA
<213> ORGANISM: Artificial Sequence
<220> FEATURE:
<223> OTHER INFORMATION: Synthetic Polynucleotide
```

<400> SEQUENCE: 58
tttttttttt ttcccaacac gttattgccg tcggttccct ccctc                45

<210> SEQ ID NO 59
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 59
tttttttttt tttttaggtt cgaaggttac gtaccaacac gttattgccg tcggttccct   60
ccctc                                                              65

<210> SEQ ID NO 60
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 60
tttttttttt tttttccccc cccccccccc cccccccccc ccccctccct              60
ccctc                                                              65

<210> SEQ ID NO 61
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 61
tttttttttt tttttccccc ccccctccct ccctc                             35

<210> SEQ ID NO 62
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 62
tttttttttt tttttgttac gtaccaacac gttattgccg tcggttccct ccctc       55

<210> SEQ ID NO 63
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 63
tttttttttt tttttgccg tcggttccct ccctc                              35

<210> SEQ ID NO 64
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 64
tttttttttt ttttttccc aacacgttat tgccgtcggt tccctccctc              50

```
<210> SEQ ID NO 65
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 65
tttttttttt tttttttttt aggttcgaag gttacgtacc aacacgttat tgccgtcggt    60
tccctccctc                                                           70

<210> SEQ ID NO 66
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 66
tttttttttt tttttttttt cccccccccc cccccccccc cccccccccc cccccccccc    60
tccctccctc                                                           70

<210> SEQ ID NO 67
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 67
tttttttttt tttttttttt cccccccccc tccctccctc                          40

<210> SEQ ID NO 68
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 68
tttttttttt tttttttttt gttacgtacc aacacgttat tgccgtcggt tccctccctc    60

<210> SEQ ID NO 69
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 69
tttttttttt tttttttttt tgccgtcggt tccctccctc                          40
```

COMPOSITIONS RELATED TO RNA IN CIRCULARIZED FORM

RELATED APPLICATIONS

This application is a national stage entry of PCT application No. PCT/US2016/036045 filed on Jun. 6, 2016, which claims priority to, and the benefit of, U.S. Provisional Application No. 62/171,538, filed Jun. 5, 2015, and U.S. Provisional Application No. 62/303,116, filed Mar. 3, 2016, the contents of each which are incorporated herein by reference in their entirety.

INCORPORATION-BY-REFERENCE OF SEQUENCE LISTING

The contents of the filed named "DFCI-108N01US_ST25.txt", which was created on Dec. 5, 2017, and is 15 KB in size are hereby incorporated by reference in their entirety.

FIELD OF THE INVENTION

The present invention relates generally to compositions of circularized RNA, method of producing, and using same.

BACKGROUND OF THE INVENTION

Circular RNA is useful in the design and production of stable forms of RNA. The circularization of an RNA molecule provides an advantage to the study of RNA structure and function, especially in the case of molecules that are prone to folding in an inactive conformation (Wang and Ruffner, 1998). Circular RNA can also be particularly interesting and useful for in vivo applications, especially in the research area of RNA-based control of gene expression and therapeutics, including protein replacement therapy and vaccination.

Prior to this invention, there were three main techniques for making circularized RNA in vitro: splint-mediated method, permuted intron-exon method, and RNA ligase-mediated method.

However, the existing methodologies are limited by quantities of circularized RNA that can be produced and by the size of RNA that can be circularized, thus limiting their therapeutic application.

It is therefore a primary object of the current invention to provide a general method for preparation of a desired RNA in circularized form that is not limited by quantity or size.

SUMMARY OF THE INVENTION

An aspect of the present invention is a nucleic acid comprising: (a) a 5' complement-reverse complement (CRC) sequence; (b) a 5' untranslated region (UTR) sequence; (c) an RNA sequence; (d) a 3' UTR sequence; and (e) a 3' CRC sequence. The 5' CRC sequence is at least partially complementary to the 3'CRC sequence, e.g., complementary to the 3' CRC sequence.

In embodiments, the RNA sequence may be capable of being translated into a polypeptide, may comprise a RNA that is a reverse complement of an endogenous RNA, e.g., an mRNA, a miRNA, a tRNA, a rRNA, or a lncRNA, or may be capable of binding to an RNA-binding protein (RBP).

In embodiments, the nucleic acid may further comprise at least one random nucleotide sequence comprising between 5 and 25 nucleotides, e.g., 10 to 50 nucleotides, (e.g., 10, 15, or 20 nucleotides).

In embodiments, a 5' random nucleotide sequence may be located at the nucleic acid's 5' end and/or the 3' random nucleotide sequence is located at the nucleic acid's 3' end; the 5' random nucleotide sequence may be located upstream of the 5' CRC sequence and/or the 3' random nucleotide sequence is located downstream of the 3' CRC sequence. The 5' random nucleotide sequence and the 3' random nucleotide sequence may be at least partially complementary. Alternately, the 5' random nucleotide sequence and the 3' random nucleotide sequence may be non-complementary.

In embodiments, the nucleic acid may further comprise at least one 5' and/or 3' polyA sequence comprising between 5 and 25 nucleotides, e.g., 10 to 50 nucleotides (e.g., 10, 20, or 30 nucleotides), and located towards the nucleic acid's 5' end and/or towards the nucleic acid's 3' end. The 5' polyA sequence may be located 5' to the 5' CRC sequence and/or the 3' polyA sequence is located 3' to the 3' CRC sequence.

In embodiments, the 5' and/or the 3' CRC sequence may comprise 10 to 50 nucleotides, e.g., 10, 20, 30, or 40 nucleotides. Preferably, the 5' and/or the 3' CRC sequences comprise 20 nucleotides. The 5' CRC sequence may comprise tggctgcacgaattgcacaa (SEQ ID NO: 1) and the 3' CRC sequence may comprise ttgtgcaattcgtgcagcca (SEQ ID NO 2).

In embodiments, the 5' UTR may be polyAx30, polyAx120, PPT19, PPT19x4, GAAAx7, or polyAx30-EMCV. In embodiments, the 3' UTR may be HbB1-PolyAx10, HbB1, HbB1x2, or a motif from the Elastin 3' UTR, e.g., a 3' UTR comprising the Elastin 3' UTR or a motif thereof, e.g., which is repeated twice or three times. Preferably, the 5' UTR is PPT19 or repeats thereof and the 3' UTR is derived from Elastin or a motif thereof and/or repeats thereof.

In embodiments, the RNA sequence may comprise at least 30 nucleotides, e.g., at least 300 nucleotides (e.g., at least 500 nucleotides). The polypeptide may comprise a tumor-associated antigen, a chimeric antigen receptor, a bacterial or viral antigen, a transposase or a nuclease, a transcription factor, a hormone, an scFv, a Fab, a single-domain antibody (sdAb), or a therapeutic protein. The therapeutic protein may be preproinsulin, hypocretin, human growth hormone, leptin, oxytocin, vasopressin, factor VII, factor VIII, factor IX, erythropoietin, G-CSF, alpha-galactosidase A, iduronidase, N-acetylgalactosamine-4-sulfatase, FSH, DNase, tissue plasminogen activator, glucocerebrosidase, interferon, or IGF-1. The polypeptide may comprise an epitope for presentation by an antigen presenting cell. The polypeptide may lead to improved T-cell priming, as determined by increased production of IFN-γ, including by proliferating cells.

In embodiments, the 5' UTR may comprise an internal ribosome entry site (IRES); preferably, an encephalomyocarditis virus (EMCV) IRES or a PPT19 IRES.

In embodiments, the nucleic acid may comprise a modified nucleotide, e.g., 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, 7-deazaadenosine, 6-azouridine, 6-azocytidine, 6-azothymidine, 5-methyl-2-thiouridine, 2-thiouridine, 4-thiouridine, 2-thiocytidine, dihydrouridine, pseudouridine, queuosine, archaeosine, naphthyl substituted naphthyl groups, an O- and N-alkylated purines and pyrimidines, N6-methyladenosine, 5-methylcarbonylmethyluridine, uridine 5-oxyacetic acid, pyridine-4-one, pyridine-2-one, aminophenol, 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, or alkylcarbonylalkylated nucleotides. Preferably, the modified base is 5-methylcytidine (5mC).

In embodiments, the nucleic acid's 5' and 3' termini are not ligated, such that the nucleic acid is non-circularized.

In embodiments, the nucleic acid's 5' and 3' termini are ligated such that the nucleic acid is circularized. Such a circularized nucleic acid has greater stability (in vitro or in vivo) relative to a non-circularized nucleic acid; such a circularized nucleic acid provides greater polypeptide translation (in vitro or in vivo) relative to a non-circularized nucleic acid.

Another aspect of the present invention is a cell comprising any above-described nucleic acid, e.g., a circularized nucleic acid. A cell comprising an above-described circularized nucleic acid may further comprise a non-circularized nucleic acid having any above-described feature. The cell may be in vitro.

Yet another aspect of the present invention is a non-human mammal comprising an above-described cell, e.g., comprising a circularized nucleic acid or comprising a circularized nucleic acid and a non-circularized nucleic acid.

An aspect of the present invention is a primer comprising (a) a first motif comprising between 5 and 25 random nucleotides; (b) a second motif comprising a complement-reverse complement (CRC) sequence; (c) a third motif comprising an untranslated region (UTR) sequence; and (d) a fourth motif comprising about 20 nucleotides of a RNA sequence. In embodiments, the fourth motif encodes the first 20 nucleotides of the RNA sequence; alternately, the fourth motif encodes the last 20 nucleotides of the RNA sequence. In embodiments, the primer's RNA sequence may be capable of being translated into a polypeptide, may comprise a RNA that is a reverse complement of an endogenous RNA, e.g., an mRNA, a miRNA, a tRNA, an rRNA, or a lncRNA, or may be capable of binding to an RNA-binding protein (RBP).

Another aspect of the present invention is a method for circularizing a nucleic acid comprising: (a) obtaining any above-described nucleic acid and in which the nucleic acid is non-circularized; and (b) ligating the 5' terminus of the nucleic acid to its 3' terminus, thereby producing a circularized nucleic acid. In embodiments, the method may further comprise converting the 5' triphosphate of the nucleic acid into a 5' monophosphate, e.g., by contacting the 5' triphosphate with RNA 5' pyrophosphohydrolase (RppH) or an ATP diphosphohydrolase (apyrase). Alternately, converting the 5' triphosphate of the nucleic acid into a 5' monophosphate may occur by a two-step reaction comprising: (a) contacting the 5' nucleotide of the non-circularized nucleic acid with a phosphatase (e.g., Antarctic Phosphatase, Shrimp Alkaline Phosphatase, or Calf Intestinal Phosphatase) to remove all three phosphates; and (b) contacting the 5' nucleotide after step (a) with a kinase (e.g., Polynucleotide Kinase) that adds a single phosphate. In embodiments, the ligating may occur by contacting the 5' terminus of the nucleic acid and the 3' terminus of the nucleic acid with a ligase, e.g., T4 RNA ligase. The ligating may be repeated at least one additional time, e.g., at least two additional times and at least three additional times. In embodiments, non-circularized nucleic acid molecules may be digested with an RNase, e.g., RNase R, Exonuclease T, λ Exonuclease, Exonuclease I, Exonuclease VII, T7 Exonuclease, or XRN-1; preferably, the RNase is RNase R and/or XRN-1. Non-circularized nucleic acid molecules may be digested with an RNase after the initial ligation or after the ligation is repeated at least one additional time. In embodiments, the obtained nucleic acid is synthesized by in vitro transcription (IVT).

Yet another aspect of the present invention is a circularized nucleic acid produced by an above-described method.

An aspect of the present invention is a composition comprising any above-described circularized nucleic acid. The composition may further comprise a non-circularized nucleic acid having any above-described feature.

Any of the above-described aspects or embodiments can be combined with any other aspect or embodiment as described herein.

Other features and advantages of the invention will be apparent from and encompassed by the Detailed Description, the drawings, and the claims.

BRIEF DESCRIPTION OF THE DRAWINGS

FIGS. 6A to 6C include predicted secondary structures, a gel, and a table showing that inclusion of complement-reverse complement (CRC) motifs enhances efficiency of circularization of RNA constructs 300 to 500 nucleotides (NT) in length.

FIGS. 7A to 7D include predicted secondary structures, a gel, a table, and a graph showing that RNA up to 1000 nucleotide (NT) in length can be circularized when CRC sequences are included in the RNA molecule.

FIG. 8 includes a table showing that inclusion of CRC sequences enhances efficiency of circularization of RNA constructs up to at least 3000 NT in length.

FIGS. 10A to 10C include gels and a table showing that inclusion of CRC sequences results in rapidly produced and robust levels of circularized product.

FIGS. 11A to 11C include a schematic of an RNA molecule and its predicted secondary structure, gels, and a graph showing that circularized RNA constructs containing a longer CRC and shorter Random NT motif confer the highest levels of circularization efficiency.

FIG. 14 includes a graph showing that a 20-mer derived from the elastin 3' UTR motif enhances translation efficiency of linear and circularized RNA.

DETAILED DESCRIPTION OF THE INVENTION

Figure 1:
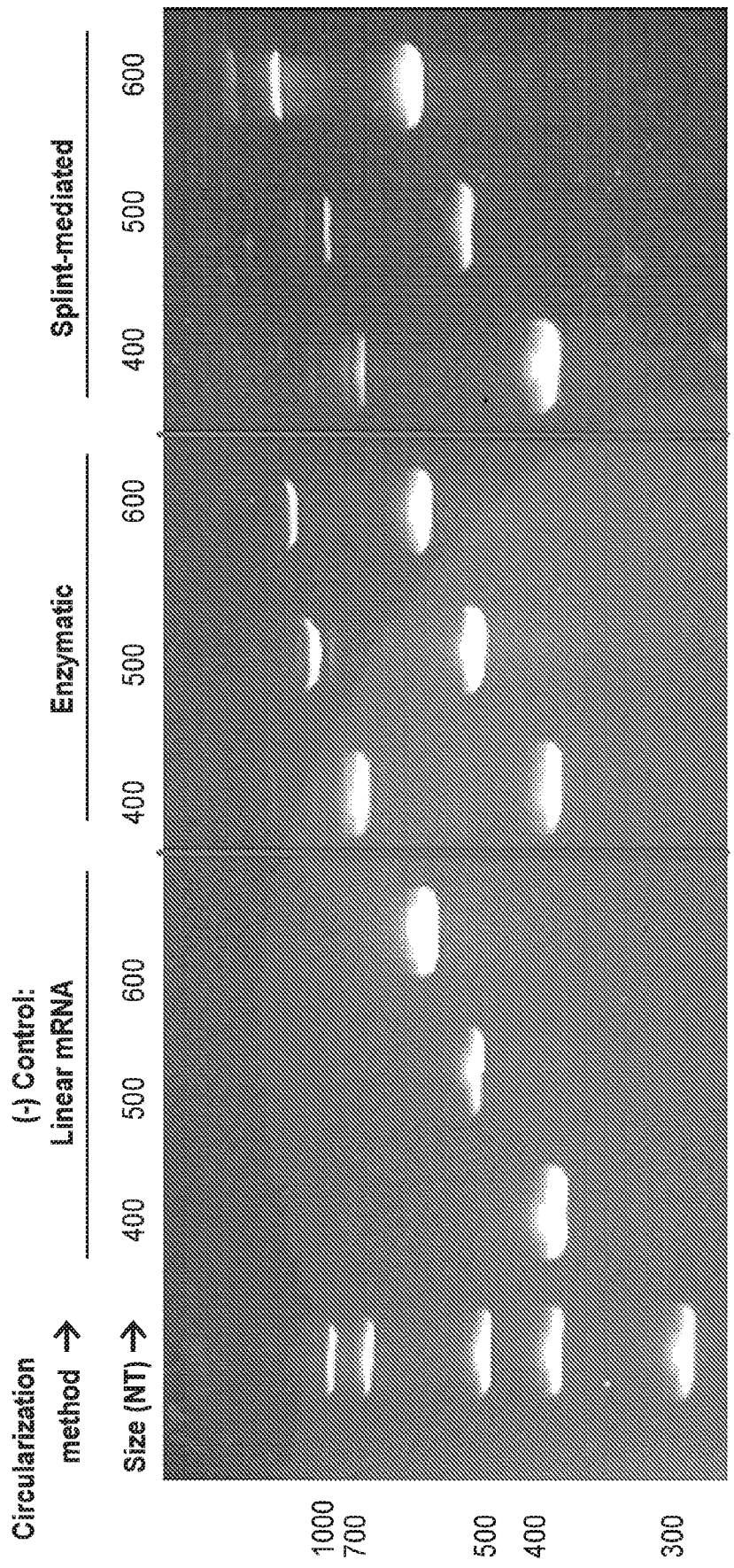
FIG. 1 includes a gel showing that enzymatic circularization produces the highest levels of circularized product (slower-migrating upper band) using existing protocols. Circularized product was never observed from the permuted intron-exon method, so these samples were not included in this gel.

The invention provides circularized nucleic acids (e.g. RNA), compositions comprising circularized nucleic acids, methods of circularizing nucleic acids, and methods using circularized nucleic acids. The nucleic acids, compositions, and methods are based upon the observation that circularization is more dependent on the availability of the free ends of the RNA than the size of the RNA construct.

RNA-based therapy affords benefits of gene therapy while remaining transient. Because RNA may be used as a transient, cytoplasmic expression system, RNA-based therapies can be applied in quiescent and/or slowly proliferating cells (i.e. muscle cells and hepatocytes). However, the instability of RNA, due to exonuclease-mediated degradation, has limited its clinical translation. In particular, the majority of RNA is degraded by exonucleases acting at both ends or at one end of the molecule after deadenylation and decapping. The sub-optimal stability of linear RNA remains an unresolved issue hindering the feasibility of RNA-based therapies. The majority of efforts to stabilize RNA have focused on linear RNA and modification thereof.

Linear RNA is prone to exonuclease degradation from the 5' to 3' end and the 3' to 5' end, whereas circularized RNA transcripts have increased serum stability at least in part because the exonuclease binding sites are no longer accessible to exonucleases. However, there are currently no effective methods for producing large-scale circularized RNA suitable for therapeutic purposes. Prior techniques have relatively low yield, poor reproducibility of the reaction, and been limited by the size and types of RNA sequences that can be made circular.

In contrast, the current method possesses several new and advantageous features overcoming prior disadvantages encountered with other methods of creating circularized RNA. Indeed, the present invention provides, at least, the following advantages: 1) an optimized method for generating circularized RNA in higher yields than previously obtained; 2) circularized RNA encoding therapeutic proteins; 3) circularized RNA having improved stability (in solution, in cells, and in vivo); 4) longer circularized RNA molecules than previously obtained; 5) use of circularized RNA for therapeutic gene transfer into cells; 6) use of circularized RNA for improved vaccination; and 7) use of circularized non-coding RNA for binding to endogenous target RNAs and/or RNA-binding proteins.

The object of the present invention was to develop a method for preparation of a wide variety of circularized RNA molecules. Consequently, the present invention identified motifs in the 5' and 3' untranslated regions of the transcript that enable and enhance cap-independent translation.

Circularized RNA

The present invention is based upon 5' and 3' motifs that allow highly efficient enzymatic circularization of RNA. Specifically, it was discovered that complement-reverse complement (CRC) sequence motifs together with random nucleotides at the 5' and 3' ends of a desired RNA facilitates enzymatic circularization of RNA.

Accordingly, the invention provides a nucleic acid (DNA or RNA) comprising having a 5' complement-reverse complement (CRC) sequence; a 5' untranslated region (UTR) sequence; a RNA sequence; a 3' untranslated region (UTR) sequence; and a 3' CRC sequence. The RNA sequence may be an RNA sequence capable of being translated into a polypeptide; the RNA sequence may be a non-coding RNA e.g., an RNA that is a reverse complement of an endogenous RNA, i.e., an mRNA, a miRNA, a tRNA, an rRNA, or a lncRNA; or the RNA sequence may be capable of binding to an RNA-binding protein (RBP). When the RNA sequence binds an RBP, the nucleic acid of the present invention prevents the RBP from binding to its canonical linear RNA binding partner. In a nucleic acid, a 5' CRC sequence may be partially complementary to a 3' CRC sequence (i.e., including at least one pair of complementary nucleotides but not necessarily completely complementary).

The 5' or 3' complement-reverse complement sequence comprises 10 to 50 nucleotides, e.g., 10, 20, 30, 40, and 50 nucleotides. Preferably, the CRC sequence comprises the nucleotide sequence: tggctgcacgaattgcacaa (SEQ ID NO: 1) or ttgtgcaattcgtgcagcca (SEQ ID NO: 2).

The nucleic acid further incudes a random nucleotide sequence at the 5' end and the 3' end. The 5' random nucleotide sequence is upstream of the 5' CRC sequence, and the 3' random nucleotide sequence is downstream of the 3' CRC sequence.

Each random nucleotide sequence is between about 5 and 50 nucleotides, e.g., 10, 15, 20, and 25 nucleotides.

Rather than having random nucleotide sequences, a nucleic acid may have one or two polyA sequences, with the polyA sequences being upstream of a 5' CRC and/or downstream of a 3' CRC and at the nucleic acid's end(s).

Each polyA sequence is between about 5 and 50 nucleotides, e.g., 10, 15, 20, 25, and 30 nucleotides.

Preferred 5' or 3' complement-reverse complement sequences and random nucleotide sequences are exemplified in TABLE 1.

TABLE 1

| # | Primer Name (Forward) | Vector | Primer Size | T7 | 5' Random | 5' CRC | First 10 NT of PPT19x4 | Last 10 NT of ElastinX3 | 3' CRC | 5' Random | Size | Reverser Complement | Primer Name (Reverse) |
|---|---|---|---|---|---|---|---|---|---|---|---|---|---|
| 1 | 558_Hetero_10-10_F | Hetero | 47 | taatacga ctcactata | GGGAATC GAC | TGCCGT CGGT | AAAAGAA GGA | gaggga ggga | ACCGA CGGCA | CGGAAT ATAG | 30 | CTATATTCC GTGCCGTCG GTccctccctc | 559_Het ero_10-10_R |
| 2 | 560_Hetero_15-10_F | Hetero | 52 | taatacga ctcactata | GGGAATC GACTACA G | TGCCGT CGGT | AAAAGAA GGA | gaggga ggga | ACCGA CGGCA | CGGAAT ATAG AAGCA | 35 | TGCTTCTATA TTCCGTGCC GTCGGTtccc tccctc | 561_Het ero_15-10_R |
| 3 | 562_Hetero_20-10_F | Hetero | 57 | taatacga ctcactata | GGGAATC GACTACA GGAGGA | TGCCGT CGGT | AAAAGAA GGA | gaggga ggga | ACCGA CGGCA | CGGAAT ATAG AAGCAT AAGA | 40 | TCTTATGCTT CTATATTCC GTGCCGTCG GTccctccctc | 563_Het ero_20-10_R |
| 4 | 564_Hetero_10A-10_F | Hetero | 47 | taatacga ctcactata | GGGAAAA AAA | TGCCGT CGGT | AAAAGAA GGA | gaggga ggga | ACCGA CGGCA | AAAAAA AAAA | 30 | TTTTTTTTTT TGCCGTCGG Ttccctccctc | 565_Het ero_10-10_R |
| 5 | 566_Hetero_15A-10_F | Hetero | 52 | taatacga ctcactata | GGGAAAA AAAAAAA A | TGCCGT CGGT | AAAAGAA GGA | gaggga ggga | ACCGA CGGCA | AAAAAA AAAAAA AAA | 35 | TTTTTTTTTT TTTTTGCCG TCGGTccctc cctc | 567_Het ero_15A-10_R |
| 6 | 568_Hetero_20A-10_F | Hetero | 57 | taatacga ctcactata | GGGAAAA AAAAAAA AAAAAA | TGCCGT CGGT | AAAAGAA GGA | gaggga ggga | ACCGA CGGCA | AAAAAA AAAAAA AAAAAA AA | 40 | TTTTTTTTTT TTTTTTTTTT TGCCGTCGG Ttccctccctc | 569_Het ero_20A-10_R |
| 7 | 570_Hetero_10-20_F | Hetero | 57 | taatacga ctcactata | GGGAATC GAC | AACACG TTAT TGCCCGT CGGT | AAAAGAA GGA | gaggga ggga | ACCGA CGGCA ATAAC GTGTT | CGGAAT ATAG | 40 | CTATATTCC GAACACGTT ATTGCCCTC GGTtccctccct | 571_Het ero_10-20_R |
| 8 | 572_Hetero_15-20_F | Hetero | 62 | taatacga ctcactata | GGGAATC GACTACA G | AACACG TTAT TGCCCGT CGGT | AAAAGAA GGA | gaggga ggga | ACCGA CGGCA ATAAC GTGTT | CGGAAT ATAG AAGCA | 45 | TGCTTCTATA TTCCGAACA CGTTATTGC CGTCGGTtcc ctccctc | 573_Het ero_15-20_R |

TABLE 1-continued

| | | | | | | | | | | | |
|---|---|---|---|---|---|---|---|---|---|---|---|
| 9 | 574_Hete ro_20-20_F | Hetero | 67 | taatacga ctcactata | GGGAATC GACTACA GGAGGA | AACACG TTAT TGCCGT CGGT | AAAAGAA GGA | gaggga ggga | ACCGA CGGCA ATAAC GTGTT | CGGAAT ATAG AAGCAT AAGA | 50 | TCTTATGCTT CTATATTCC GAACACGTT ATTGCCGTC GGTtccctccct | 575_Het ero_20-20_R |
| 10 | 576_Hete ro_10A-20_F | Hetero | 57 | taatacga ctcactata | GGGAAAAA AAA | AACACG TTAT TGCCGT CGGT | AAAAGAA GGA | gaggga ggga | ACCGA CGGCA ATAAC GTGTT | GGGAAAA AAAA | 40 | TTTTTTTCCC AACACGTTA TTGCCGTCG GTtccctccctc | 577_Het ero_10A-20_R |
| 11 | 578_Hete ro_15A-20_F | Hetero | 62 | taatacga ctcactata | GGGAAAA AAAAAAAA A | AACACG TTAT TGCCGT CGGT | AAAAGAA GGA | gaggga ggga | ACCGA CGGCA ATAAC GTGTT | GGGAAAA AAAAAAA AAA | 45 | TTTTTTTTTT TTCCCAACA CGTTATTGC CGTCGGTtcc ctccctc | 579_Het ero_15A-20_R |
| 12 | 580_Hete ro_20A-20_F | Hetero | 67 | taatacga ctcactata | GGGAAAAA AAAAAAAAA AAAAAAA | AACACG TTAT TGCCGT CGGT | AAAAGAA GGA | gaggga ggga | ACCGA CGGCA ATAAC GTGTT | GGGAAAA AAAAAAAA AA | 50 | TTTTTTTTTT TTTTTTCCC AACACGTTA TTGCCGTCG GTtccctccctc | 581_Het ero_20A-20_R |
| 13 | 582_Hete ro_10-30_F | Hetero | 67 | taatacga ctcactata | GGGAATC GAC | GTTACG TACC AACACG TTAT TGCCGT CGGT | AAAAGAA GGA | gaggga ggga | ACCGA CGGCA ATAAC GAGTT GGTAAC | CGGAAT ATAG | 50 | CTATATTCC GGTTACGTA CCAACACGT TATTGCCGT CGGTtccctcc ctc | 583_Het ero_10-30_R |
| 14 | 584_Hete ro_15-30_F | Hetero | 72 | taatacga ctcactata | GGGAATC GACTACA G | GTTACG TACC AACACG TTAT TGCCGT CGGT | AAAAGAA GGA | gaggga ggga | ACCGA CGGCA ATAAC GTGTT GGTAAC | CGGAAT ATAG AAGCA | 55 | TGCTTCTATA TTCCGGTTA CGTACCAAC ACGTTATTG CCGTCGGTtc ctccctc | 585_Het ero_15-30_R |
| 15 | 586_Hete ro_25-30_F | Hetero | 77 | taatacga ctcactata | GGGAATC GACTACA GGAGGA | GTTACG TACC AACACG TTAT TGCCGT CGGT | AAAAGAA GGA | gaggga ggga | ACCGA CGGCA ATAAC GTGTT GGTAAC GTAAC | CGGAAT ATAG AAGCAT AAGA | 60 | TCTTATGCTT CTATATTGCTA GGTTACGTA CCAACACGT TATTGCCGT CGGTtccctcc ctc | 587_Het ero_20-30_R |

TABLE 1-continued

| | | | | | | | | | | | |
|---|---|---|---|---|---|---|---|---|---|---|---|
| 16 | Hetero | 588_Hetero_10A-30_F | 67 | taatacga ctcactata | GGGAAAAA AAA | GTTACG TACC AACACG TTAT TGCCGT CGGT | AAAAGAA GGA | gaggga ggga | ACCGA CGGCA ATAAC GTGTT GGTAC GTAAC | AAAAAAA AAAA | 50 | TTTTTTTTTT GTTACGTAC CAACACGTT ATTGCCGTC GGTccctccct | 589_Hetero_10A-30_R |
| 17 | Hetero | 590_Hetero_15A-30_F | 72 | taatacga ctcactata | GGGAAAAA AAAAAAA A | GTTACG TACC AACACG TTAT TGCCGT CGGT | AAAAGAA GGA | gaggga ggga | ACCGA CGGCA ATAAC GTGTT GGTAC GTAAC | AAAAAAA AAAAA AAA | 55 | TTTTTTTTTT TTTTTGTTAC GTACCAACA CGTTATTGC CGTCGGTtcc ctccctc | 591_Hetero_15A-30_R |
| 18 | Hetero | 592_Hetero_20A-30_F | 77 | taatacga ctcactata | GGGAAAAA AAAAAAAA AAAAAA | GTTACG TACC AACACG TTAT TGCCGT CGGT | AAAAGAA GGA | gaggga ggga | ACCGA CGGCA ATAAC GTGTT GGTAC GTAAC | AAAAAAA AAAAAAA AA | 60 | TTTTTTTTTT TTTTTTTTTT GTTACGTAC CAACACGTT ATTGCCGTC GGTccctccct c | 593_Hetero_20A-30_R |
| 19 | Hetero | 594_Hetero_10-40_F | 77 | taatacga ctcactata | GGGAATC GAC | AGGTTC GAAG GTTACG TACC AACACG TTAT TGCCGT CGGT | AAAAGAA GGA | gaggga ggga | ACCGA CGGCA ATAAC GTGTT GGTAC GTAAC CTTCG AACCT | CGGAAT ATAG | 60 | CTATATATTCC GAGGTTCGA AGGTTACGT ACCAACACG TTATTGCCG TCGGTtccctc cctc | 595_Hetero_10-40_R |
| 20 | Hetero | 596_Hetero_15-40_F | 82 | taatacga ctcactata | GGGAATC GACTACA G | AGGTTC GAAG GTTACG TACC AACACG TTAT TGCCGT CGGT | AAAAGAA GGA | gaggga ggga | ACCGA CGGCA ATAAC GTGTT GGTAC GTAAC CTTCG AACCT | CGGAAT ATAG AAGCA | 65 | TGCTTCTATA TTCCGAGGT TCGAAGGTT ACGTACCAA CACGTTATT GCCGTCGGT tccctccctc | 597_Hetero_15-40_R |
| 21 | Hetero | 598_Hetero_20-40_F | 87 | taatacga ctcactata | GGGAATC GACTACA GGAGGA | AGGTTC GAAG GTTACG TACC AACACG TTAT TGCCGT CGGT | AAAAGAA GGA | gaggga ggga | ACCGA CGGCA ATAAC GTGTT GGTAC GTAAC CTTCG AACCT | CGGAAT ATAG AAGCAT AAGA | 70 | TCTTATGCTT CTATATTCC GAGGTTCGA AGGTTACGT ACCAACACG TTATTGCCG TCGGTtccctc cctc | 599_Hetero_20-40_R |

TABLE 1-continued

| | | | | | | | | | | | | |
|---|---|---|---|---|---|---|---|---|---|---|---|---|
| 22 | 600_Hete ro_10A-40_F | Hetero | 77 | taatacga ctcactata | GGGAAAA AAA | AGGTTC GAAG GTTACG TACC AACACG TTAT TGCCGT CGGT | AAAAGAA GGA | gaggga ggga | ACCGA CGGCA ATAAC GTGTT GGTAC GTAAC CTTCG AACCT | AAAAAAA AAAA | 60 | TTTTTTTTTT AGGTTCGAA GGTTACGTA CCAACACGT TATTGCCGT CGGTtccctcc ctc | 601_Het ero_10A-40_R |
| 23 | 602_Hete ro_15A-40_F | Hetero | 82 | taatacga ctcactata | GGGAAAA AAAAAAA A | AGGTTC GAAG GTTACG TACC AACACG TTAT TGCCGT CGGT | AAAAGAA GGA | gaggga ggga | ACCGA CGGCA ATAAC GTGTT GGTAC GTAAC CTTCG AACCT | AAAAAAA AAAAAA AAA | 65 | TTTTTTTTTT TTTTTAGGTT CGAAGGTTA ACGTTATTG CCGTCGGTtc cctcctc | 603_Het ero_15A-40_R |
| 24 | 604_Hete ro_20A-40_F | Hetero | 87 | taatacga ctcactata | GGGAAAA AAAAAAAA AAAAAAA | AGGTTC GAAG GTTACG TACC AACACG TTAT TGCCGT CGGT | AAAAGAA GGA | gaggga ggga | ACCGA CGGCA ATAAC GTGTT GGTAC GTAAC CTTCG AACCT | AAAAAAA AAAAAA AA | 70 | TTTTTTTTTT TTTTTTTTTT AGGTTCGAA GGTTACGTA CCAACACGT TATTGCCGT CGGTtccctcc ctc | 605_Het ero_20A-40_R |
| 25 | 606_Hom o_10-10_F | Homo | 47 | taatacga ctcactata | GGGAATC GAC | cccccccc cc | AAAAGAA GGA | gaggga ggga | gggggg gggg | CGGAAT ATAG | 30 | CTATATTCC Gccccccccct ccctcctc | 607_Ho mo_10-10_R |
| 26 | 608_Hom o_15-10_F | Homo | 52 | taatacga ctcactata | GGGAATC GACTACA G | cccccccc cc | AAAAGAA GGA | gaggga ggga | gggggg gggg | CGGAAT ATAG AAGCA | 35 | TGCTTCTATA TTCCGccccc cccctcctccct | 609_Ho mo_15-10_R |
| 27 | 610_Hom o_20-10_F | Homo | 57 | taatacga ctcactata | GGGAATC GACTACA GGAGGA | cccccccc cc | AAAAGAA GGA | gaggga ggga | gggggg gggg | CGGAAT ATAG AAGCAT AAGA | 40 | TCTTATGCTT CTATATTCC Gccccccccct ccctcctc | 611_Ho mo_20-10_R |
| 28 | 612_Hom o_10A-10_F | Homo | 47 | taatacga ctcactata | GGGAAAA AAA | cccccccc cc | AAAAGAA GGA | gaggga ggga | gggggg gggg | AAAAAAA AAAA | 30 | TTTTTTTTTTc cccccccctcc ctccctc | 613_Ho mo_10A-10_R |

TABLE 1-continued

| | | | | | | | | | | | | |
|---|---|---|---|---|---|---|---|---|---|---|---|---|
| 29 | 614_Homo_15A-10_F | Homo | 52 | taatacga ctcactata | GGGAAAA AAAAAAA A | ccccccc cc | AAAAGAA GGA | gaggga ggga | gggggg gggg | AAAAAAA AAAAAAA AAA | 35 | TTTTTTTTTT TTTTccccccc cccccctccct c | 615_Ho mo_15A-10_R |
| 30 | 616_Homo_20A-10_F | Homo | 57 | taatacga ctcactata | GGGAAAA AAAAAAA AAAAAA | ccccccc cc | AAAAGAA GGA | gaggga ggga | gggggg gggg | AAAAAAA AAAAAAA AA | 40 | TTTTTTTTTT TTTTTTTTTc cccccccccc ctccctc | 617_Ho mo_20A-10_R |
| 31 | 618_Homo_10-40_F | Homo | 77 | taatacga ctcactata | GGGAATC GAC | ccccccc cccccccc cccccccc | AAAAGAA GGA | gaggga gga | gggggg gggggg gggggg gggg | CTATATTCC G | 60 | CTATATTCC Gcccccccc cccccccc cccccccc ctcccctc ctc | 619_Ho mo_10-40_R |
| 32 | 620_Homo_15-40_F | Homo | 82 | taatacga ctcactata | GGGAATC GACTACA G | ccccccc cccccccc cccccccc | AAAAGAA GGA | gaggga ggga | gggggg gggggg gggggg ggg | CGGAAT ATAG | 65 | TGCTTCTATA TTCCGccccc cccccccc cccccccc cctccctc | 621_Ho mo_15-40_R |
| 33 | 622_Homo_20-40_F | Homo | 87 | taatacga ctcactata | GGGAATC GACTACA GGAGGA | ccccccc cccccccc cccccccc | AAAAGAA GGA | gaggga ggga | gggggg gggggg gggggg gggg | CGGAAT ATAG AAGCA | 70 | TCTTATGCTT CTATATTCC Gcccccccc cccccccc cccccccc ctc | 623_Ho mo_20-40_R |
| 34 | 624_Homo_10A-40_F | Homo | 77 | taatacga ctcactata | GGGAAAA AAA | ccccccc cccccccc cccccccc | AAAAGAA GGA | gaggga ggga | gggggg gggggg gggggg gggg | CGGAAT ATAG AAGCAT AAGA | 60 | TTTTTTTTTTc cccccccc cccccccc cccccccc cctcccctcctc | 625_Ho mo_10A-40_R |

TABLE 1-continued

| | | | | | | | | | | | |
|---|---|---|---|---|---|---|---|---|---|---|---|
| 35 | 626_Homo_15A-40_F | Homo | 82 | taatacga ctcactata | GGGAAAA AAAAAAA A | cccccccc cccccccc cccccccc cccccccc | AAAAGAA GGA | gaggga ggga | ggggggg ggggggg ggggggg ggggggg ggggggg gggg | AAAAAAA AAAAAAA AAA | 65 | TTTTTTTTT TTTTTccccccccc ccccccccccc cccccccccc cctccctc | 627_Homo_15A-40_R |
| 36 | 628_Homo_20A-40_F | Homo | 87 | taatacga ctcactata | GGGAAAA AAAAAAA AAAAAA | cccccccc cccccccc cccccccc cccccccc | AAAAGAA GGA | gaggga ggga | ggggggg ggggggg ggggggg ggggggg ggggggg ggg | AAAAAAA AAAAAAA AA | 70 | TTTTTTTTT TTTTTTTTTc ccccccccccc cccccccccc ccctccctccctc | 629_Homo_20A-40_R |
| 37 | 630_OG_10-20_F | Original | 60 | taatacga ctcactata ggg | ttatgata ac | tggctgca cgaattgc acaa | AAAAGAA GGA | gaggga ggga | ttgtgca attcgtg cagcca | agcgactt cg | 40 | cgaagtcgcttg gctgcacgaatt gcacaatccctc cctc | 631_OG_10-20_R |

The 5' UTR is any UTR known in the art. For example, the 5' UTR is polyAx30, polyAx120, PPT19, PPT19x4, GAAAx7, or polyAx30-EMCV. Preferably, the 5' UTR is PPT19 or EMCV. Any known 3' UTR may be used in the present invention; examples include HbB1-PolyAx10, HbB1, HbB1x2, or an Elastin-derived 3' UTR (e.g., a motif from the Elastin 3' UTR). Preferably, the 3' UTR is an Elastin-derived 3' UTR. Multiple tandem copies (e.g., 2, 3, 4, or more) of a UTR may be included in a nucleic acid (e.g., more than one copy of a motif from the Elastin 3' UTR and more than one copy of the PPT19 5' UTR). As used herein, the number after an "x" in a UTR's name refers to the number of copies of the UTR (or motif thereof). As an example, an Elastin 3' UTR (or a motif thereof) that is repeated twice is referred to as Elastinx2 and an Elastin 3' UTR (or a motif thereof) that is repeated three times is referred to as Elastinx3.

The 5' and 3' motifs identified by the inventors allow any size target RNA to be circularized. The RNA sequence is at least 15, 30, 50, 100, 200, 300, 400, 500, 600, 700, 800, 900, 1000, 2000, 3000, 4000, 5000, 6000, 7000, 8000, 9000, 10000, or more nucleotides in length.

The RNA (e.g., mRNA) sequence may encode any protein of interest, for example the target RNA encodes for a hormone, scFv, single-domain antibody (also known as a nanobody), cytokine, intracellular protein, extracellular protein, tumor-associated antigen, chimeric antigen receptor, bacterial antigen, viral antigen, transposase, nuclease, or transcription factor. The RNA may encode a therapeutic polypeptide, e.g., preproinsulin, hypocretin, human growth hormone, leptin, oxytocin, vasopressin, factor VII, factor VIII, factor IX, erythropoietin, G-CSF, alpha-galactosidase A, iduronidase, N-acetylgalactosamine-4-sulfatase, FSH, DNase, tissue plasminogen activator, glucocerebrosidase, interferon, and IGF-1. The translated protein would have endogenous post-translational modifications and could be retained intracellularly or secreted. The RNA sequence may encode a polypeptide that comprises an epitope for presentation by an antigen presenting cell. The polypeptide may lead to improved (e.g., more efficient and greater quantity) T-cell priming, as determined by increased production of IFN-γ, including by proliferating cells.

The RNA sequence may be an RNA that is a reverse complement of an endogenous RNA, i.e., an mRNA, a miRNA, a tRNA, an rRNA, or a lncRNA; by "endogenous" is meant an RNA that is naturally transcribed by a cell. An RNA sequence that is a reverse complement may be referred to as a "non-coding RNA" since it does not encode a polypeptide. When an RNA sequence of the present invention binds an endogenous RNA, the endogenous RNA's function may be blocked or reduced; for example, when the endogenous RNA is an miRNA, the RNA sequence of the present invention prevents the miRNA from binding to its target mRNAs.

The RNA sequence may be capable of binding to an RNA-binding protein (RBP). When the RNA sequence binds an RBP, the nucleic acid of the present invention prevents the RBP from binding to its canonical linear RNA binding partner. Non-limiting examples of RBPs are found at the World Wide Web (www) at rbpdb.ccbr.utoronto.ca.

A circularized nucleic acid will have greater stability (i.e., more resistant to degradation or enzymatic digestion) than a nucleic acid having a similar sequence (e.g., identical or non-identical) but is non-circularized. The circularized nucleic acid will have greater stability in solution. A circularized nucleic acid will have greater stability in a cell, whether in vitro or in vivo (i.e., in an animal). By "greater stability" is meant a stability increase of 0.01%, 1%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 6000%, 7000%, 8000%, 9000%, 10000%, or more or any percentage therebetween. For example, a greater (as defined above) fraction of the starting amount of circularized nucleic acid will remain in a solution or a cell after a certain amount of time when under identical conditions (e.g., temperature and presence/absence of digestive enzymes) than a corresponding non-circularized nucleic acid.

A circularized nucleic acid may provide greater polypeptide translation (e.g., more polypeptide product and more efficient synthesis) relative to a nucleic acid having a similar sequence (e.g., identical or non-identical) but is non-circularized. By "greater polypeptide translation" is meant an increase of 0.01%, 1%, 10%, 20%, 30%, 40%, 50%, 60%, 70%, 80%, 90%, 100%, 200%, 300%, 400%, 500%, 600%, 700%, 800%, 900%, 1000%, 2000%, 3000%, 4000%, 5000%, 6000%, 7000%, 8000%, 9000%, 10000%, or more or any percentage therebetween in the amount of polypeptide produced. For example, a greater (as defined above) number of polypeptides will be synthesized from a molecule of circularized nucleic acid than from a corresponding non-circularized nucleic acid.

A nucleic acid may comprise an internal ribosome entry site (IRES). Exemplary IRES sequences are listed at the World Wide Web at iresite.org. Preferably, the IRES is an encephalomyocarditis virus (EMCV) IRES or a PPT19 IRES.

A nucleic acid of the present invention may be in a cell (e.g., in vitro or in vitro in a non-human mammal). Non-limiting examples of cells include T cells, B cells, Natural Killer cells (NK), Natural Killer T (NKT) cells, mast cells, eosinophils, basophils, macrophages, neutrophils, and dendritic cells.

A circularized nucleic acid of the present invention may be included in a composition, e.g., a pharmaceutical composition suitable for administration to a subject, e.g., a mammal, including a human. The composition may include both a circularized nucleic acid of the present invention and a nucleic acid having a similar sequence (e.g., identical or non-identical) but is non-circularized.

Methods for Circularizing RNA

The nucleic acid comprising the RNA sequence to be circularized can be produced by methods known in the art.

For example, primers can be designed to generate PCR templates suitable for in vitro transcription (IVT), for example by T7, T3, or S6 RNA polymerase. Preferably, the primers are designed with the following motifs:

Forward primer: {RNA polymerase promoter sequence-5'-(random nucleotides)-(5'CRC sequence)-(desired 5' UTR)-($1^{st}$ 20 nucleotides of desired RNA CDS)-3'}

Reverse primer: {5'-(random nucleotides)-(3'CRC sequence)-(reverse complement of desired 3' UTR)-(reverse complement of last 20 nucleotides of desired RNA CDS)-3'}

Circularized RNA is produced by transcription of the PCR products generated with the above primers, or another set of primers, to produce RNA. The synthesized RNA is then treated to produce a 5' monophosphate RNA. For example, 5' monophosphate RNA is produced by treating the RNA with RNA 5' pyrophosphohydrolase (RppH) or an ATP diphosphohydrolase.

The 5' monophosphate RNA is then enzymatically circularized for example with an RNA ligase such as T4 RNA ligase.

A nucleic acid of the present invention, which is non-circularized, may be circularized by ligating its 5' terminus to its 3' terminus. Ligating may be enzymatic, e.g., by a ligase. Preferably, the ligase is T4 RNA ligase.

Prior to ligation, a non-circularized nucleic acid is contacted with a phosphatase, e.g., RNA 5' pyrophosphohydrolase (RppH) or an ATP diphosphohydrolase, to produce a 5' monophosphate RNA. Alternately, a non-circularized nucleic acid is contacted with a phosphatase, e.g., Antarctic Phosphatase, Shrimp Alkaline Phosphatase, and Calf Intestinal Phosphatase, and then contacted with a kinase, e.g., Polynucleotide Kinase.

A nucleic acid may undergo multiple (e.g., two, three, four, five, or more) rounds of ligation, thereby ensuring that the majority of nucleic acids, in a sample, is circularized, e.g., about 100%, about 90%, about 80%, about 70%, about 60%, about 51%, or any amount therebetween.

Optionally, non-circularized (i.e., linear) RNA is removed using an exonuclease to digest the linear RNA, e.g., RNase R, Exonuclease T, a, Exonuclease, Exonuclease I, Exonuclease VII, T7 Exonuclease, or XRN-1. Preferably, the exonuclease is RNase R and/or XRN-1.

Methods of Using Circularized RNA

The circularized RNA produced according to the methods of the invention are useful in gene therapy. In particular, the circularized RNA is useful for protein replacement therapy or in the production of RNA-based vaccines for an array of antigens. For example, the circularized RNA (e.g., mRNA) can encode tumor-associated antigens useful as cancer vaccines. In another aspect, the circularized RNA (e.g., mRNA) can encode a bacterial or viral antigen to prevent or alleviate a symptom of a bacterial or viral infection, e.g., as a vaccine. Additional embodiments include use of circularized RNA for use in cancer immunotherapies, infectious disease vaccines, genome engineering, genetic reprogramming, and protein-replacement/supplementation therapies.

Alternatively, the circularized RNA (e.g., mRNA) can encode a chimeric antigen receptor and be used to create a chimeric antigen receptor T-cell useful in immunotherapy. Chimeric antigen receptors (CARs) comprise binding domains derived from natural ligands or antibodies specific for cell-surface antigens, genetically fused to effector molecules such as the TCR alpha and beta chains, or components of the TCR-associated CD3 complex. Upon antigen binding, such chimeric antigen receptors link to endogenous signaling pathways in the effector cell and generate activating signals similar to those initiated by the TCR complex. A CAR typically has an intracellular signaling domain, a transmembrane domain, and an extracellular domain.

The transmembrane and/or intracellular domain may include signaling domains from CD8, CD4, CD28, 4-1BB, OX40, ICOS, and/or CD3-zeta. The transmembrane domain can be derived either from a natural or from a synthetic source. The transmembrane domain can be derived from any membrane-bound or transmembrane protein.

The transmembrane domain may further include a stalk region positioned between the extracellular domain (e.g., extracellular ligand-binding domain) and the transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain.

The signal transducing domain or intracellular signaling domain of the CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCR zeta, FcR gamma, FcR beta, FcR epsilon, CD3 gamma, CD3 delta, CD3 epsilon, CD5, CD22, CD79a, CD79b and CD66d. In a preferred embodiment, the signaling transducing domain of the CAR can comprise the CD3 zeta signaling domain, or the intracytoplasmic domain of the Fc epsilon RI beta or gamma chains.

The CAR may further include one or more additional costimulatory molecules positioned between the transmembrane domain and the intracellular signaling domain, to further augment potency. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like. In some embodiments the intracellular signaling domain contains 2, 3, 4, or more costimulatory molecules in tandem.

The extracellular domain may include an antibody such as a Fab, a scFV, or a single-domain antibody (sdAb also known as a nanobody) and/or may include another polypeptide described herein. In a preferred embodiment, said extracellular ligand-binding domain is a single chain antibody fragment (scFv) comprising the light (VL) and the heavy (VH) variable fragment of a target antigen specific monoclonal antibody joined by a flexible linker. Other binding domain than scFv can also be used for predefined targeting of lymphocytes, such as camelid single-domain antibody fragments (which are examples of an sdAb) or receptor ligands, antibody binding domains, antibody hypervariable loops or CDRs as non limiting examples.

As non limiting examples, the antigen of the CAR can be a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialoganglioside GD2, ductal-epithelial mucine, gp36, TAG-72, glycosphingolipids, glioma-associated antigen, beta-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelia, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C(TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers.

A circularized nucleic acid of the present invention may encode a CAR and may be transfected or infected into a T-cell using any technique known in the art. A T-cell that expresses the CAR is referred to as a chimeric T-cell receptor cell (CART). The CART will express and bear on the cell surface membrane the chimeric antigen receptor encoded by the RNA sequence of a circularized nucleic acid of the present invention.

The present invention includes a nucleic acid encoding a CAR, methods for preparing a nucleic acid encoding a CAR, compositions comprising a nucleic acid encoding a CAR, methods for producing a CART, methods for treating a diseases using a CART, an isolated CART, and non-human mammals comprising a CART.

Any of the herein-described aspects or embodiments can be combined with any other aspect or embodiment described herein.

Definitions

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety as defined herein. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Modified bases refer to nucleotide bases such as, for example, adenine, guanine, cytosine, thymine, and uracil, xanthine, inosine, and qucuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group. Preferably, the modified base is 5-methylcytidine (5mC).

Further, the term nucleotide also includes those species that have a detectable label, such as for example a radioactive or fluorescent moiety, or mass label attached to the nucleotide.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine and thymine (G, C, A and T, respectively).

The terms "ribonucleic acid" and "RNA" as used herein mean a polymer composed of ribonucleotides.

As used herein, the terms "mRNA" and "RNA" may be synonyms.

The terms "deoxyribonucleic acid" and "DNA" as used herein mean a polymer composed of deoxyribonucleotides. "Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

As defined herein, "RNA ligase" means an enzyme or composition of enzyme that is capable of catalyzing the joining or ligating of an RNA acceptor oligonucleotide, which has an hydroxyl group on its 3' end, to an RNA donor, which has a 5' phosphate group on its 5' end. The invention is not limited with respect to the RNA ligase, and any RNA ligase from any source can be used in an embodiment of the methods and kits of the present invention. For example, in some embodiments, the RNA ligase is a polypeptide (gp63) encoded by bacteriophage T4 gene 63; this enzyme, which is commonly referred to simply as "T4 RNA ligase," is more correctly now called "T4 RNA ligase 1" since Ho, C K and Shuman, S (Proc. Natl. Acad. Sci. USA 99: 12709-12714, 2002) described a second RNA ligase (gp24.1) that is encoded by bacteriophage T4 gene 24.1, which is now called "T4 RNA ligase 2." Unless otherwise stated, when "T4 RNA ligase" is used in the present specification, is meant "T4 RNA ligase 1". For example, in some other embodiments, the RNA ligase is a polypeptide derived from or encoded by an RNA ligase gene from bacteriophage TS2126, which infects *Thermus scotoductus*, as disclosed in U.S. Pat. No. 7,303,901 (i.e., bacteriophage TS2126 RNA ligase).

Linear nucleic acid molecules are said to have a "5'-terminus" (5' end) and a "3'-terminus" (3' end) because nucleic acid phosphodiester linkages occur at the 5' carbon and 3' carbon of the sugar moieties of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus "Transcription" means the formation or synthesis of an RNA molecule by an RNA polymerase using a DNA molecule as a template. The invention is not limited with respect to the RNA polymerase that is used for transcription. For example, a T7-type RNA polymerase can be used.

"Translation" means the formation of a polypeptide molecule by a ribosome based upon an RNA template.

It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless specifically stated or obvious from context, as used herein, the term "or" is understood to be inclusive. Unless defined herein and below in the reminder of the specification, all technical and scientific terms used herein have the same meaning as commonly understood by one of ordinary skill in the art to which the invention pertains.

Unless specifically stated or obvious from context, as used herein, the term "about", is understood as within a range of normal tolerance in the art, for example within 2 standard deviations of the mean. "About" can be understood as within 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the stated value. Unless otherwise clear from the context, all numerical values provided herein are modified by the term "about."

A "subject" in the context of the present invention is preferably a mammal. The mammal can be a human, non-human primate, mouse, rat, dog, cat, horse, or cow, but are not limited to these examples.

As used herein, the term "encode" refers broadly to any process whereby the information in a polymeric macromolecule is used to direct the production of a second molecule that is different from the first. The second molecule may have a chemical structure that is different from the chemical nature of the first molecule.

For example, in some aspects, the term "encode" describes the process of semi-conservative DNA replication, where one strand of a double-stranded DNA molecule is used as a template to encode a newly synthesized complementary sister strand by a DNA-dependent DNA polymerase. In other aspects, a DNA molecule can encode an RNA molecule (e.g., by the process of transcription that uses a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

EXAMPLES

Example 1: Circularized RNA Synthesis

RNA was synthesized using the HiScribe T7 High Yield RNA Synthesis Kit (NEB, #E2040S) according to manufacturer's instructions. 500-1000 ng of PCR product encoding the desired RNA sequence was used as template in these in vitro transcription (IVT) reactions. Synthesized RNA was then treated with RNA 5' Pyrophosphohydrolase, or RppH, (NEB, #M0356S) to provide the 5' monophosphate end necessary for enzymatic circularization. RppH-treated RNA was enzymatically circularized in reactions containing final concentrations of: 10% DMSO, 200 uM ATP, 1×NEB Buffer 4, 40 U RNaseOUT (Life Technologies, #10777-019), and 30 U of T4 RNA Ligase 1 (NEB, #M0204L) for 2 hours at 37° C. Any remaining linear RNA in the circularization reactions was removed using the exonuclease Xrn-1 (NEB, #M0338L). After each step, reactions were purified using the GeneJet RNA Purification Kit (Thermo Scientific, #K4082). Circularization was confirmed by running 500 ng of RNA product on a 6% polyacrylamide gel in 7 M Urea-TBE (Life Technologies, #EC6865) for 3 hours at 180 V, 4° C. Circularized product characteristically migrates slower than linear RNA, so a slower migrating band indicated circularized product when run alongside control non-circularized RNA. Additional confirmation was carried out using outward-oriented PCR (OOPCR), where primers are oriented outward from one other with respect to the linear template (as opposed to traditional PCR in which primers are oriented towards each other). cDNA was synthesized (Life Technologies, #4402954) from RNA samples and used as template in the OOPCR reactions. cDNA derived from non-circularized, linear RNA was used a negative control. An amplicon is generated solely from the circularized construct, as the polymerase can extend through the ligated ends.

Example 2: Circularized Generating CRC, 5' and 3' UTR Constructs

CRC sequences and experimental 5'/3' UTRs were appended to RNA coding sequence (CDS) by generating PCR templates for IVT that had been amplified with primers of the following design:

```
Forward primer:
5'-(TAATACGACTCACTATAGGG-)-(ttatgataac)-
(tggctgcacgaattgcacaa)-(desired 5' UTR)-(varied
based on RNA CDS)-3'
```

(primer comprises SEQ ID NOs: 3, 4, and 2, respectively)
{5'-(RNA polymerase promoter sequence)-(random nucleotides)-(5'CRC sequence)-(desired 5' UTR)-(1$^{st}$ 20 nucleotides of desired RNA CDS)-3'}.

```
Reverse primer:
5'-(agcgacttcg)-(ttgtgcaattcgtgcagcca)-
(desired 3' UTR)-(varied based on RNA CDS)-3'
```

(primer comprises SEQ ID NOs: 5 and 2, respectively)
{5'-(random nucleotides)-(3'CRC sequence)-(reverse complement of desired 3' UTR)-(reverse complement of last 20 nucleotides of desired RNA CDS)-3'}

PCR templates generated with the above primers were used to generate circularized product as described in the below "Improvements to Existing Methodology for RNA Circularization" Example.

Example 3: Circularized Degradation Protection Assay

Degradation Protection Assay was carried out using 750 ng of RNA encoding nanoluciferase in 3 forms: linear RNA without a 5' cap or 3' PolyA tail (negative control), linear RNA with 5' cap and 3' PolyA tail (canonical mRNA), and circularized RNA. Each sample was incubated in water or 1% FBS for 0, 0.5, 1, 2, 4, or 8 hours at room temperature. Afterwards all samples were run on a 1% agarose gel for 35 minutes at 100 V.

Example 4: Circularized Measuring Translation Efficiency and RNA Stability

RNA constructs encoding nanoluciferase complexed with Lipofectamine® 2000 (Life Technologies, #11668) and transfected into Hep3B cells (human hepatocyte cell line) seeded at 10,000 cells/well in a 96-well plate. Protein expression kinetics were measured using the Nano-Glo Luciferase Assay System (Promega, #N1110) using samples taken at 24, 48, and 72 hours post-transfection.

To measure RNA stability, qPCR was carried out using samples derived from cells that had been transfected as described above. cDNA was synthesized at each time point using the Power SYBR® Green Cells-to-Ct Kit (Life Technologies, #4402954) according to the manufacturer's instruction. The housekeeping gene β-actin was used to normalize the results.

Example 5: Improvements to Existing Methodology for RNA Circularization

Enzymatic Circularization Produces the Highest Levels of Circularized Product Using Existing Protocols.

400, 500, and 600 nucleotide (NT) RNA were circularized using 3 previously established methods: enzymatic (Perreault, 1995), splint-mediated (Moore and Sharp, 1992), and self-splicing (Puttaraju, 1992). Circularized products were run on a TBE-Urea 5% polyacrylamide gel for 3 hours at 180 V (FIG. 1). Non-circularized RNA was run as a control. No circularized product was detected using the self-splicing method (data not shown). The data shows that use of a ligase, preferably T4 RNA ligase, efficiently generates circularized RNA.

RppH Treatment Yields the Highest Level of Circularized Product Compared to Other Monophosphate-Generating Enzymes.

Figures 2A, 2B:
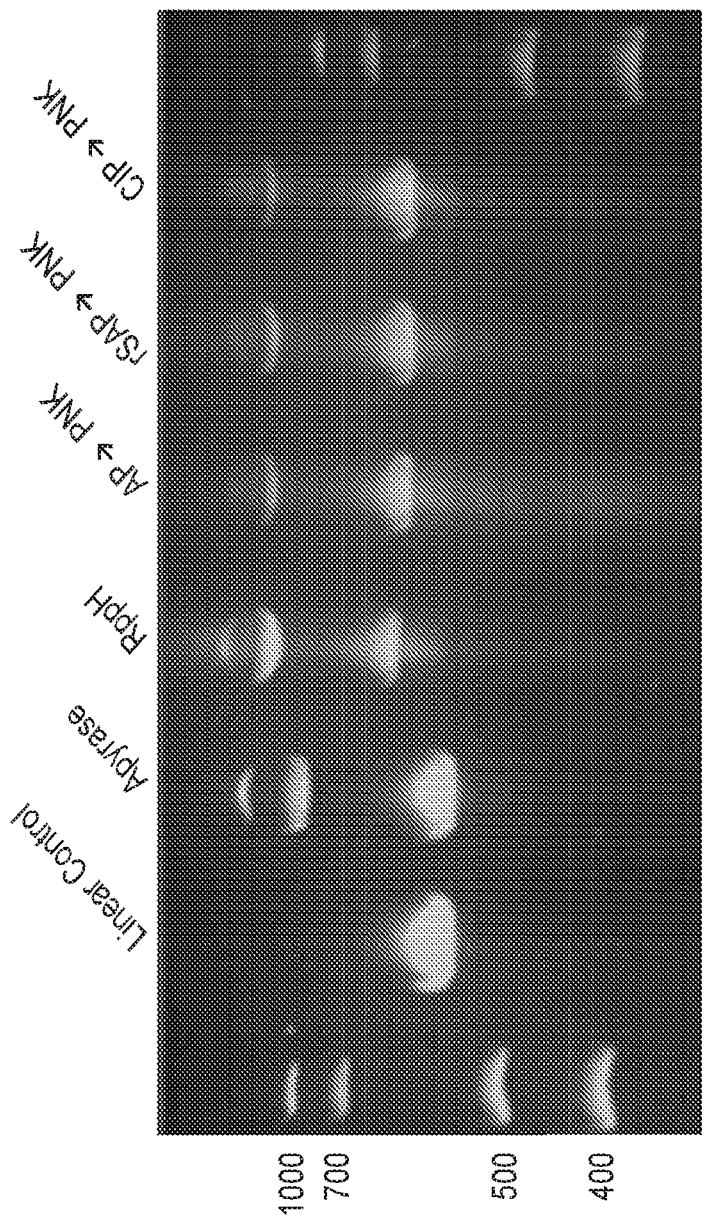
FIGS. 2A and 2B include a gel and a table showing that RNA 5' Pyrophosphohydrolase (RppH) treatment yields the highest level of circularized product compared to other monophosphate-generating enzymes.

Circularization protocol was carried out using a 500 nucleotide (NT)-long template with the only variation being the enzyme(s) used to generate the monophosphate 5' end necessary for T4 RNA Ligase-mediated circularization to occur. RNA 5' Pyrophosphohydrolase (RppH) and apyrase carry out this reaction in a single step. Alternatively, a two-step reaction can be carried out in which a phosphatase is first used to removal all 3 phosphates on the 5' end of the RNA molecule, followed by a second reaction in which a kinase adds a single phosphate back to the molecule. Final circularized products were denatured and then run on a TBE-Urea 5% polyacrylamide gel for 3 hours at 180 V (FIG. 2A). Approximate percentage of circularized product for each construct was determined by quantifying band intensities using Image J software analysis (FIG. 2B). The monophosphate enzyme that corresponded to the highest level of circularized product was chosen as the most efficient monophosphate enzyme. AP=Antarctic Phosphatase, rSAP=recombinant Shrimp Alkaline Phosphatase, CIP=Calf Intestinal Phosphatase, PNK=Polynucleotide Kinase. The data shows that RppH efficiently generates monophosphate RNA.

RppH is the Most Efficient Monophosphate-Generating Enzyme.

Figure 3A:
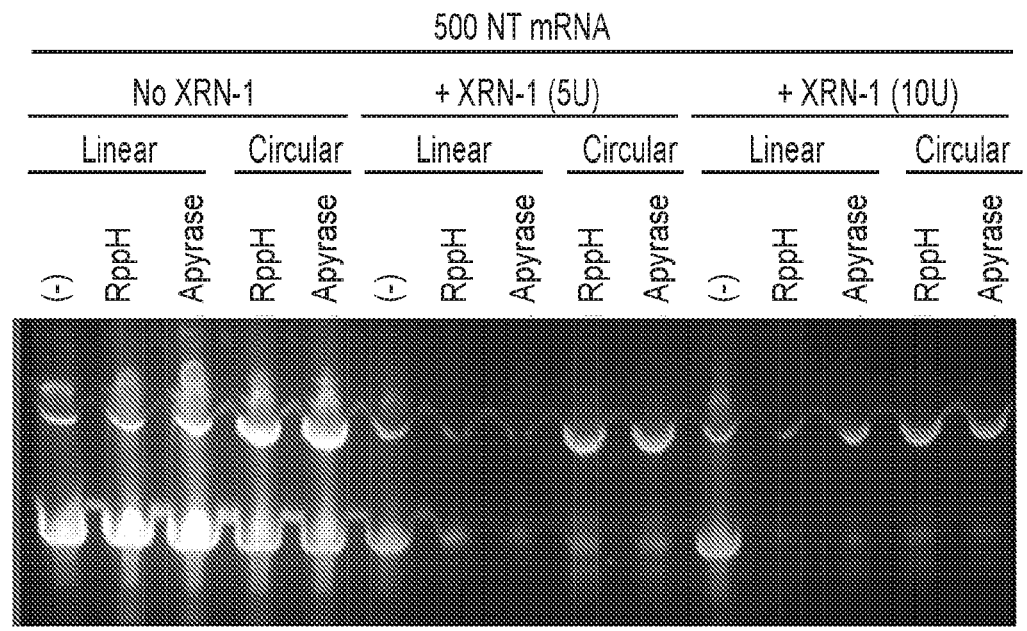
FIGS. 3A and 3B include gel showing that RppH is the most efficient monophosphate-generating enzyme.
Figure 3B:
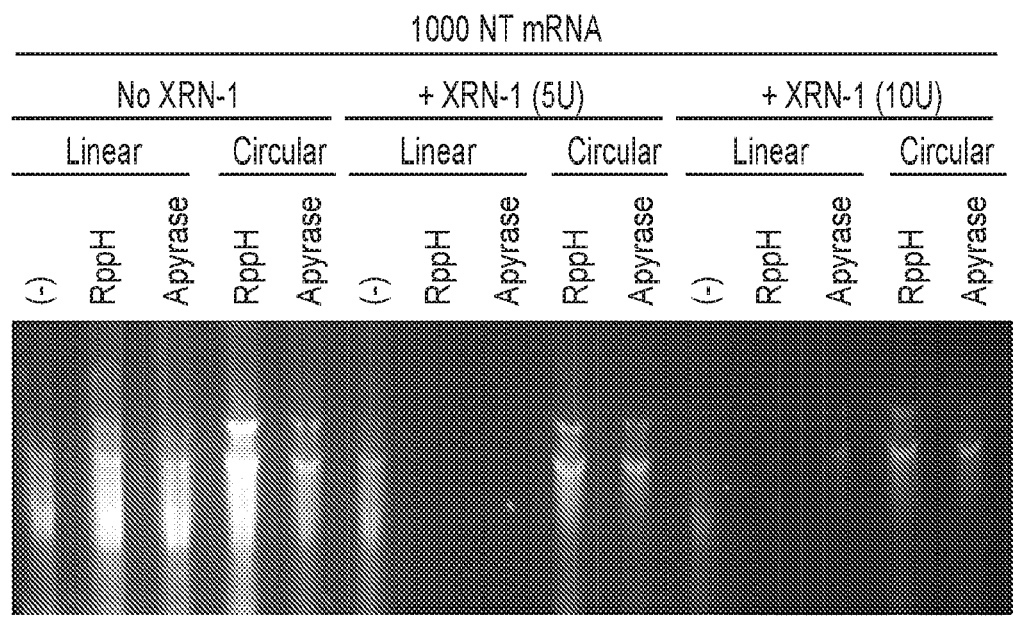

500 nucleotide (NT) RNA (FIG. 3A) or 1000 NT RNA (FIG. 3B) treated with the RppH or Apyrase monophosphate-generating enzyme were circularized and then exposed to XRN-1, an exonuclease that digests only linear RNA with a monophosphate 5' end. XRN-1 cannot degrade RNA with a triphosphate 5' end (post-in vitro transcription linear RNA). Final products were denatured and then run on a TBE-Urea 5% polyacrylamide gel for 3 hours (FIG. 3A) or 4 hours (FIG. 3B) at 180 V. Remnant bands present in the apyrase-treated constructs indicate that this enzyme reaction does not go to completion. RppH produces much fainter or a complete lack of bands indicating that almost, if not all, molecules are modified by this enzyme. The data show that, among the tested enzymes, RppH is the most efficient enzyme for generating monophosphate RNA.

Performing Multiple Rounds of Ligase Reaction Increases the Yield of Circularized Product.

Figure 4B:
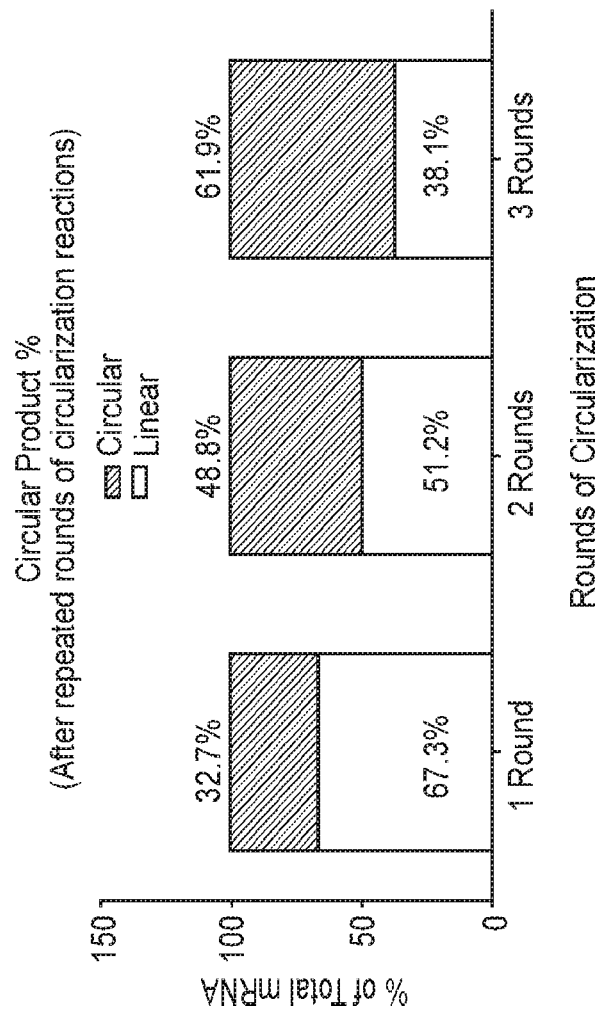
FIGS. 4A and 4B include a gel and a table showing that performing multiple rounds of ligase reaction increases the yield of circularized product.
Figure 4A:
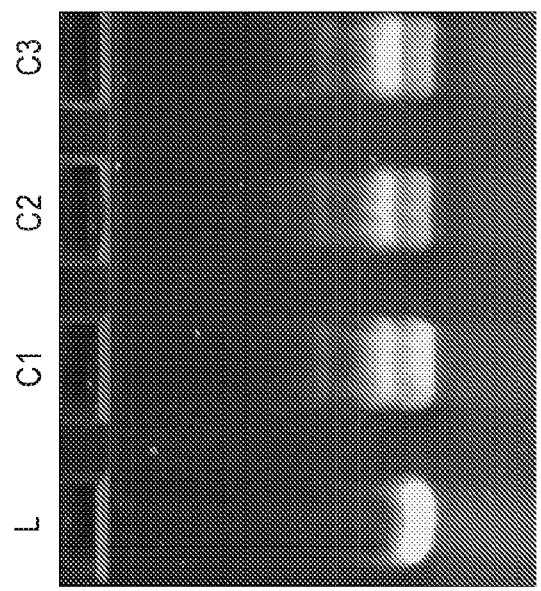
Figure 5B:
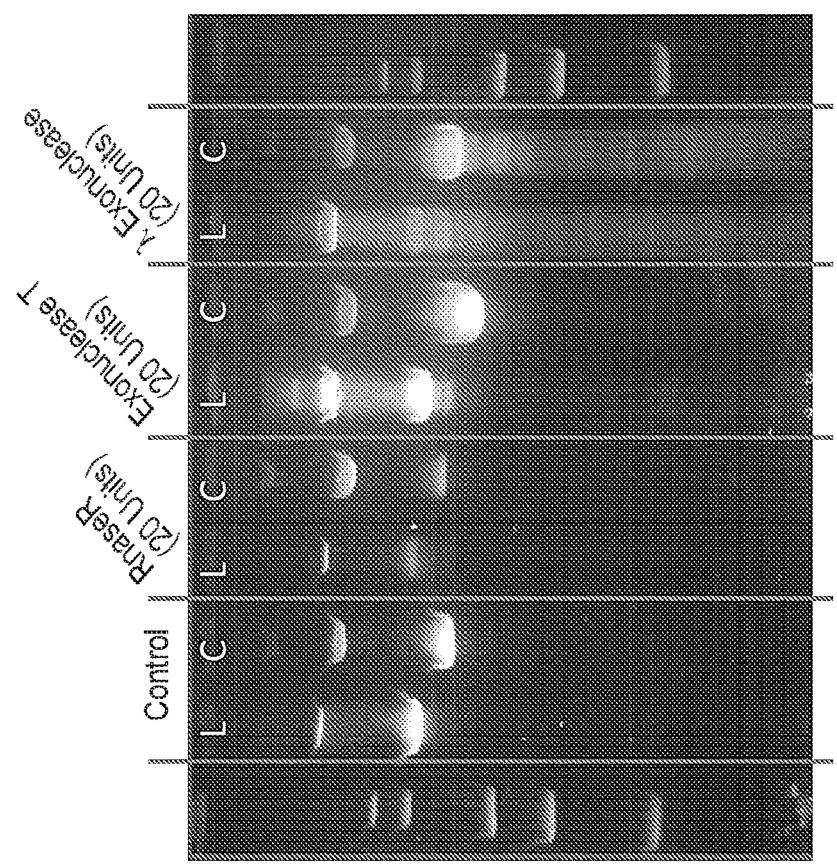
FIGS. 5A and 5B include gels showing that RNase R and XRN-1 exonucleases result in the highest purity of circularized product.
Figure 5A:
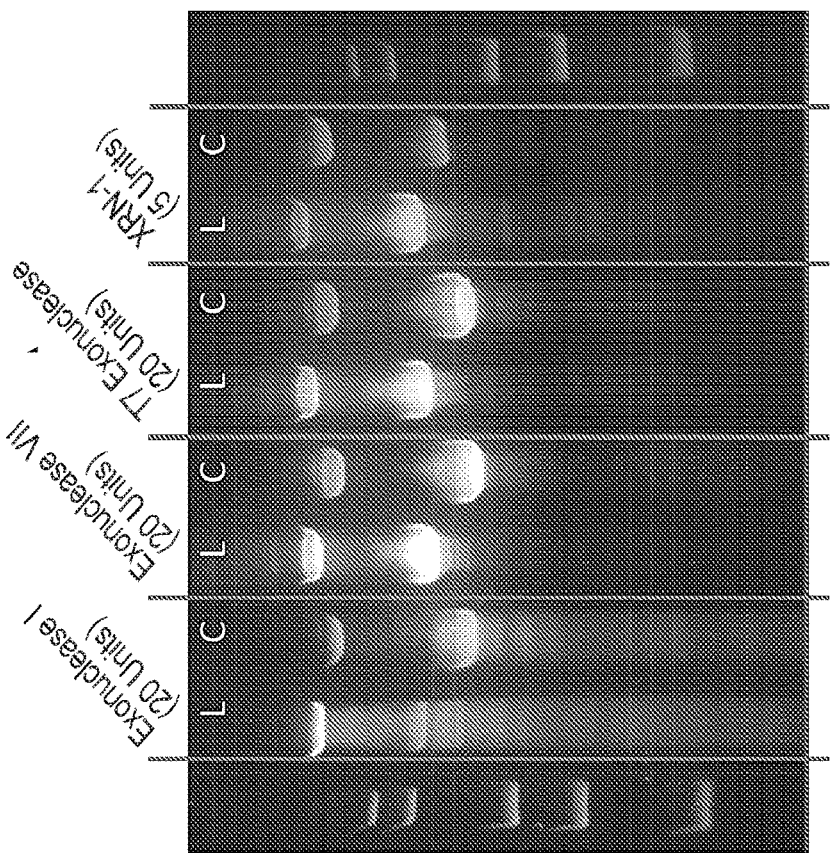

500 NT-long, circularized RNA was generated following the above-described protocol. After the initial circularization reaction was completed, circularized RNA was purified (Thermo, Genejet RNA Cleanup Kit) and used as template for two additional circularization reactions. After each round, 1 µg of RNA was set aside for further analysis. 1 µg of RNA from each round of circularization (rounds 1, 2, and 3, respectively, C1, C2, and C3) was run on a 2% E-gel (Invitrogen) along with non-circularized linear (L) control (FIG. 4A). The approximate percentage of circularized product for each construct was determined by quantifying band intensities using Image J software analysis (FIG. 4B). The data show that performing multiple rounds of ligase reaction increase the yield of circularized products.

RNase R and XRN-1 Exonucleases Result in the Highest Purity of Circularized Product.

5 µg of linear or circularized 500 NT-long RNA constructs were incubated for 1 hour with one of the indicated exonucleases. After exonuclease digestion, samples were denatured and run on a TBE-Urea 5% polyacrylamide gel for 3 hours at 180 V. RNase R and XRN-1 resulted in noticeable removal of linear RNA, although neither resulted in complete removal of residual linear RNA. The data show that use of RNase R and/or XRN-1 efficiently degrades linear RNA and thereby enriches for circularized RNA.

Example 6: Inclusion of CRC Sequences Enhances Efficiency of RNA Circularization Inclusion of CRC Sequences Enhances Efficiency of Circularization of RNA Constructs 300 NT to 500 NT in Length.

RNA molecules 300 NT, 400 NT, or 500 NT in length were generated with (+) or without (−) a 20-NT complement-reverse complement (CRC) sequence flanking the 5' and 3' ends of the molecule. Predicted secondary structures were generated using RNAFold software (FIG. 6A). Arrows point to the predicted orientation of the 5' and 3' ends of the RNA molecule. Top row of boxes=no CRC; bottom row of boxes=with CRC. All constructs underwent circularization reactions, were denatured, and were then run on a TBE-Urea 5% polyacrylamide gel for 3 hours at 180 V (FIG. 6B). The approximate percentage of circularized product for each construct was determined by quantifying band intensities using Image J software analysis (FIG. 6C). The data show that inclusion of CRC sequences enhances efficiency of RNA circularization.

RNA Up to 1000 NT in Length can be Circularized when CRC Sequences are Included in the RNA Molecule.

RNA molecules 600 NT, 700 NT, 800 NT, 900 NT, or 1000 NT in length were generated with (+) or without (−) a 20-NT complement-reverse complement (CRC) sequence flanking the 5' and 3' ends of the molecule. Predicted secondary structures were generated using RNAFold software (FIG. 7A). Arrows point to the predicted orientation of the 5' and 3' ends of the RNA molecule. Top row of boxes=no CRC; bottom row of boxes=with CRC. All constructs underwent circularization reactions, were denatured, and were then run on a TBE-Urea 5% polyacrylamide gel for 4 hours at 180 V (FIG. 7B). Circularized RNA products migrate slower on the gel (arrows pointing downwards). The arrows pointing upwards point to non-circularized, linear product. The approximate percentage of circularized product for each construct was determined by quantifying band intensities using Image J software analysis (FIG. 7C). Graphical representation of circularized product from PAGE gels illustrated in FIGS. 6 and 7 are shown in FIG. 7D. The data show that inclusion of CRC sequences enhances efficiency of RNA circularization for long RNA molecules.

Inclusion of CRC Sequences Enhances Efficiency of Circularization of RNA Constructs Up to at Least 3000 NT in Length.

Circularized RNA constructs of the indicated sizes (FIG. 8, Column A) were generated and subsequently digested with XRN-1. Since linear and circularized bands from RNA over 1000 NT cannot be adequately separated on denaturing polyacrylamide gel, the amount of circularized product was determined by first digesting the RNA with XRN-1. RNA concentrations pre- and post-XRN-1 digestion were determined via NanoDrop spectrophotometer. [(Remaining RNA post-XRN1)/(total starting RNA)×100] was used to calculate circularization efficiency. As a control, linear forms of each RNA construct, all containing triphosphate ends, were treated with XRN-1 to confirm the specificity of this enzyme, since XRN-1 cannot degrade RNA comprising a triphosphate 5' end (Column B). To determine the efficiency with which XRN-1 removes linear RNA, monophosphate-treated linear forms of each RNA molecule were treated with XRN-1 (Column C). The average leftover product was ~25%. This number was taken into account when determining the final circularization efficiency of each construct tested by first subtracting 25% from the remaining, post-XRN-1 RNA (Column D). The data show that inclusion of CRC sequences to enhance efficiency of RNA circularization and, in particular, for long RNA molecules.

Circularization Efficiency is Dependent Upon the 5' and 3' End-Positions of RNA Molecules.

Figure 9A:
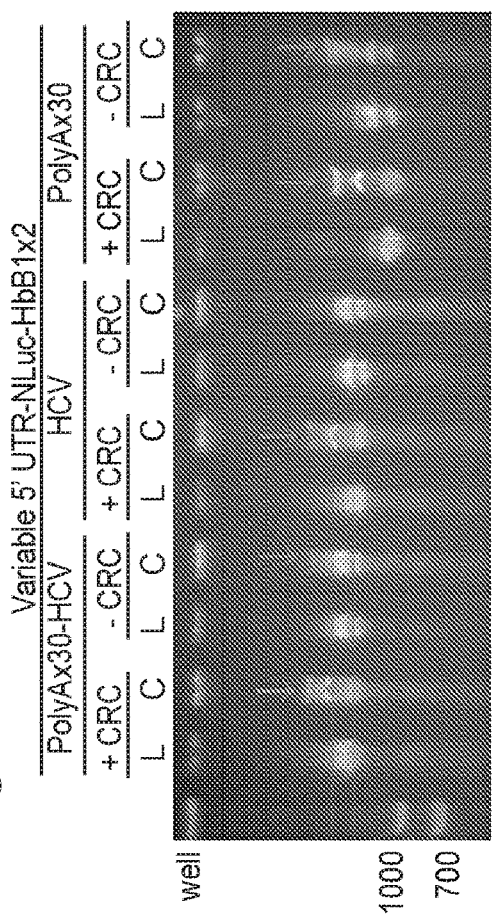
FIGS. 9A to 9C include predicted secondary structures and gels showing that circularization efficiency is dependent on the 5' and 3' end positions of RNA molecules.
Figure 9B:
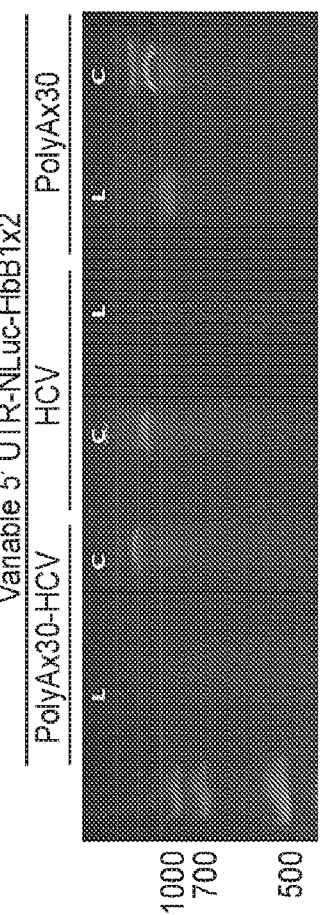
Figure 9C:
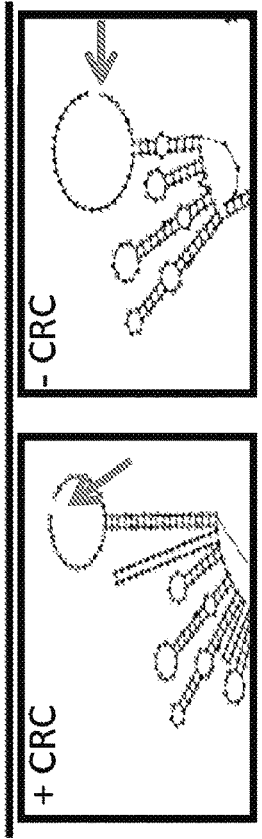

Circularized or linear RNA encoding the nanoluciferase reporter protein, flanked by a polyAx30 motif, HCV IRES, or PolyAx30-HCV IRES (5' UTR) and a twice-repeated end sequence of the β-globin gene (3' UTR) were generating with (+) or without (−) a 20-NT complement-reverse complement (CRC) sequence flanking the 5' and 3' ends of the molecule. Predicted secondary structures were generated using RNAFold software (FIG. 9A). Arrows point to the predicted orientation of the 5' and 3' ends of the RNA molecule. Left column of boxes=with CRC; right column of boxes=no CRC. Constructs were denatured and run on a TBE-Urea 5% polyacrylamide gel for 4 hours at 180V (FIG. 9B). CRC+ RNA constructs in either linear or circularized form were digested with RNase R, an exonuclease that targets free 3' ends of linear RNA (FIG. 9C). L=Linear. C=Circular. Arrows pointing downwards point to bands that represent circularized RNA. The presence of circularized product without a CRC sequence in the PolyA-containing RNA molecules and lack of circularized product in the HCV only RNA molecules evidences the importance of end position on circularization efficiency. This point is emphasized by the presence of circularized product in HCV-only RNA molecules when a CRC sequence is added and the increase in total circularized RNA when a CRC sequence is added to a PolyA-containing RNA molecule. Again, the data show that inclusion of CRC sequences enhances efficiency of RNA circularization, particularly among RNA molecules whose termini are not readily accessible to ligase.

Inclusion of CRC Sequences Results in Robust and Rapidly-Produced Levels of Circularized Product.

500 NT-long RNA molecules derived from the NLuc coding sequence (CDS) was incubated in circularization reactions for 0, 2, 4, 6, 8, 16, or 24 hours. Products were purified, denatured, and run on a TBE-Urea 5% polyacrylamide gel for 3 hours at 180 V (FIG. 10A). X=linear product not exposed to T4 RNA ligase. Top arrows point to bands that represent circularized RNA; bottom arrows point to bands that represent non-circularized, linear RNA. Approximate percentage of circularized product for each construct was determined by quantifying band intensities using Image J software analysis (FIG. 10B). The same circularization incubation times were carried out using a 1000 NT-long RNA molecule template. These constructs were run for 5 hours on the 5% polyacrylamide gel in order to see distinguishable separation of circularized and linear RNA (FIG. 10C). This extended run time resulted in warping of the RNA that made quantifying the percentage of circularized RNA impossible. Top arrows point to bands that represent circularized RNA; bottom arrows point to bands that represent non-circularized, linear RNA. Again, the data show that inclusion of CRC sequences enhances efficiency of RNA circularization Circularized RNA Constructs Containing a Longer CRC and Shorter Random NT Motif have the Highest Levels of Circularization Efficiency.

A panel of circularized RNA constructs encoding nanoluciferase that differed only in the length and composition of their CRC and random NT motifs were generated to test the effect that these motifs have on circularization efficiency. Diagram depicting the orientation of the CRC and random NT motifs and the predicted secondary structure these motifs confer when included in an RNA sequence (FIG. 11A). In total, 31 circularized RNA constructs with varying CRC and random NT motifs were generated, denatured, and run on a TBE-Urea 5% polyacrylamide gel for 3 hours at 180 V (FIG. 11B). Approximate percentage of circularized product for each construct was determined by quantifying band intensities using Image J software analysis (FIG. 11C). OG=original CRC/Random NT motif used in all other experiments (20 NT-long CRC, 10 NT-long random NT). A=indicates that the random motif is comprised entirely of a polyA sequence instead of a heterogeneous sequence of nucleotides. The data show that longer CRC and shorter random nucleotide overhangs yield more circularized product.

Shorter CRC Results in Higher Translation Efficiency of Circularized RNA.

Figure 12:
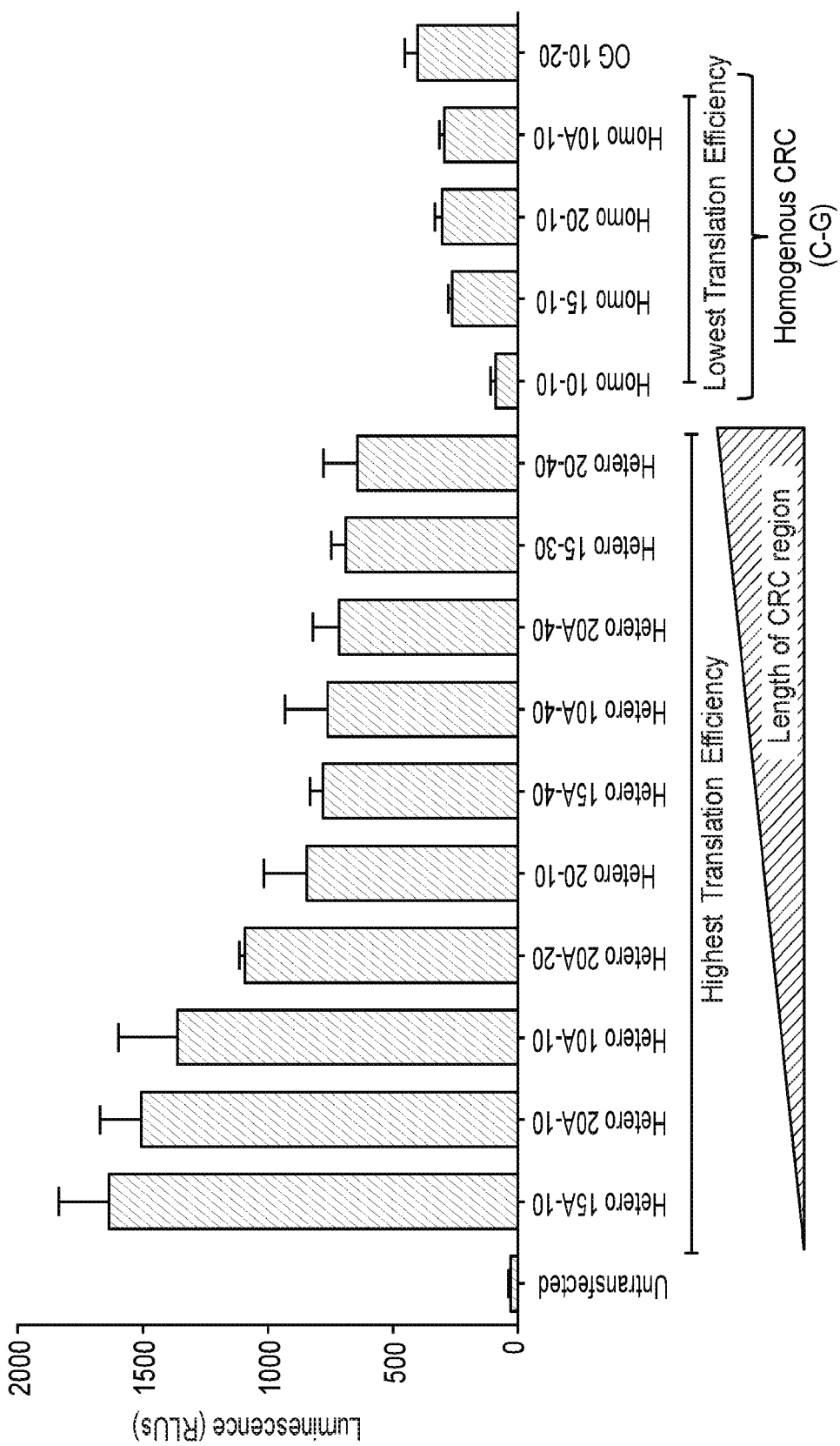
FIG. 12 includes a graph showing that shorter CRC results in higher translation efficiency of circularized RNA.

A panel of circularized RNA constructs encoding nanoluciferase that differed only in the length and composition of their CRC and random NT motifs were generated to test the effect that these motifs have on translation efficiency. Hep3B cells plated at 10,000 cells per well in a 96-well plate were transfected with each construct. Constructs were complexed to the transfection reagent Lipofectamine® 2000 (0.3 µL/well). Luciferase activity was measured 24 hours post transfection (FIG. 12). OG=original CRC/Random NT motif used in all other experiments (20 NT-long CRC, 10 NT-long random NT). A=indicates that the random motif is comprised entirely of a polyA sequence instead of a heterogeneous sequence of nucleotides. The data show that a shorter CRC confers enhanced translation efficiency of resulting circularized RNA.

Longer CRC Results in Higher IFN-β Response in Hep3Bs Transfected with Circularized RNA.

Figure 13:
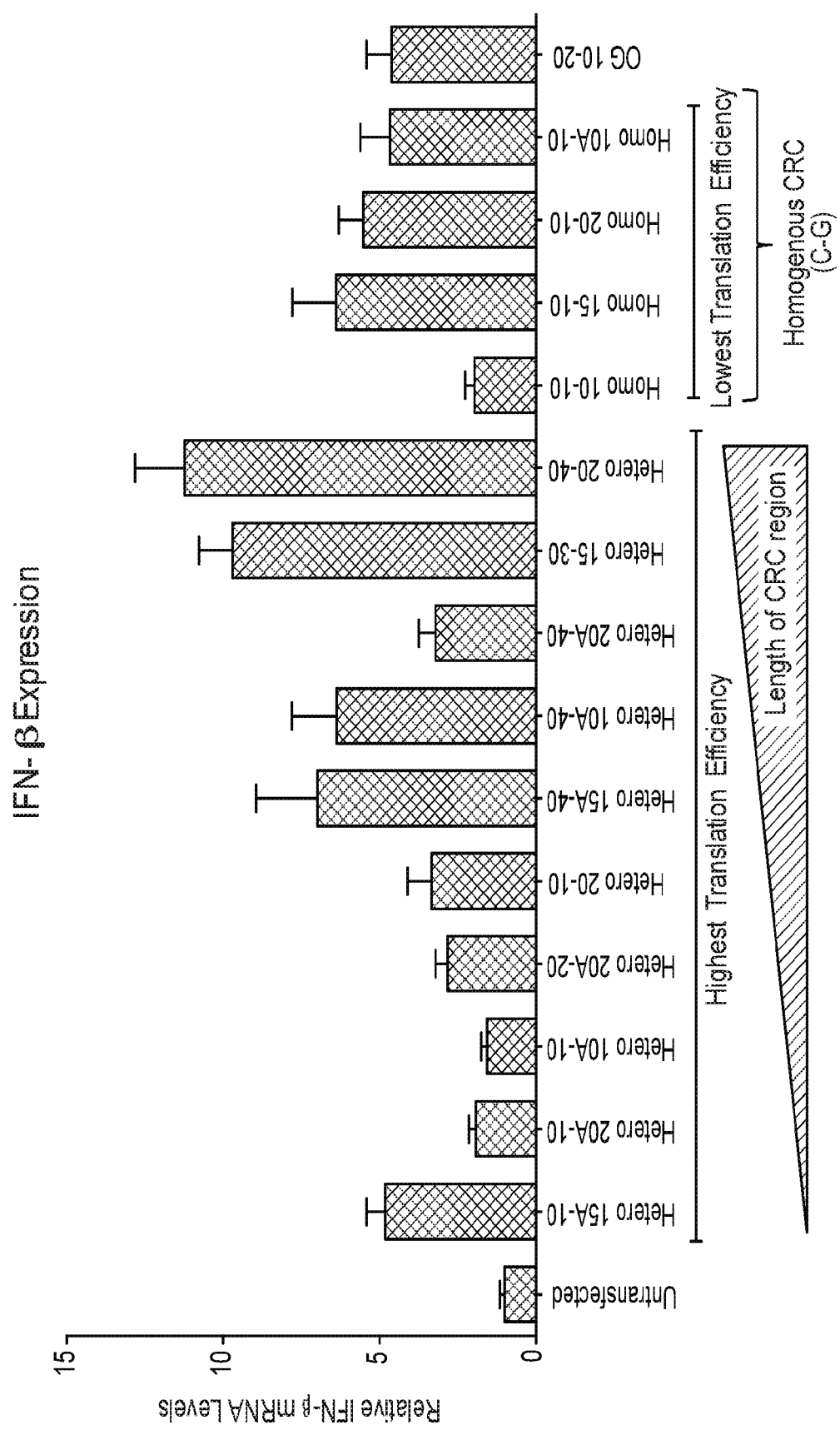
FIG. 13 includes a graph showing that longer CRC results in higher IFN-β response in Hep3Bs transfected with circularized RNA.

A panel of circularized RNA constructs encoding nanoluciferase that differed only in the length and composition of their CRC and random NT motifs were generated to test the effect that these motifs have their immunogenicity. Hep3B cells plated at 10,000 cells per well in a 96-well plate were transfected with each construct. Constructs were complexed to the transfection reagent Lipofectamine® 2000 (0.3 µL/well). IFN-β levels measured by qPCR (normalized to β-actin) 24 hours post transfection (FIG. 13). OG=original CRC/Random NT motif used in all other experiments (20 NT-long CRC, 10 NT-long random NT). A=indicates that the random motif is comprised entirely of a polyA sequence instead of a heterogeneous sequence of nucleotides. These data show that a shorter CRC lowers interferon response of resulting circularized RNA.

Example 7: Characterizing Translation Efficiency of Circularized RNA In Vitro

A 20-Mer Derived from the Elastin 3' UTR Motif Enhances Translation Efficiency of Linear and Circularized RNA.

Hep3B cells plated at 10,000 cells per well in a 96-well plate were transfected with 200 ng of linear or circularized RNA encoding the nanoluciferase protein. The transfection was performed using the transfection reagent Lipofectamine® 2000 (0.3 µL/well). The nanoluciferase coding sequence (CDS) was flanked by variable experimental 5' and 3' untranslated regions (UTRs). Luminescence levels were measured 24 hours post-transfection to determine differences in translation efficiency (FIG. 14). These data show that inclusion of at least one repeat of a 20-mer derived from the 3' UTR of elastin ("Elastin") in the circularized RNA construct increases translation efficiency.

The PPT19 (5' UTR) and Elastinx3 (3' UTR) Combination Sustain Protein Expression of Circularized RNA.

Figure 15:
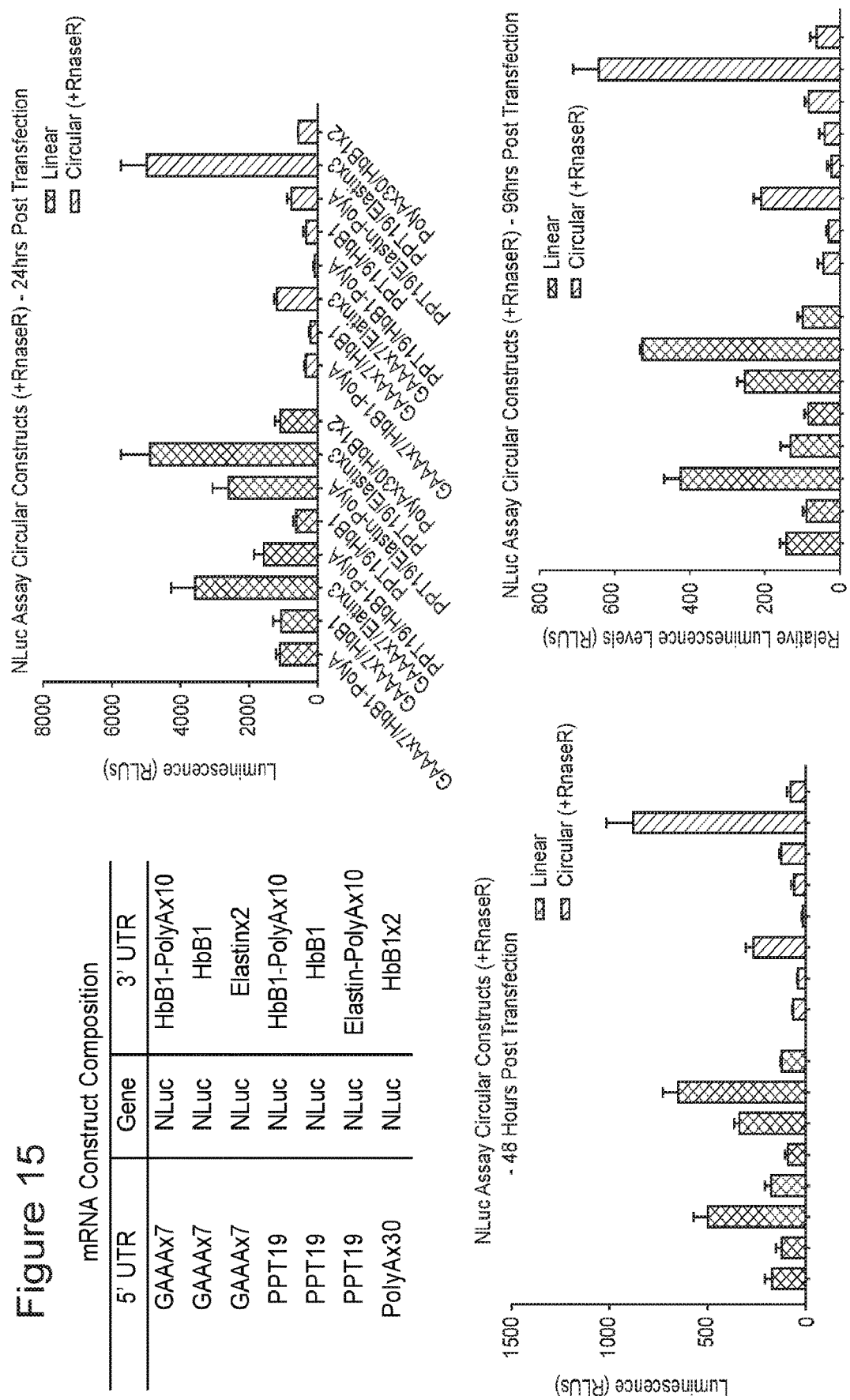
FIG. 15 includes graphs showing that the PPT19 (5' UTR) and Elastinx3 (3' UTR) combination sustain protein expression of circularized RNA.

Hep3B cells plated at 10,000 cells per well in a 96-well plate were transfected with 200 ng of linear or circularized RNA encoding the nanoluciferase protein complexed with the transfection reagent Lipofectamine 2000 (0.3 µL/well). The nanoluciferase coding sequence (CDS) was flanked by variable, experimental 5' and 3' untranslated regions (UTRs). Luminescence levels were measured 24, 48, and 96 hours post-transfection to determine differences in translation efficiency (FIG. 15). These data show that inclusion of the PPT19 sequence in a circularized RNA construct helps sustain protein expression.

A 20-Mer Elastin 3' UTR Motif, but not the HCV IRES (5' UTR) or HbB1 (3' UTR), Enhances Translation Efficiency of Circularized RNA.

Figure 16:
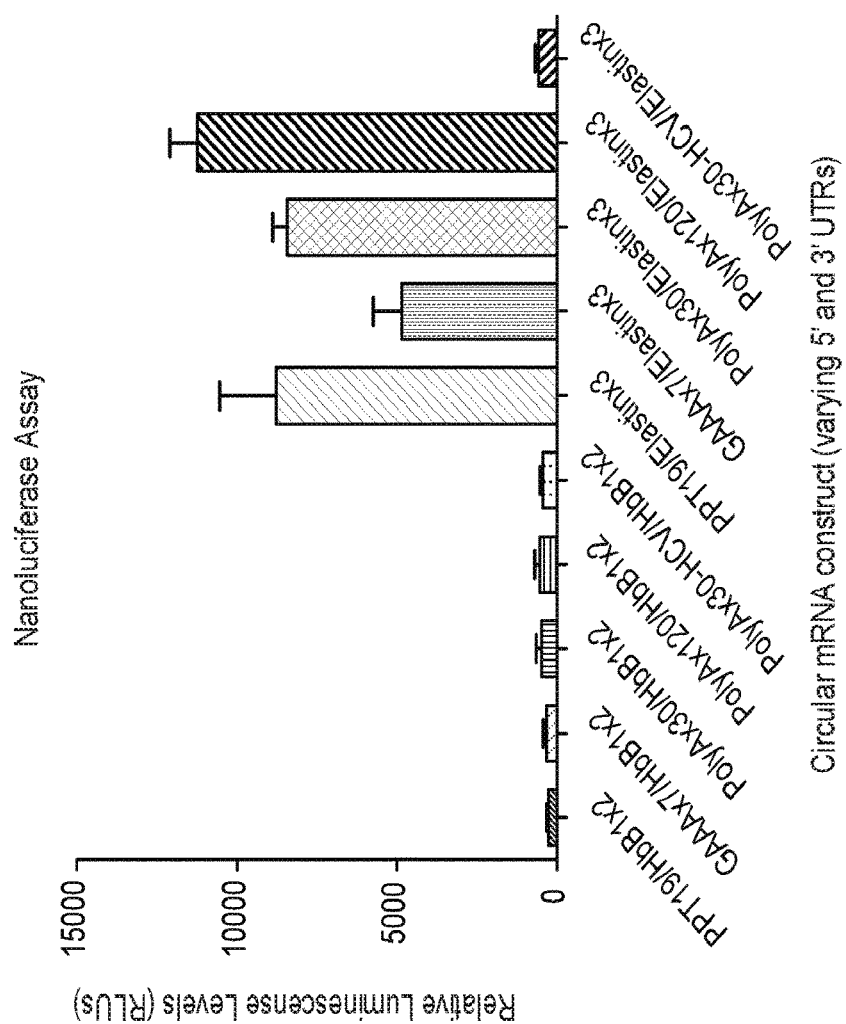
FIG. 16 includes a graph showing that a 20-mer elastin 3' UTR motif, but not the Hepatitis C Virus-derived (HCV) IRES (5' UTR) or HbB1 (3' UTR), enhances translation efficiency of circularized RNA.

Circularized RNA containing the nanoluciferase (NLuc) coding sequences flanked by experimental 5' and 3' UTRs were generated using the T7 High Yield RNA Synthesis Kit (NEB). Constructs were transfected into Hep3B cells and luminescence levels were measured 24 hours post-transfection to determine differences in translation efficiency (FIG. 16). Again, these data show that inclusion of at least one repeat of a 20-mer derived from the 3' UTR of elastin in the circularized RNA construct increases translation efficiency.

Circularized RNA Composed of 50% 5-Methyl Cytidine (5mC) Modified Nucleotides Confers High Levels of Translation.

Figure 17:
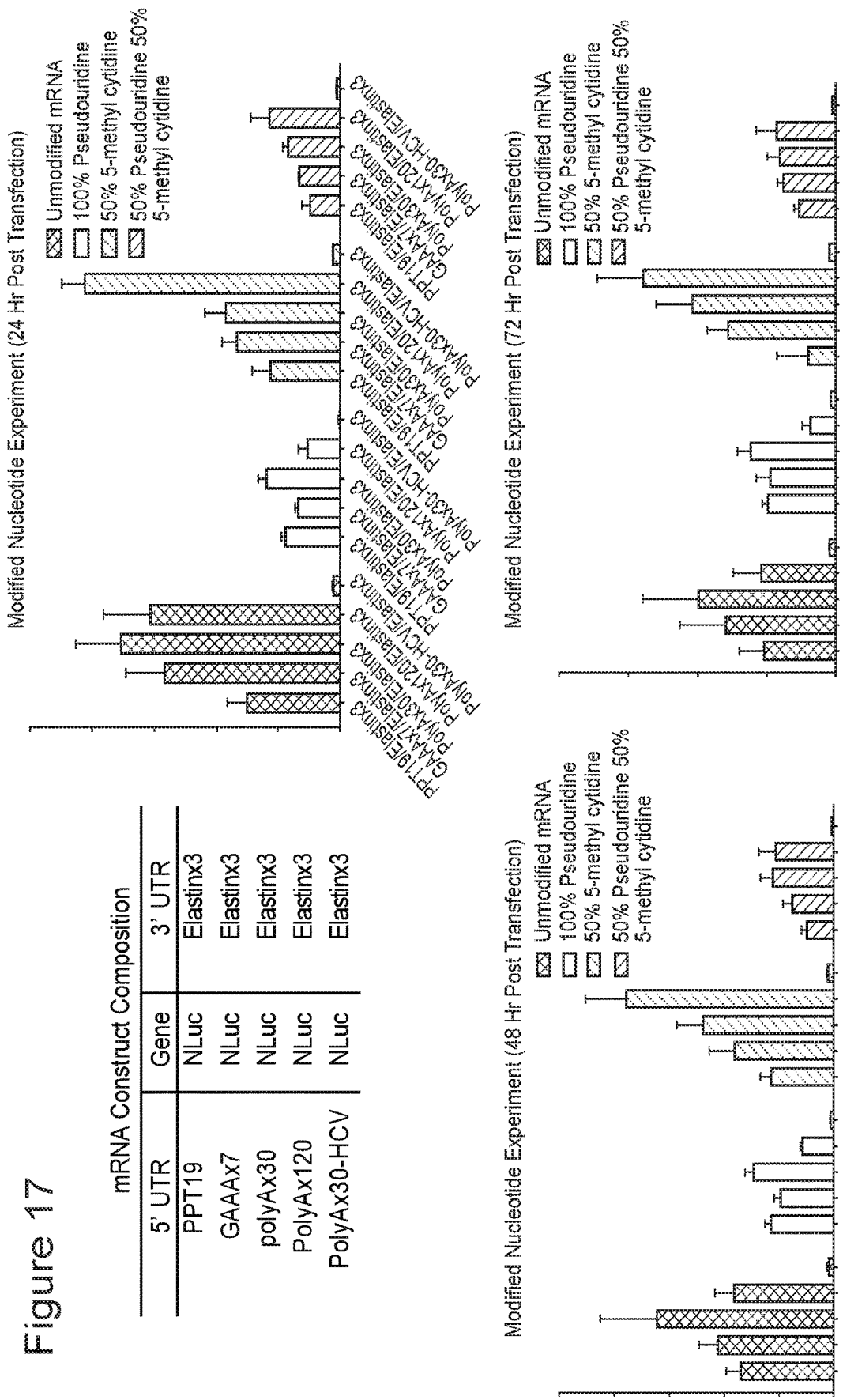
FIG. 17 includes graphs showing that circularized RNA composed of 50% 5-methyl cytidine (5mC)-modified nucleotides confers high levels of translation.

Circularized RNA containing the nanoluciferase (NLuc) coding sequences flanked by experimental 5' and 3' UTRs were generated using the T7 High Yield RNA Synthesis Kit (NEB). These in vitro transcription reactions where generating with either: 100% pseudouridine, 50% 5mC, or 50% pseudouridine and 50% 5mC. Constructs were transfected into Hep3B cells and luminescence levels were measured 24 hours post-transfection to determine differences in translation efficiency (FIG. 17). These data show that inclusion of modified nucleotides, such as 50% 5-methyl cytidine, improves translation efficiency.

Modified Nucleotide Panel Reveals that 50% 5mC Composition Provides the Highest Level of Translation Efficiency to Circularized RNA.

Figure 18:
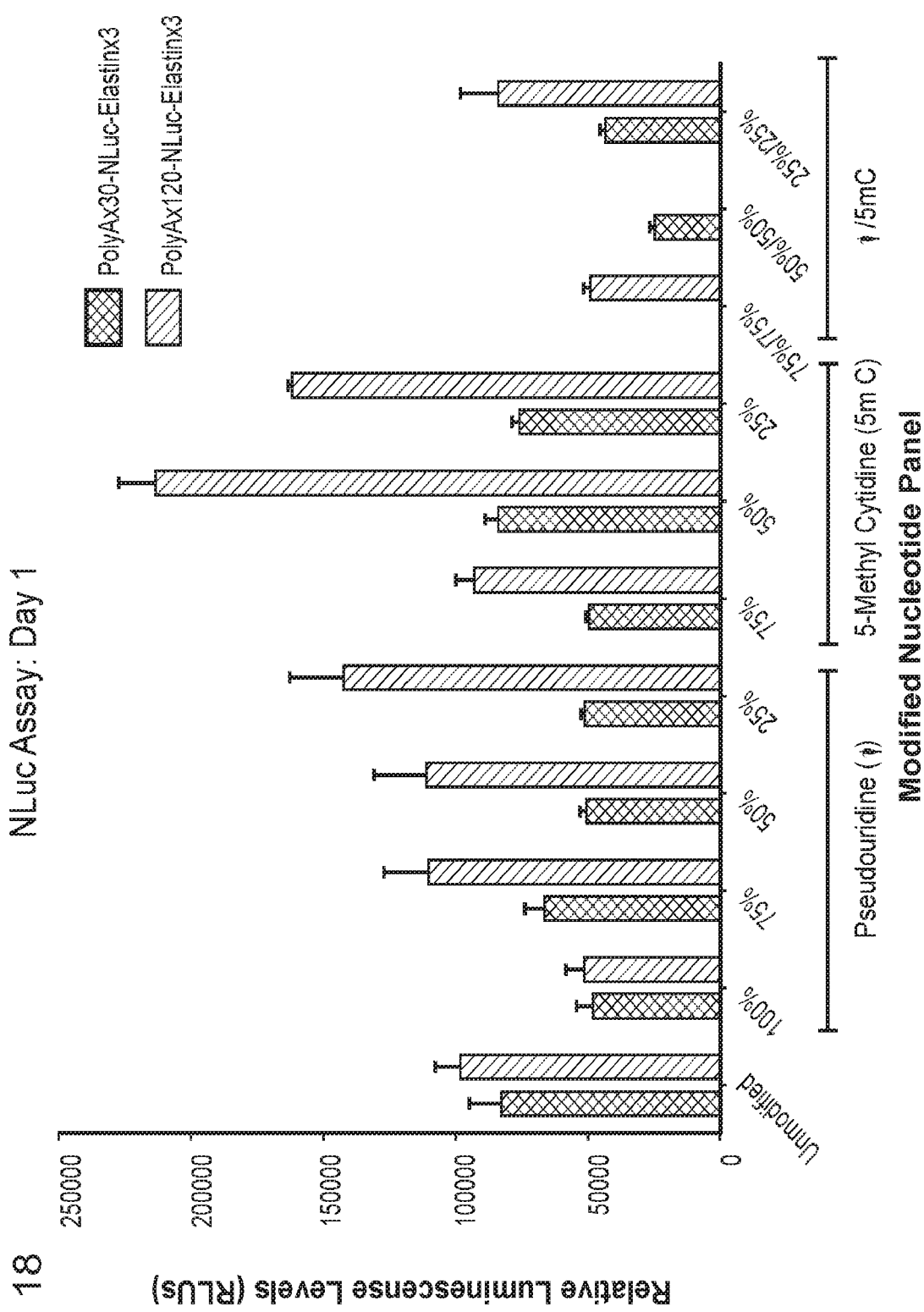
FIG. 18 includes graphs showing that a modified nucleotide panel reveals that 50% 5mC composition provides the highest level of translation efficiency to circularized RNA.
Figure 18:
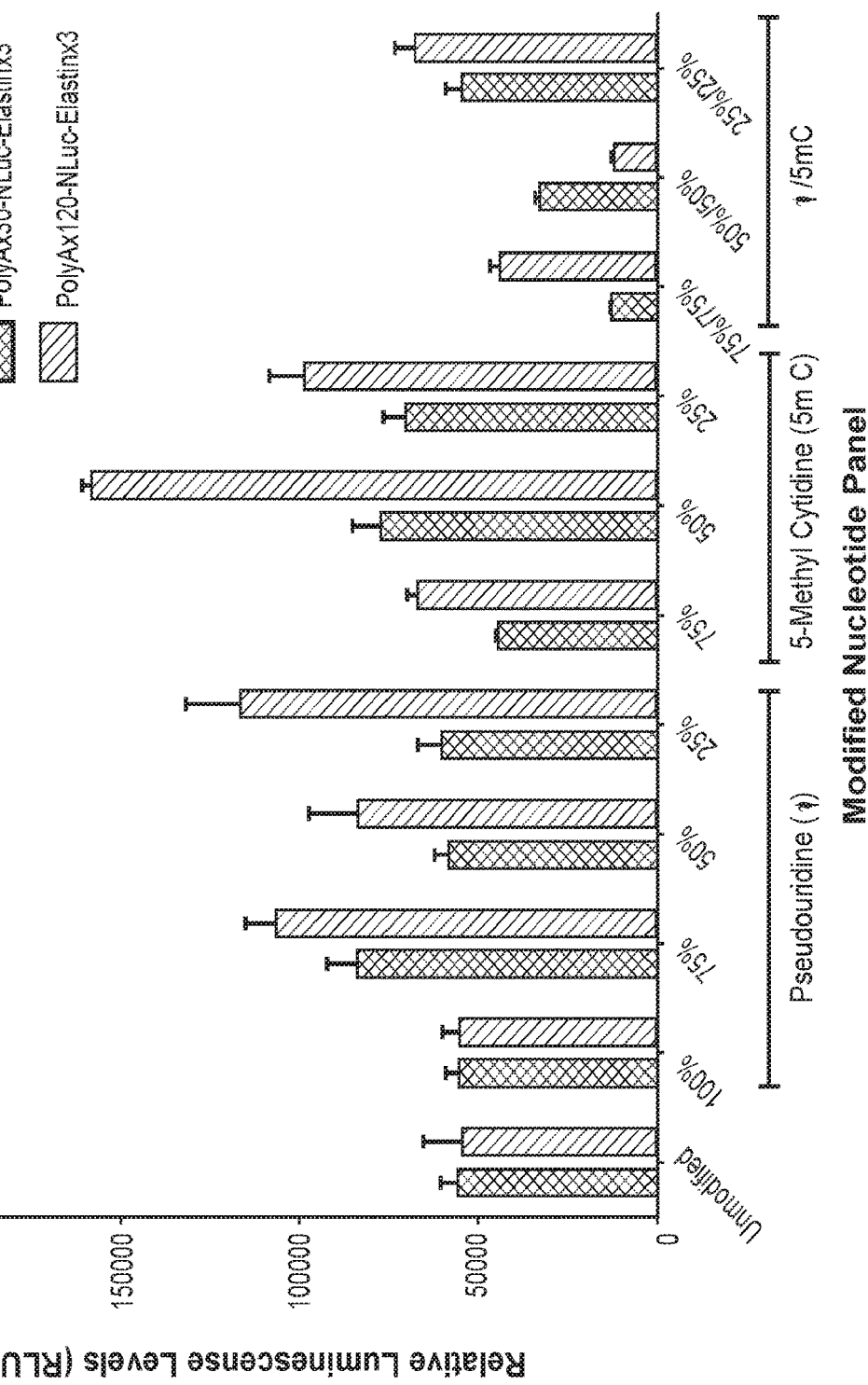
Figure 18:
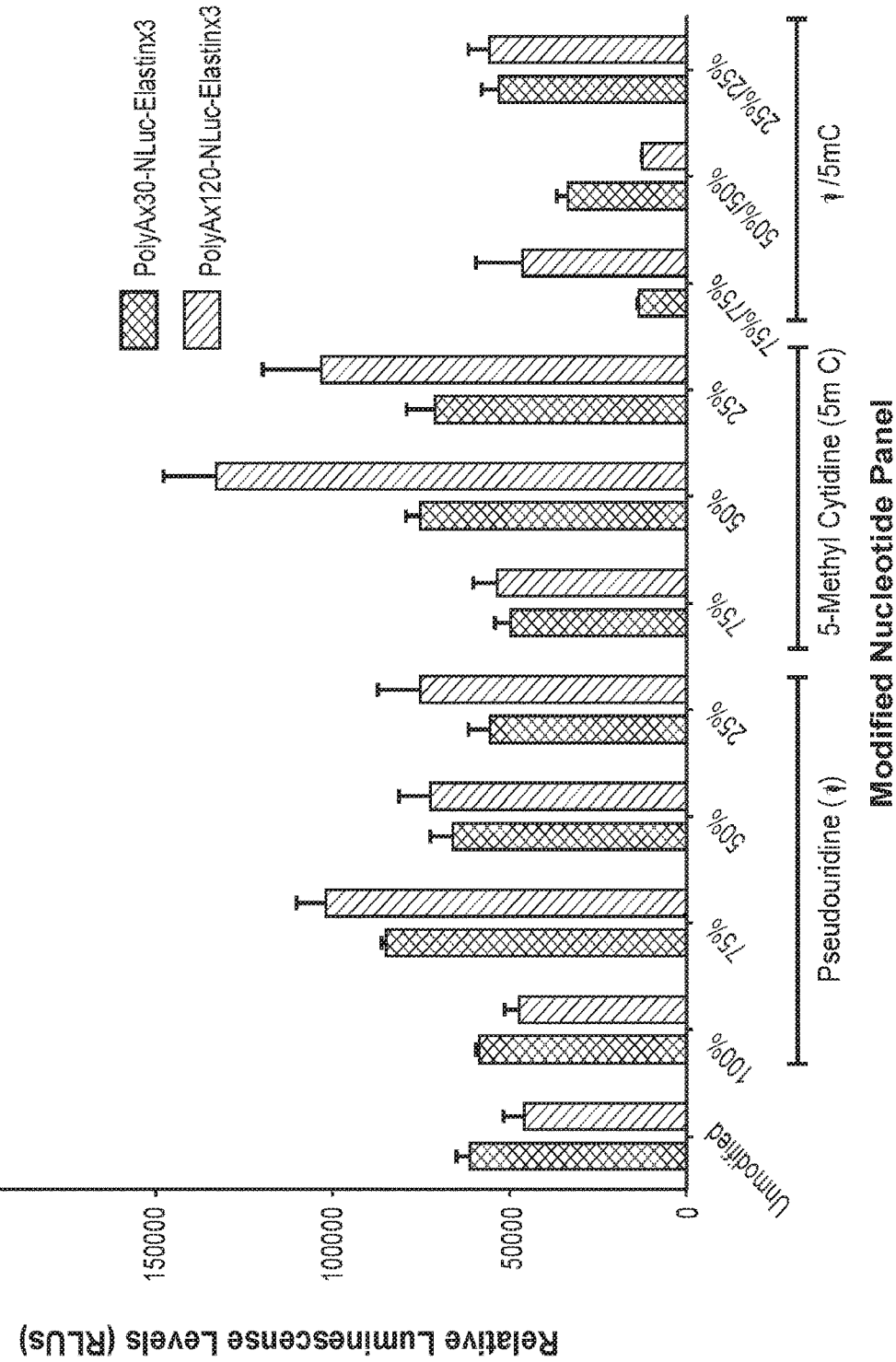

Circularized RNA encoding the nanoluciferase (NLuc) coding sequences flanked by experimental 5' and 3' UTRs were generated using the T7 High Yield RNA Synthesis Kit (NEB). Constructs were generated with the indicated modified nucleotide compositions. Constructs were transfected into Hep3B cells and luminescence levels were measured 24, 48, and 72 hours post-transfection to determine differences in translation efficiency (FIG. 18). Again, these data show that inclusion of modified nucleotides, such as 50% 5-methyl cytidine, improves translation efficiency.

EMCV IRES Confers the Greatest Translation Efficiency in Human Cells to Circularized RNA but not to Capped/Tailed Linear RNA.

Figure 19:
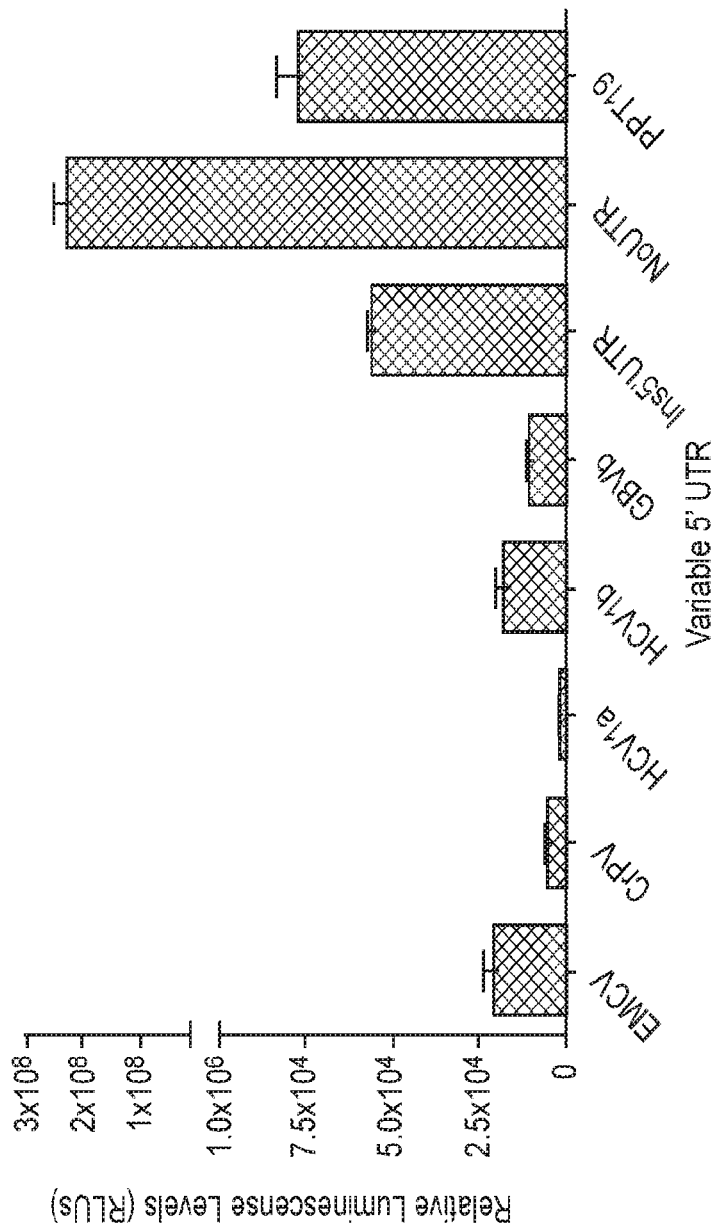
FIG. 19 includes graphs showing that encephalomyocarditis virus (EMCV) IRES confers the greatest translation efficiency to circularized RNA but not to capped/tailed linear RNA.
Figure 19:
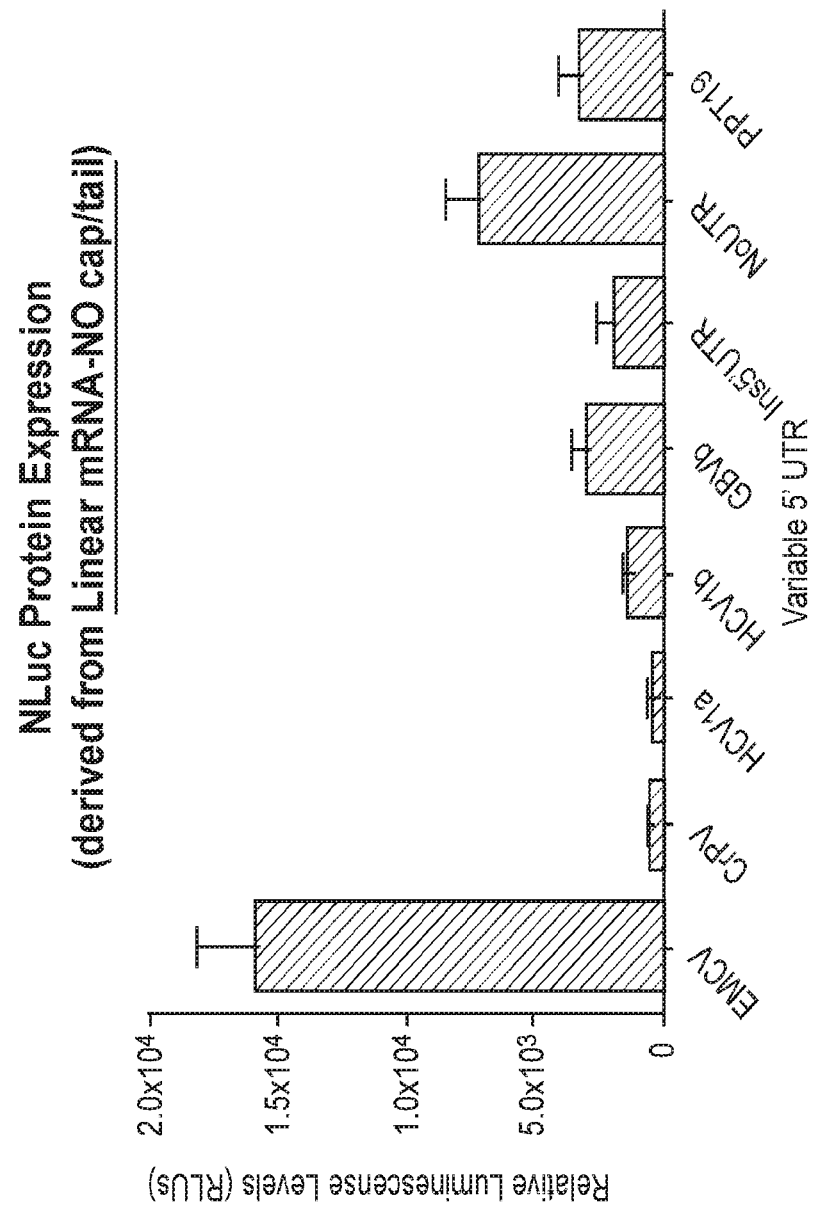
Figure 19:
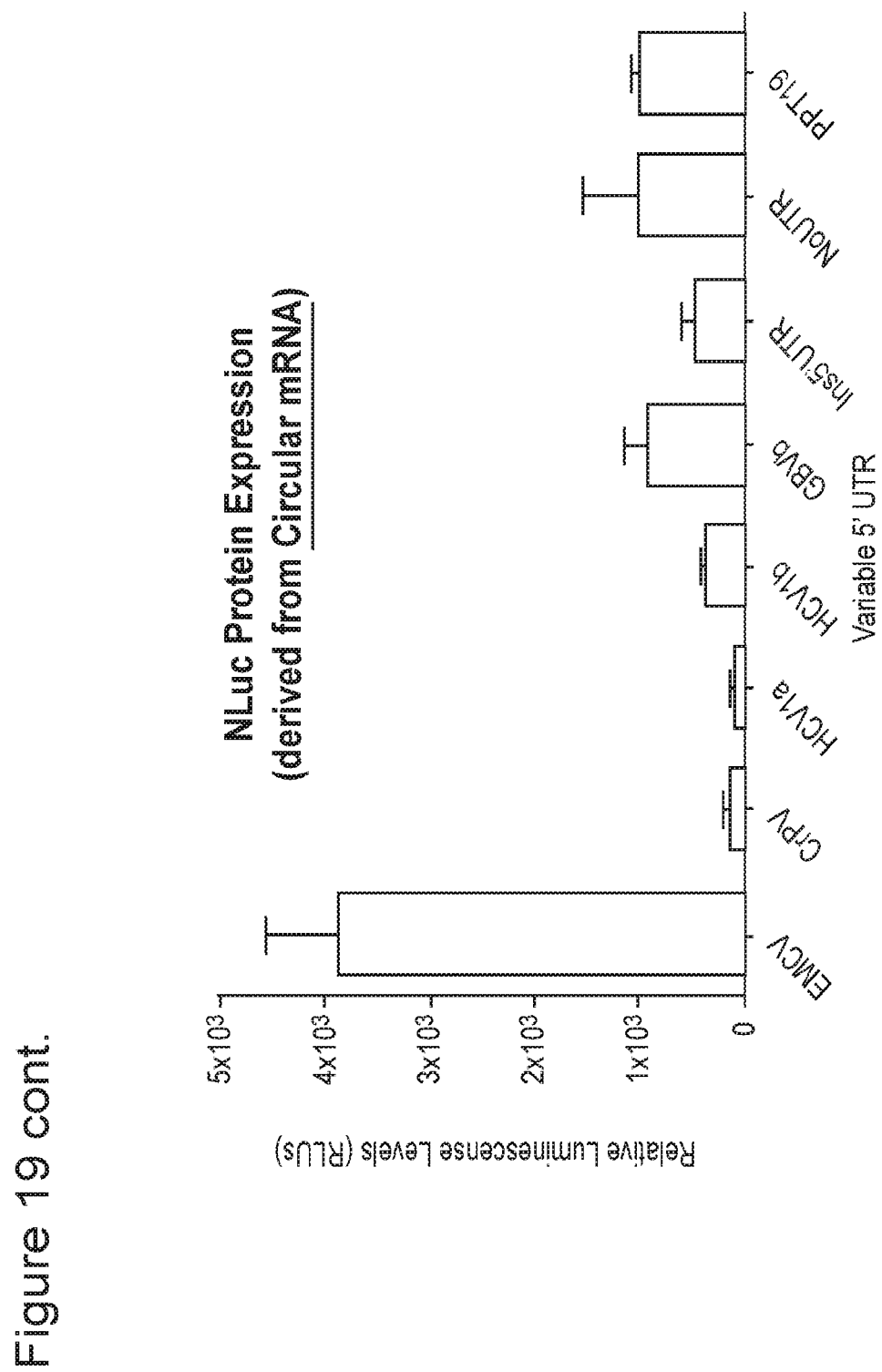

A panel of NLuc-encoded RNA varying in their 5' UTR containing experimentally verified IRES (World Wide Web at iresite.org) were transfected into Hep3B cells, and luminescence levels were measured 24 hours post-transfection to determine differences in translation efficiency. Three forms of RNA were transfected into Hep3Bs: canonical mRNA (containing a 5' cap and polyA tail), unstable RNA (no cap or tail), or circularized RNA (FIG. 19). These data show that inclusion of EMCV IRES in the circularized RNA construct increases translation efficiency.

Spiking with a Competitive Cap Analog Confirms that Translation of Circularized RNA is Cap-Independent.

Figure 20:
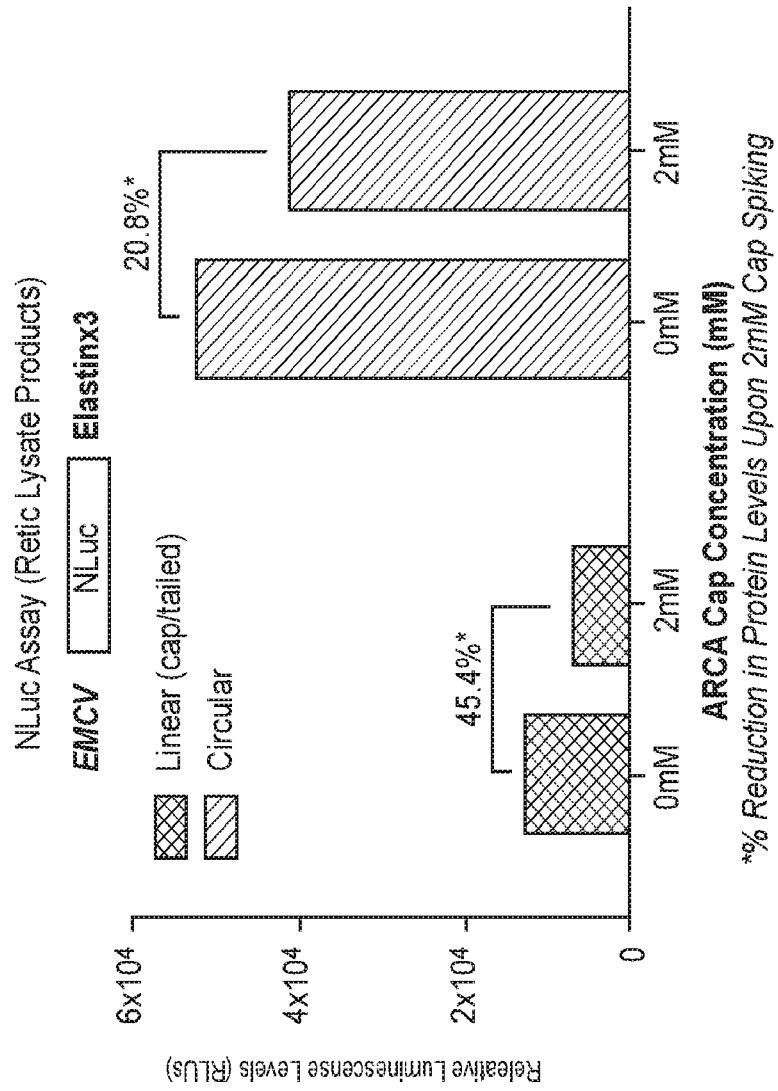
FIG. 20 includes graphs showing that spiking with a competitive cap analog confirms that translation of circularized RNA is cap-independent.
Figure 20:
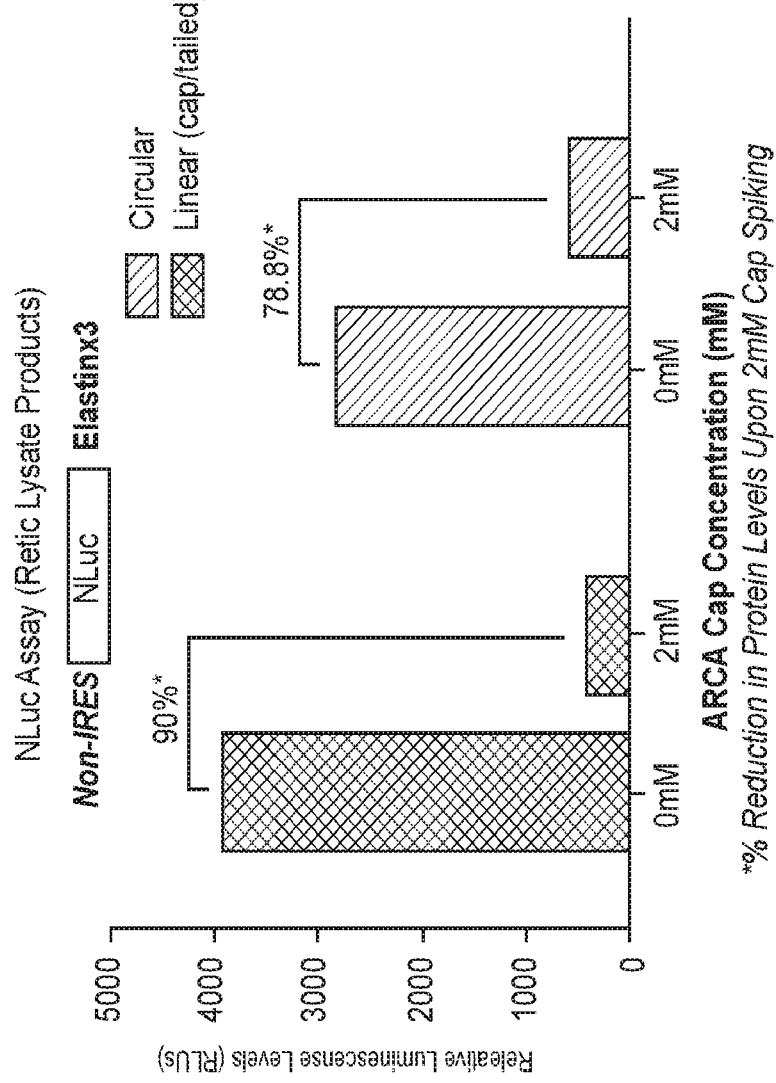
Figure 20:
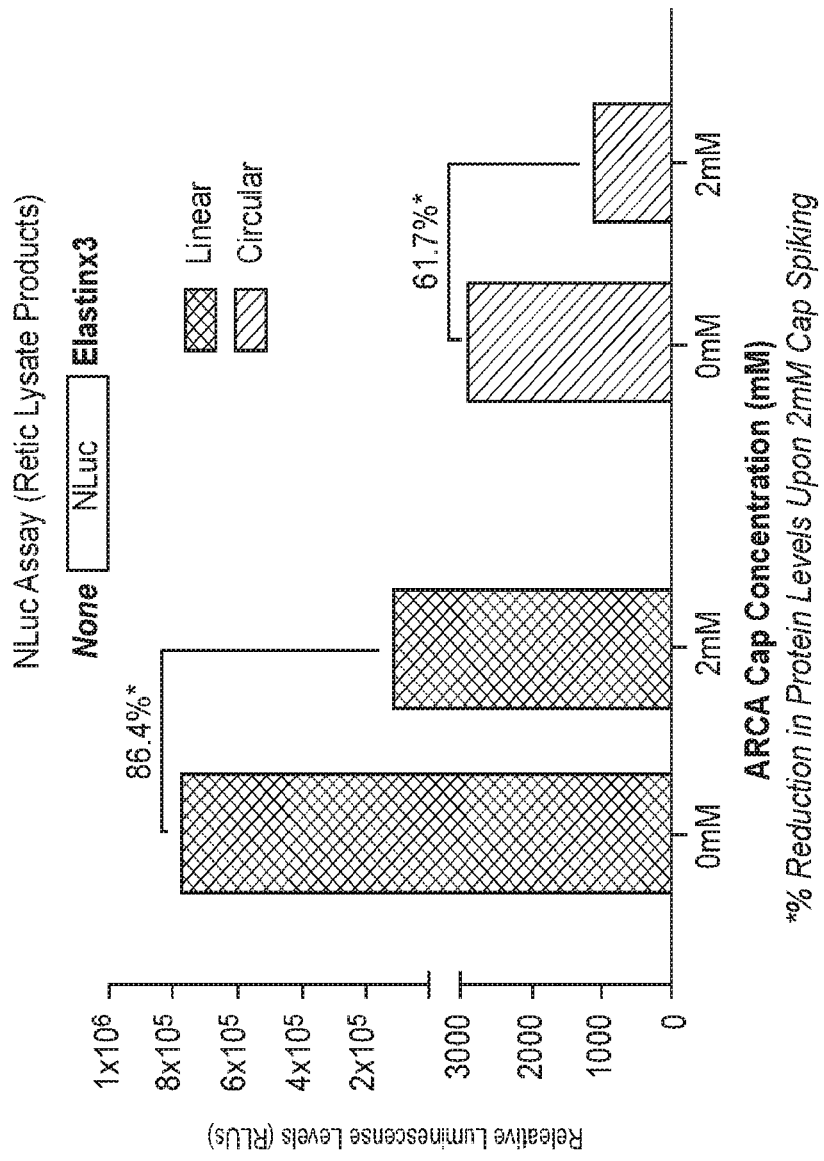

1.12 pmoles of linear or circularized NLuc RNA containing varying 5' UTR motifs (EMCV, Non-IRES, or No UTR) were used as templates in rabbit reticulocyte ("retic") lysate in vitro translation reactions. Prior to RNA addition, retic reactions were incubated for 15 minutes with 0 mM or 2 mM (final concentration) of ARCA cap analog at 30 degrees. Samples were incubated for another 75 minutes after addition of RNA. Reactions were transferred to a 96-well plate and assayed for NLuc expression by bioluminescence (FIG. 20). These data show that translation of linear RNA is compromised much more significantly than translation of circularized RNA (e.g., more than two-fold as much for EMCV-containing construct) upon addition of cap analog that competes for translation apparatus. That any inhibition is seen for the circularized RNA samples, which are expected to be translated in a cap-independent manner, suggests that 2 mM of cap analog is saturating and may induce conformational changes in eIF4E (and potentially eIF4G) that recruit other factors that are important to translation (e.g., eIF4A, eIF4B, and eIF3), thereby compromising their ability to find circularized RNA that is translationally competent even in the absence of the cap. Confirmatory experiments involving lower concentrations of cap analog may be performed using methods described herein.

Circularized RNA Containing the EMCV IRES is Translated More Efficiently than Canonical (Cap+Tailed) mRNA in a Cell-Free System.

Figure 21:
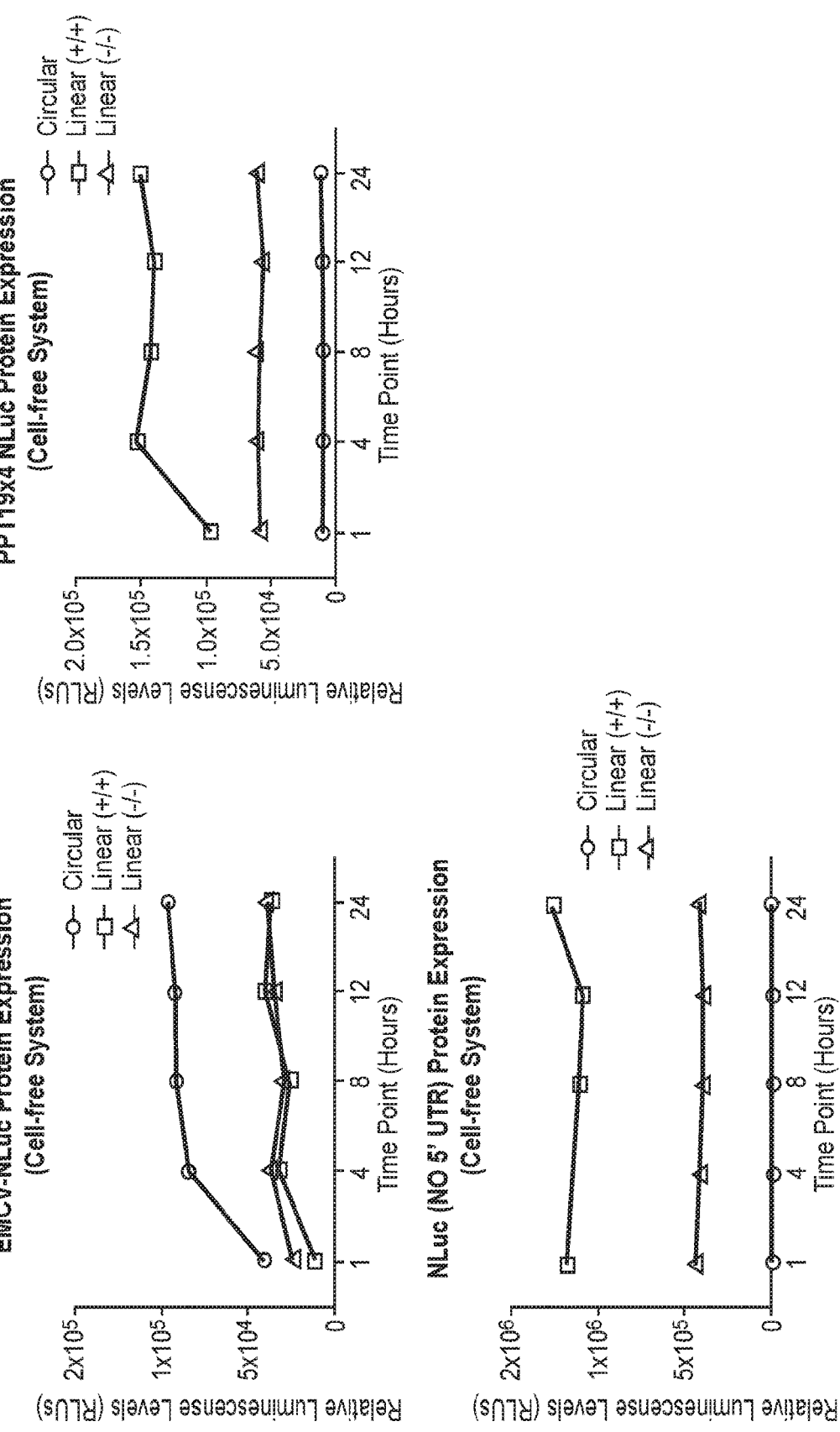
FIG. 21 includes graphs showing that, in a cell-free system, circularized RNA containing the EMCV IRES is translated more efficiently than canonical (capped/tailed) linear mRNA.

1.12 pmoles of linear or circularized NLuc RNA containing varying 5' UTR motifs (EMCV, PPT19x4, or No UTR) were used as templates in retic lysate in vitro translation reactions. At each indicated time point (over a 24 hour time course), a 15 µL aliquot was taken from each sample and assayed for NLuc expression by bioluminescence (FIG. 21). These data show that circularized RNA containing the EMCV IRES is translated more efficiently than canonical mRNA (e.g., comprising a 5' cap and polyA tail) in a cell-free in vitro lysate system. It is noteworthy that no protein is produced from circularized RNA if no UTR is incorporated.

Example 8: Characterizing Stability of Circularized RNA

Circularized RNA is More Resistant to Degradation than Canonical Linear RNA is.

Figure 22:
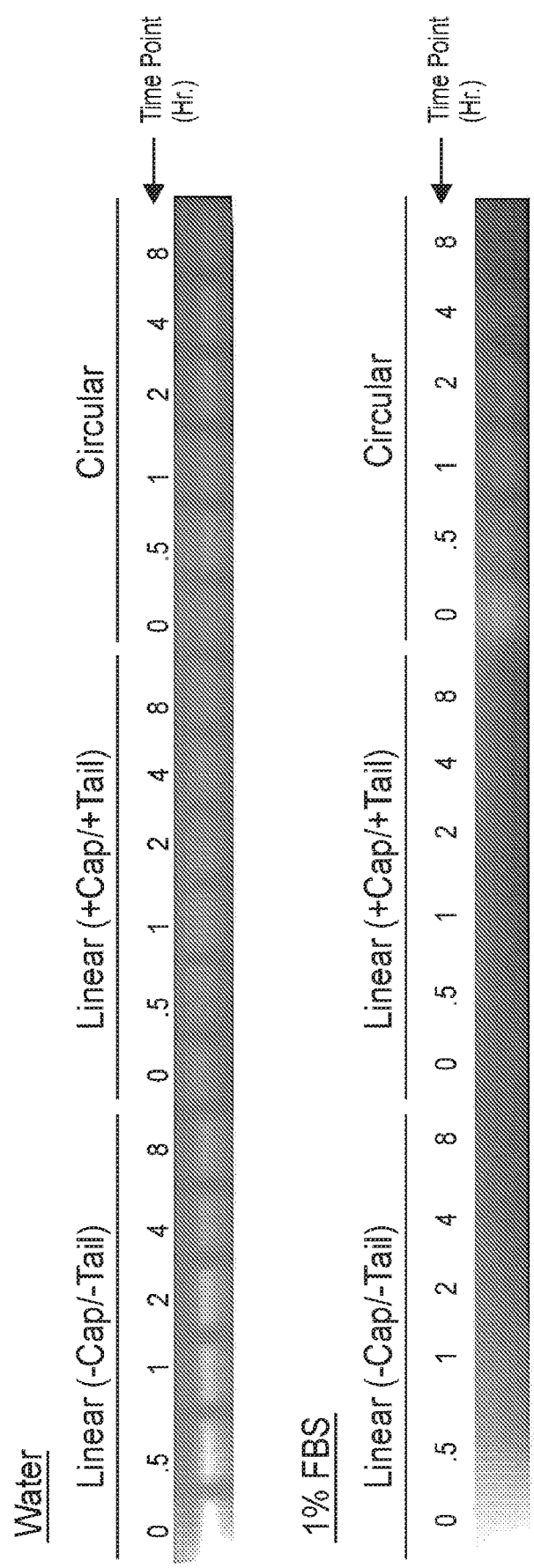
FIG. 22 includes gels showing that circularized RNA is more resistant to degradation than canonical linear RNA is.

Degradation Protection Assay was carried out using 750 ng of RNA encoding nanoluciferase in 3 forms: linear RNA without a 5' cap or PolyA tail (negative control), linear RNA with 5' cap and PolyA tail (canonical mRNA), and circularized RNA. Each sample was incubated in water or 1% FBS for 0, 0.5, 1, 2, 4, or 8 hours at room temperature. Afterwards, all samples were run on a 1% agarose gel for 35 minutes at 110 V (FIG. 22). These data show that, in solution, circularized RNA is more stable than linear RNA, including canonical mRNA.

Circularized RNA Encoding the Therapeutic Protein Preproinsulin is Sustained Longer In Vitro than Linear RNA is.

Figure 23:
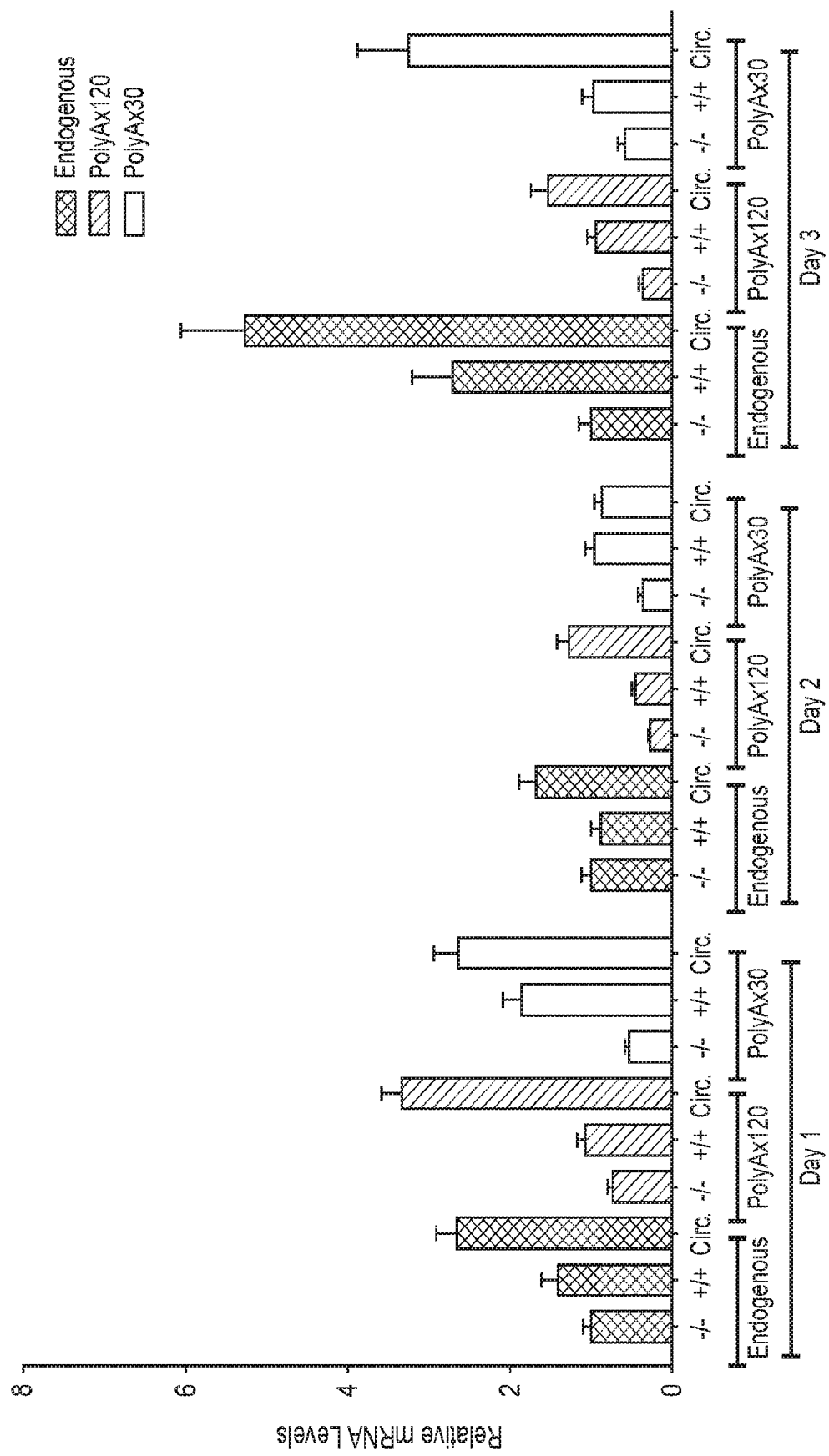
FIG. 23 includes a graph showing that, in vitro, circularized RNA encoding the therapeutic protein preproinsulin is sustained longer than linear RNA is. This finding is observed with multiple 5' UTRs.

Preproinsulin RNA was generated in 3 forms: linear RNA without a 5' cap or PolyA tail (−/−), linear canonical mRNA with 5' cap and PolyA tail (+/+), and circularized RNA (Circ.). Each form of RNA was generated with one of the following 5' UTRs: Endogenous preproinsulin UTR, PolyAx120, or Polyx30. All constructs contained a 3' UTR encoding a thrice-repeated 20-mer derived from the Elastin 3' UTR. Constructs were transfected into Hep3B cells and preproinsulin RNA levels were measured by qPCR 24, 48, and 72 hours post-transfection (FIG. 23). These data show that, in cells, circularized RNA encoding a therapeutic protein is more stable than linear RNA, including canonical mRNA.

Circularized RNA is More Stable than Linear RNA is In Vitro.

Figure 24:
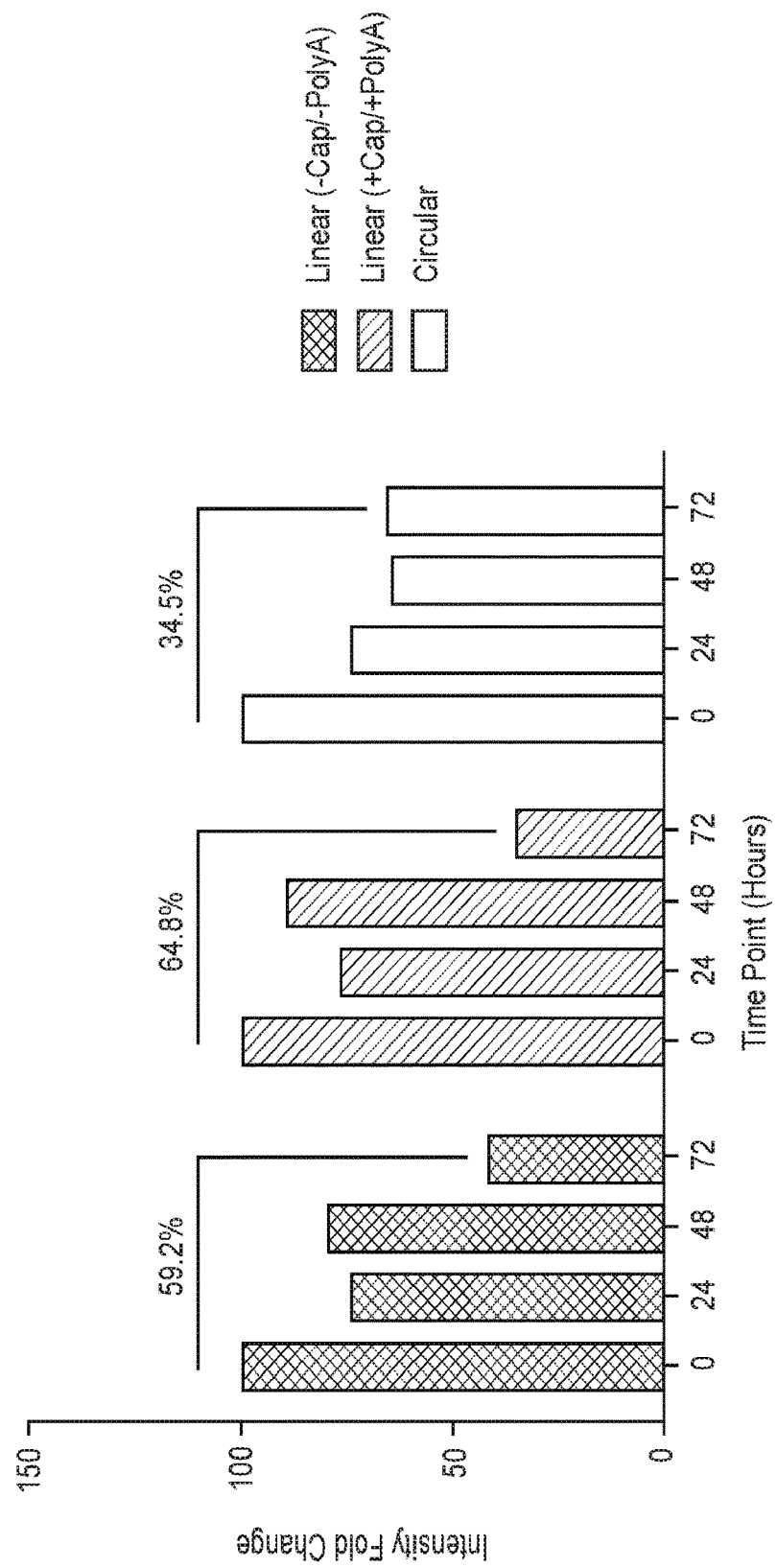
FIG. 24 includes a graph showing that, in vitro, circularized RNA is more stable than linear RNA is.

Degradation Protection Assay was carried out using 750 ng of RNA encoding nanoluciferase in 3 forms: linear RNA without a 5' cap or PolyA tail (negative control), linear RNA with 5' cap and PolyA tail (canonical mRNA), and circularized RNA. Each sample was incubated in water for 0, 24, 48, or 72 hours at room temperature. Afterwards, all samples were run on a 1% agarose gel for 35 minutes at 110 V. The data is summarized in FIG. 24. These data show that, in vitro, circularized RNA is more stable than linear RNA, including canonical mRNA.

Unlike Linear RNA, Circularized RNA Shows Minimal Loss Up to at Least 3 Days In Vivo, in Mouse Liver Following Intravenous Administration.

Figure 25:
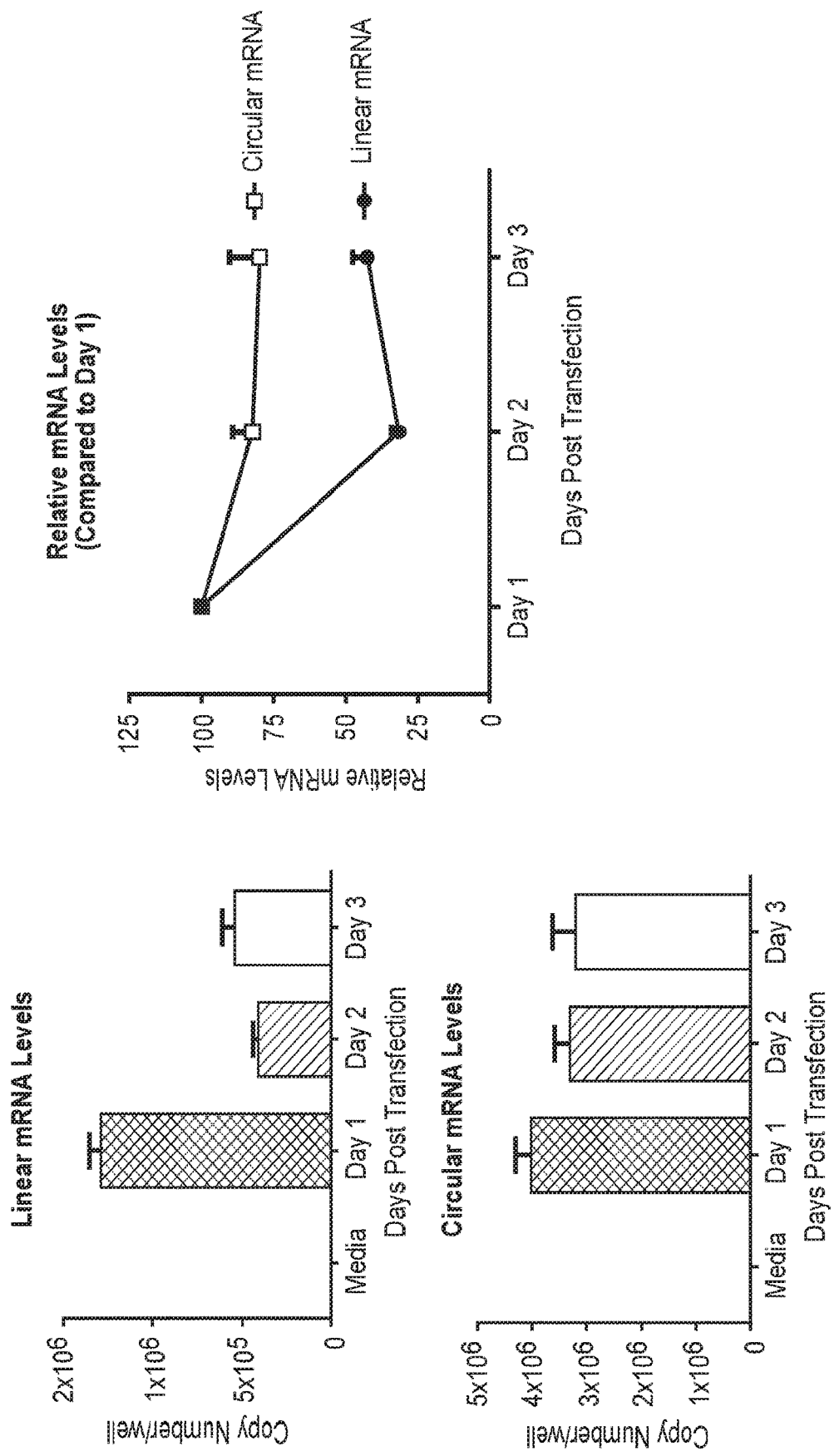
FIG. 25 includes graphs showing that, unlike linear RNA, circularized RNA shows minimal loss up to at least 3 days in mouse liver following intravenous administration.

20 µg of linear or circularized RNA was intravenously injected into Balb/c mice. Mice were sacrificed 24, 48, or 72 hours post injection. Livers were isolated, total RNA extracted from livers (PureLink® RNA Mini Kit, Invitrogen), cDNA synthesized (Superscript® IV, Invitrogen) and qPCR carried out to measure changes in RNA levels over the 3-day time course (FIG. 25; NLuc levels normalized to $\beta$-actin). For linear RNA there was an approximate 75% decrease in absolute RNA level from day 1 to day 2. In contrast, transfected circularized RNA constructs maintained a relatively stable absolute RNA level throughout the assay time points. Furthermore, data also indicate that Nluc relative RNA level of circularized constructs have approximately 4-fold greater expression than linear constructs after 1 and 2 days. On the third day, the circularized RNA has approximately 2-fold greater expression than linear RNA. These data show that, in vivo, circularized RNA is more stable than linear RNA, including canonical mRNA.

Example 9: Characterizing Translation Efficiency of Circularized RNA In Vivo

In Vivo, Protein Expression Derived from Circularized RNA is Sustained Longer than from Linear RNA.

Figure 26:
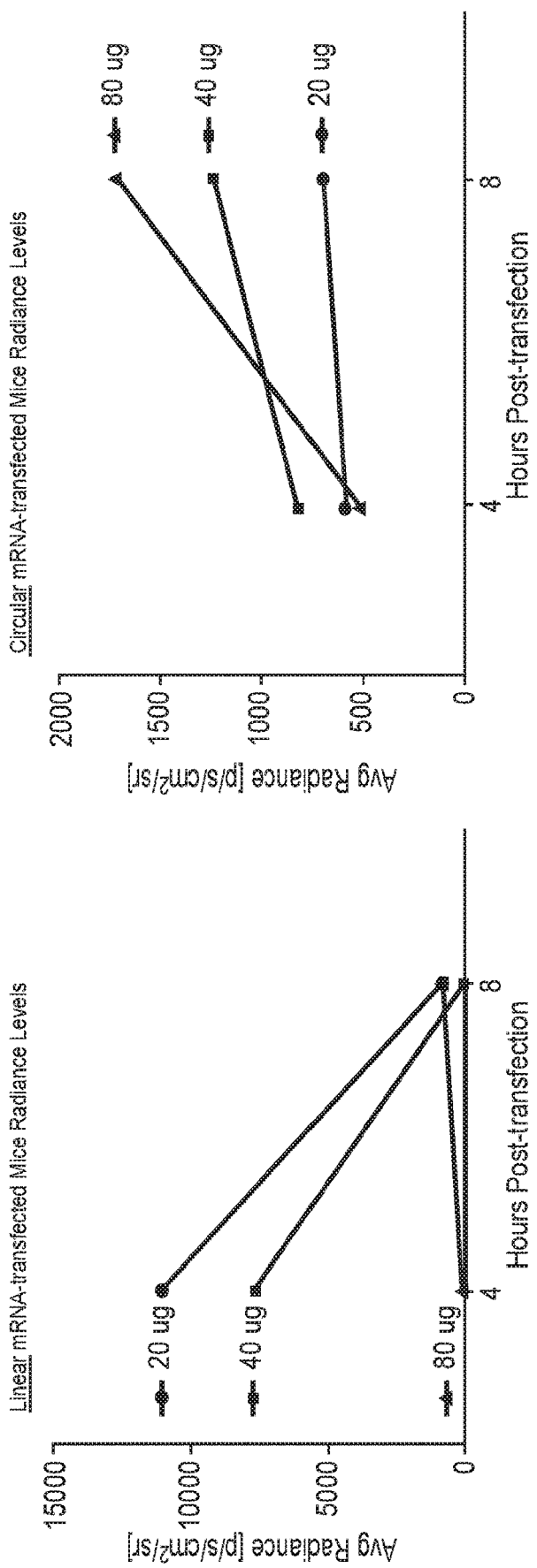
FIG. 26 includes graphs showing that, in vivo, protein expression derived from circularized RNA is sustained longer than from linear RNA.

20, 40 or 60 µg of linear or circularized RNA injected intravenously into Balb/c mice. Bioluminescence levels of live mice were measured at 4 and 8 hours post injection with a Xenogen Imager (FIG. 26). For this, in vivo assays used an in vivo imaging system (IVIS), in which nanoluciferase protein can be detected in live mice. One of the advantages of using the IVIS detection system is that it is not an endpoint analysis and thus, the same mouse can be monitored for nanoluciferase protein production over an extended period of time. For these assays, the mice were injected with furimazine, which reacts with Nanoluc luciferase, resulting in the emission of light. The data from these experiments indicate that ample amounts of Nanaoluc luciferase were detected in the abdominal space, rather than in the spleen, 4 hours post i.v. injection of the linear RNA constructs. In contrast, the circularized RNA construct expressed little Nanoluc luciferase at the same 4-hour time point. However, after 8 hours, the linear RNA treated mice appeared to have ceased Nanoluc luciferase expression; it also appeared that the linear RNA construct had degraded by the 8-hour time point as no signal was detected by IVIS. In contrast, circularized RNA treated mice seemed to have increased Nanoluc luciferase expression at the 8-hour time point (FIG. 26). These data show that, in vivo, protein production from circularized RNA is prolonged relative to linear RNA.

In Vivo, Circularized RNA is Resistant to Serum Nucleases.

Figure 27:
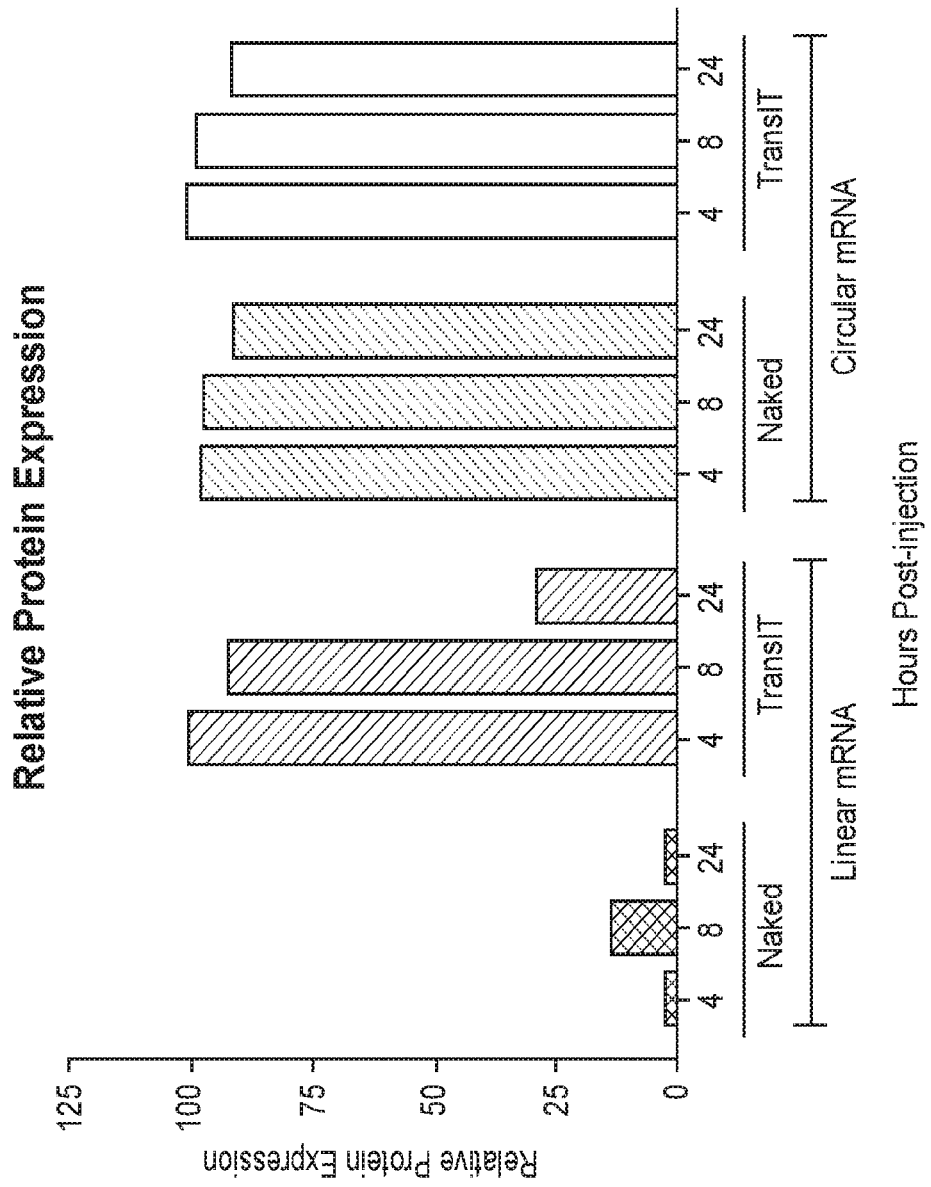
FIG. 27 includes a graph showing that, in vivo, circularized RNA is resistant to serum nucleases.

20 µg of circularized or linear RNA was injected into mice by hydrodynamic injection (1 mL in 5 seconds), either naked or complexed to the TransIT® transfection reagent (other transfection reagents, e.g., Invivofect®, TurboFect®, or RNAimax® can be used). NLuc protein expression was measured by in vivo imaging system (IVIS; Xenogen Imager), and average radiance levels were measured. Data show relative protein expression compared to the level observed 4 hours post-administration of RNA complexed to TransIT® (FIG. 27). Again, these data show that, in vivo, protein production from circularized RNA is prolonged relative to linear RNA.

It was found that RNA and protein levels were highest when TransIT® reagent was used. However, it was also noted that TransIT® can be toxic to mice, as half of the mice administered the TransIT® reagent died shortly after injection in one experiment. Optimal volumes of TransIT® reagent (i.e., volumes of the reagent that would not kill the mice, but yet allow for high RNA expression and protein function) were determined through a series of titration experiments. Four volumes of TransIT® were used in the titration experiments, 25 µL, 50 µL, 75 µL, and 100 µL. As a control for the titration experiments, untransfected animals as well as RNAimax®-transfected mice were used. Twenty-four hours following treatment, the mice were sacrificed and their livers were isolated and analyzed by qPCR for RNA level and for protein level (data not shown). These titration experiments indicated that mice had adverse reactions to volumes of 75 µL of TransIT® reagent. Based on the data obtained from these experiments, 50 µL of TransIT® was chosen for use, as this volume allows for clearly detectable RNA expression and protein function following transfection (data not shown) in the absence of acute toxicity to the mice.

Example 10: Circularized RNA Application in Cancer Vaccine Model

Peptide Presentation Continues to Increase Beyond Two Days if Circularized RNA is Transfected into Dendritic Cells (DCs).

Figure 28:
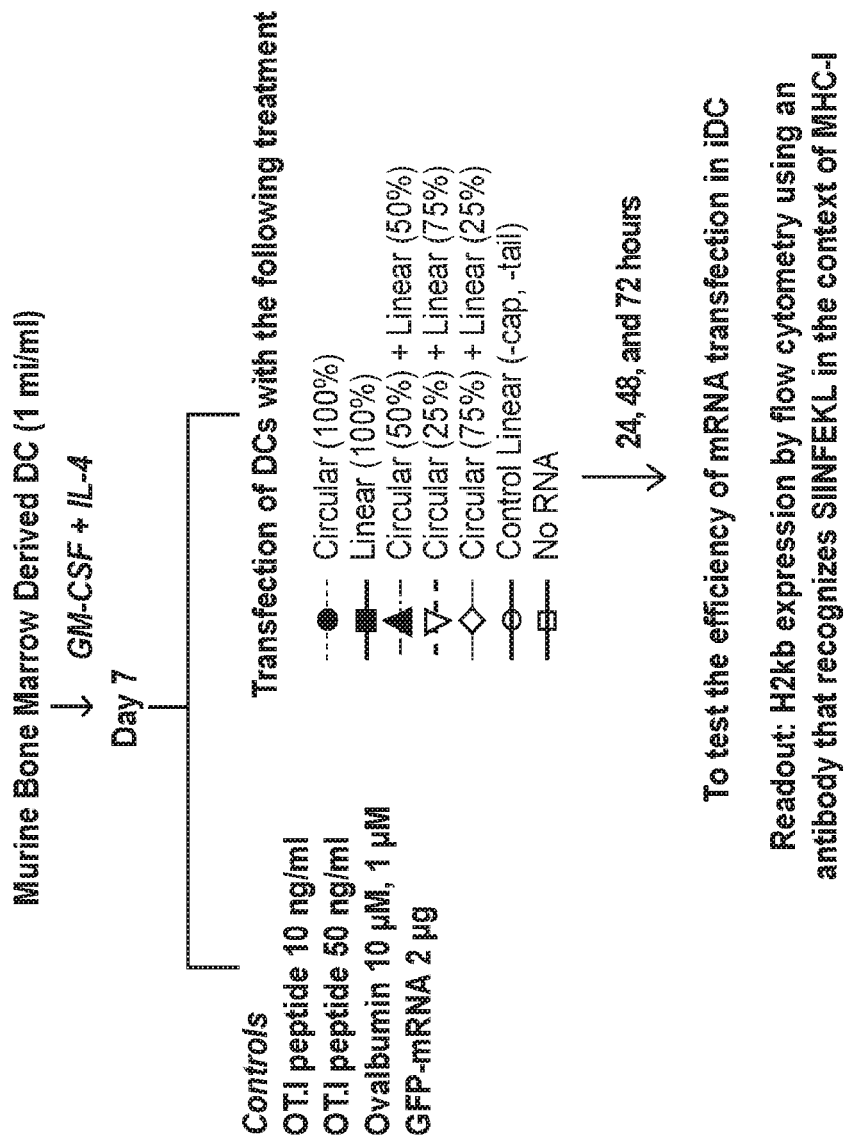
FIG. 28 includes a flow chart for experiments determining the kinetics of peptide presentation following transfection of dendritic cells (DCs) with circularized and/or linear RNA.
Figure 29:
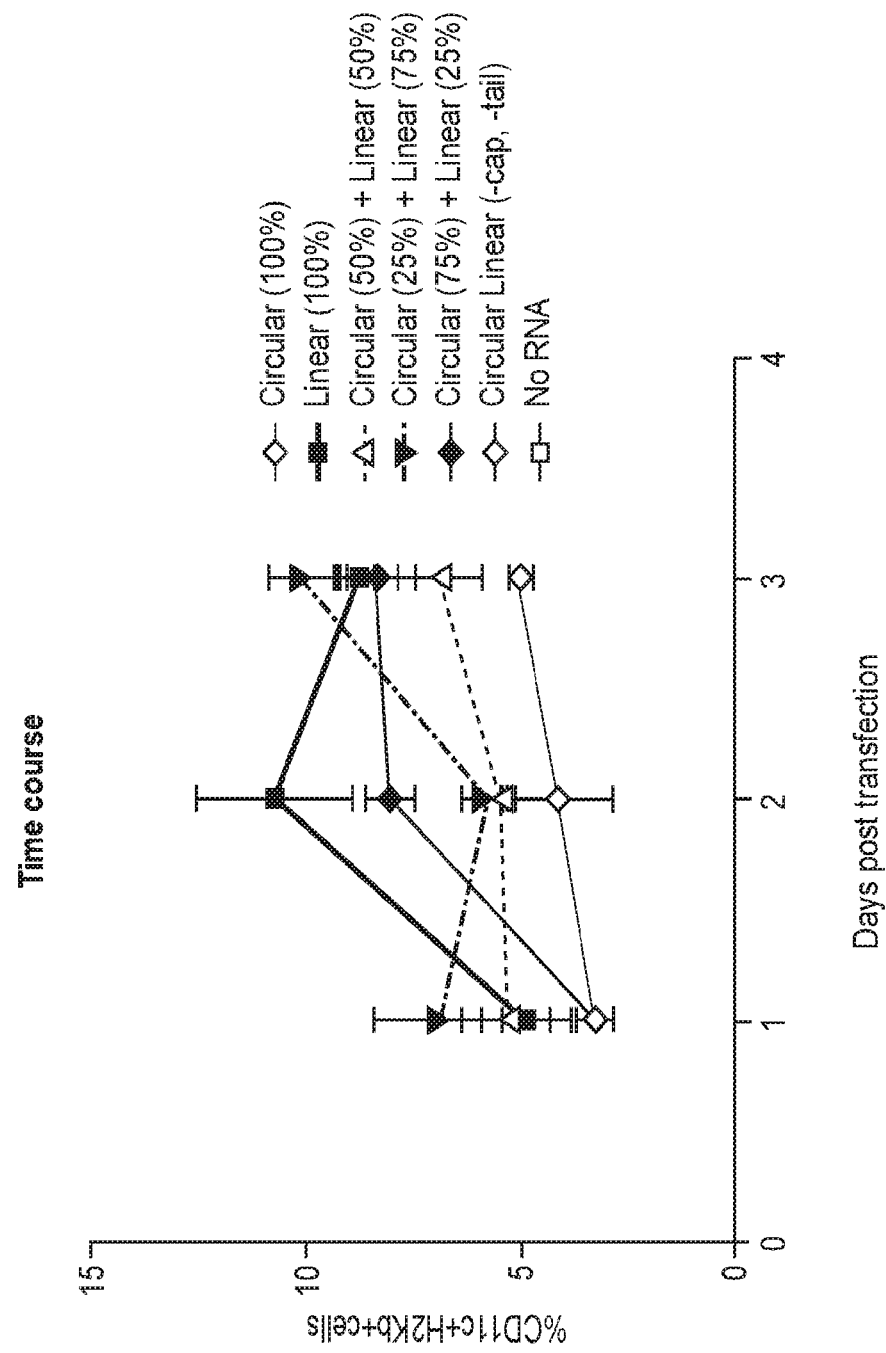
FIG. 29 includes a graph showing that, unlike for linear RNA, peptide presentation continues to increase beyond 2 days when circularized RNA is transfected into DCs.

FIG. 28 shows the steps and reagents used to generate data in FIG. 29, which shows kinetics of peptide presentation following transfection of DCs with circularized and/or linear RNA. These data show that addition of circularized RNA to linear RNA (each encoding antigen) for transfection of antigen presenting cells results in continued increase in antigen presentation through day three post-transfection, whereas the presentation begins to decrease in the linear RNA-only sample at this time point.

Addition of Circularized RNA to Linear RNA for Transfection of Antigen Presenting Cells Improves T Cell Priming.

Figure 30:
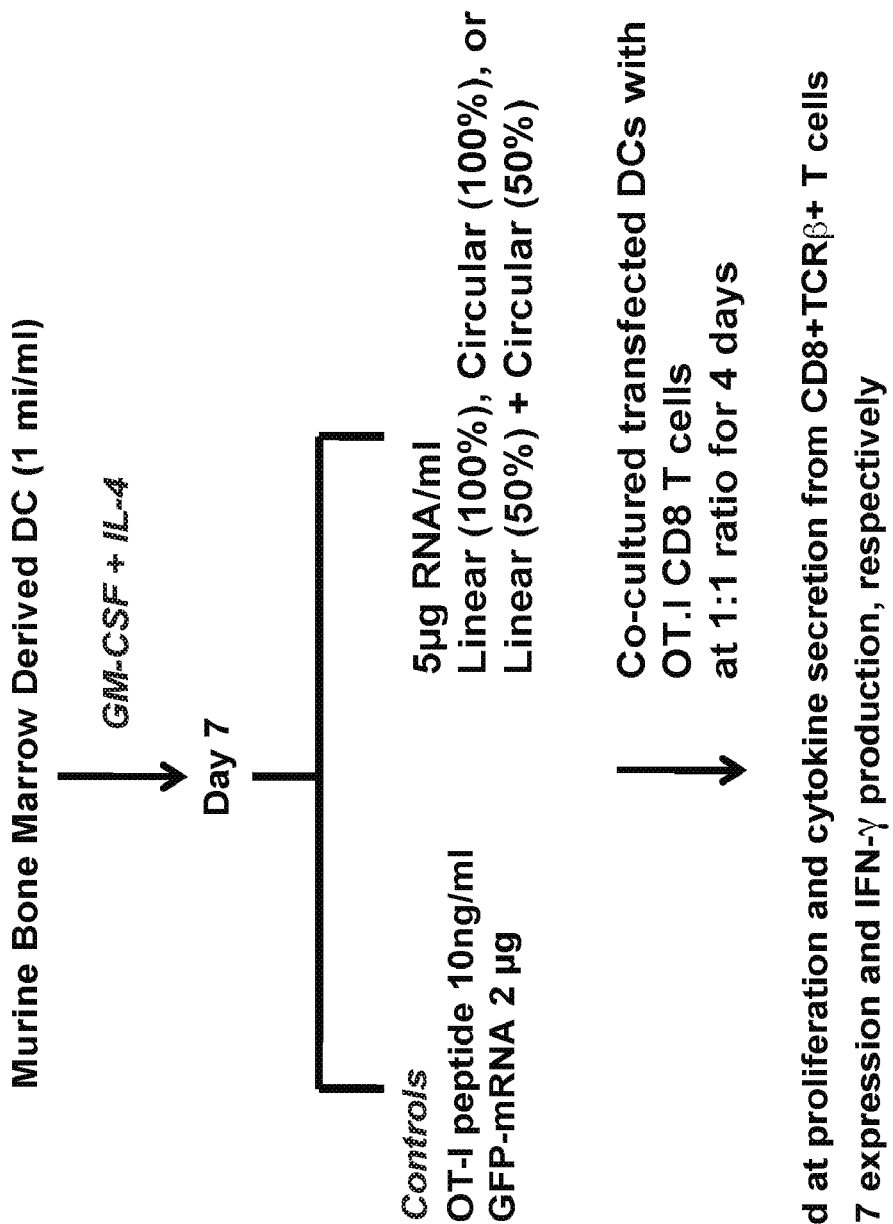
FIG. 30 includes a flow chart for experiments relating to the co-culture of OT.I CD8 T cells with RNA-transfected DCs.
Figure 31:
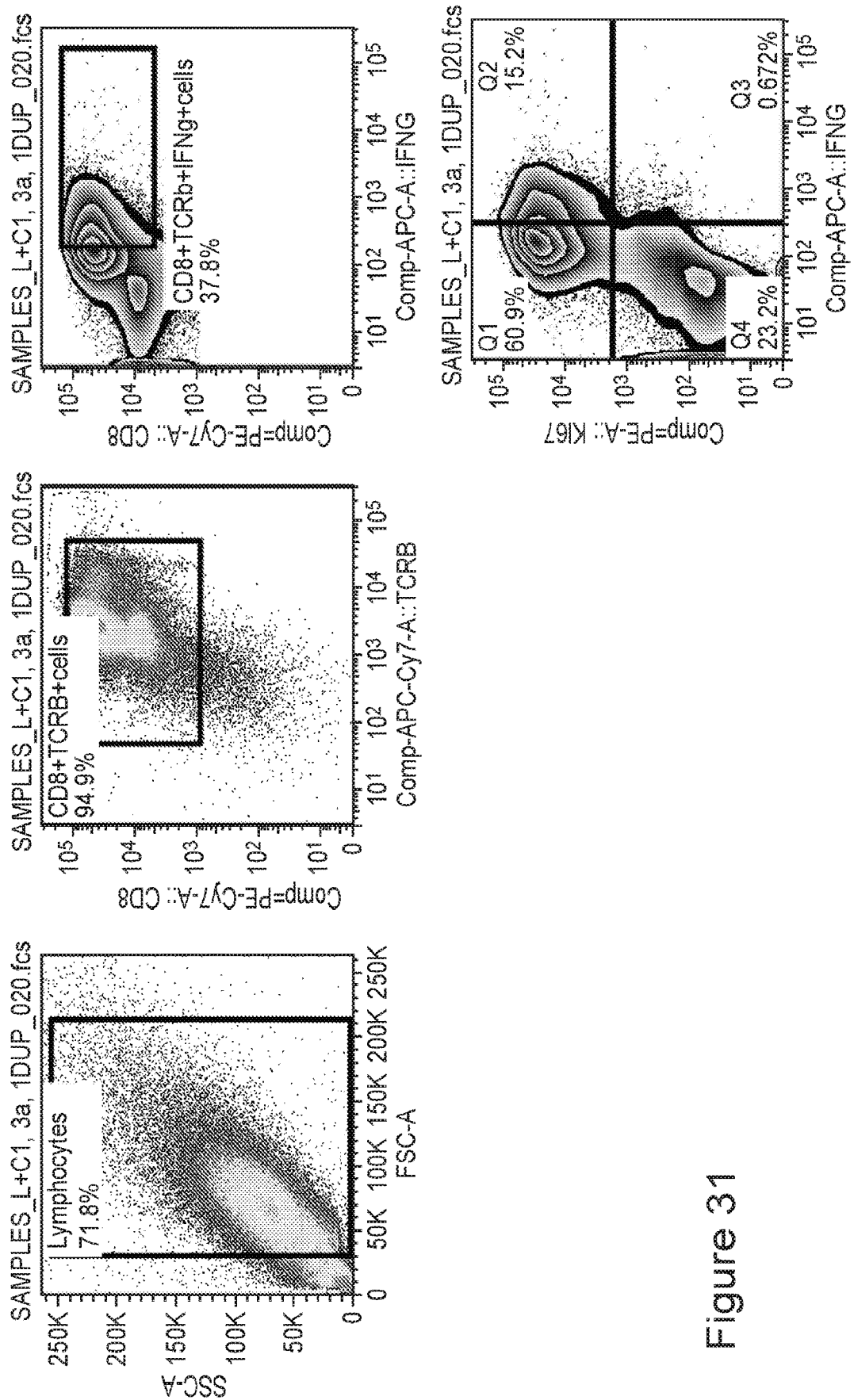
FIG. 31 includes flow cytometry plots showing a flow cytometry gating strategy after co-culture of OT.I CD8 T cells with RNA-transfected DCs.
Figure 32:
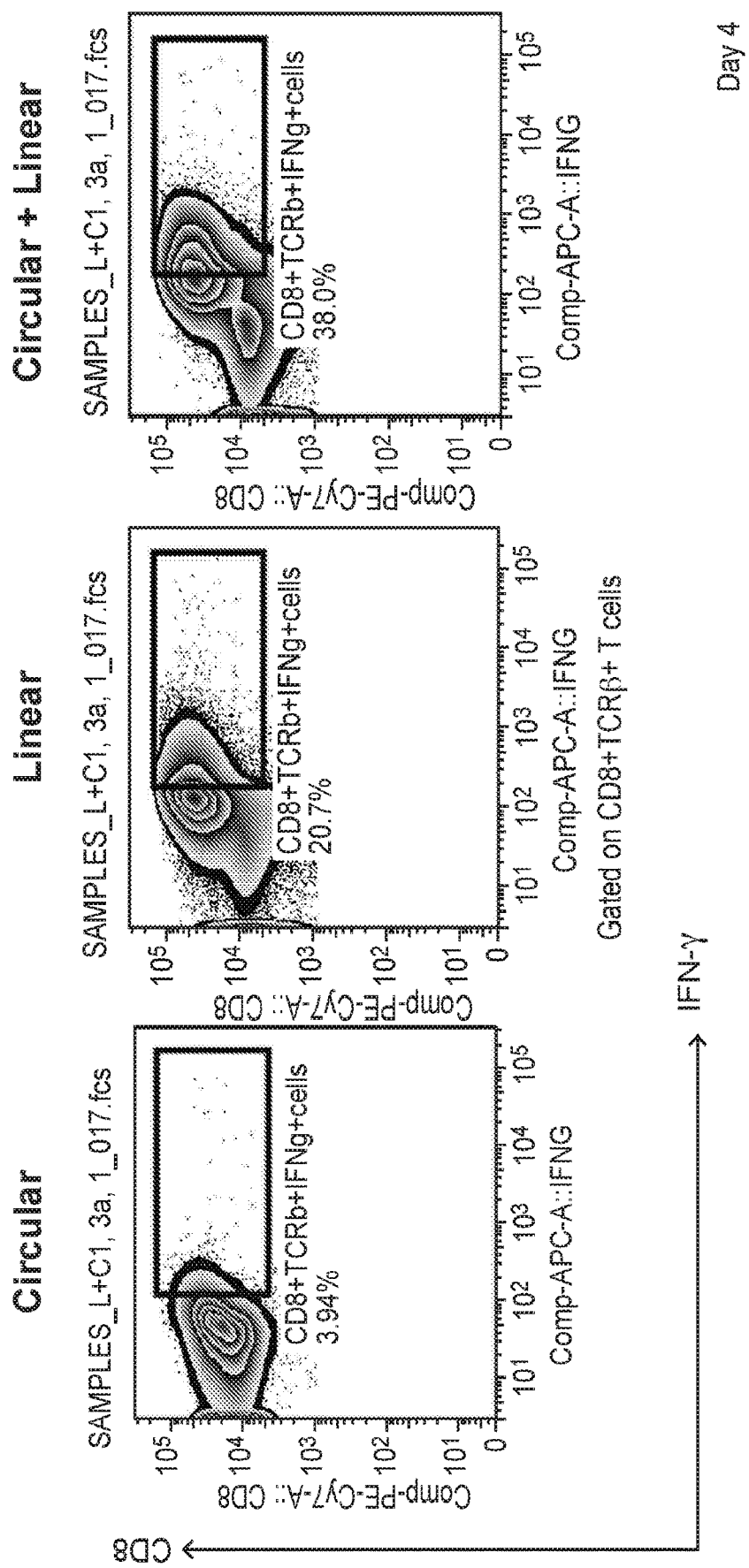
FIG. 32 includes flow cytometry plots showing that addition of circularized RNA to linear RNA improved T cell priming (function, as assessed by IFN-γ).
Figure 33:
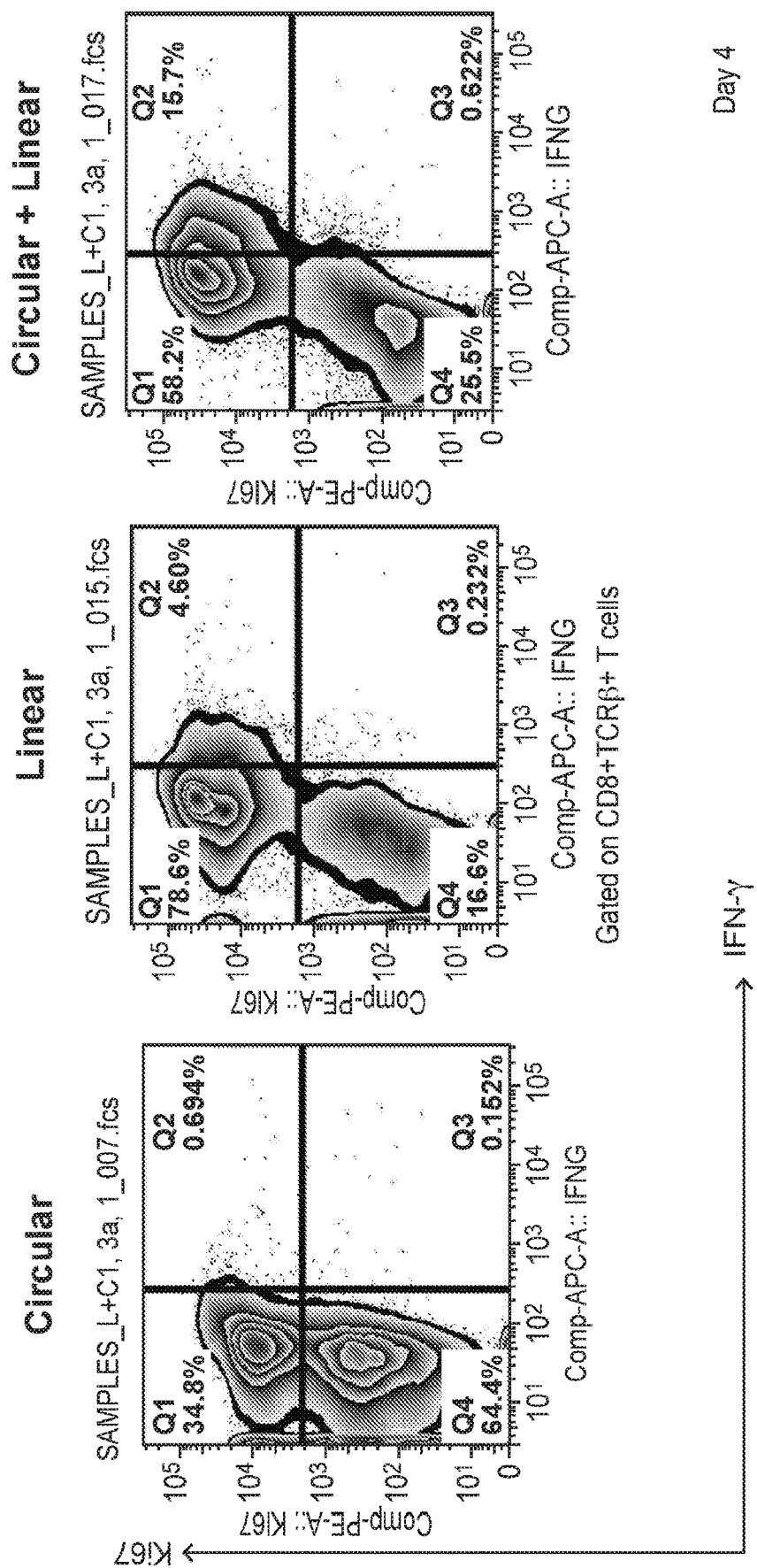
FIG. 33 includes flow cytometry plots showing that addition of circularized RNA to linear RNA improved T cell priming (function among proliferating cells, as assessed by Ki67/IFN-γ double-positive cells).

FIG. 30 shows the steps and reagents used for co-culturing of OT.I CD8 T cells with RNA-transfected DCs. FIG. 31 shows the flow cytometry gating strategy used after co-culture of OT.I CD8 T cells with RNA-transfected DCs. FIG. 32 shows that addition of circularized RNA to linear RNA improved T cell priming (function). Higher levels of IFN-γ are produced by antigen-specific $CD8^+TCR\beta^+$ T cells upon co-culture with DCs transfected by a combination of Circular+Linear RNA. FIG. 33 shows that addition of circularized RNA to linear RNA improved T cell priming (specifically among proliferating cells). Higher levels of IFN-γ are produced by proliferating antigen-specific $CD8^+$ $TCR\beta^+$ T cells upon co-culture with DCs transfected with the combination of Circular+Linear RNA. Together, these data show that addition of circularized RNA to linear RNA (each encoding antigen) for transfection of antigen presenting cells improves T cell priming, as evidenced by increased effector cytokine production, relative to transfection with either RNA alone.

Without being bound by theory, in the context of the combination of linear and circularized RNA, the linear RNA may act as a prime (based on a strong burst of expression), while the circularized RNA may act as a pseudo-boost (sustaining the presentation of antigen), thereby leading to improved effector T cell function.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A nucleic acid in the 5' to 3' direction comprising:
   a 5' motif comprising 5 to 50 random nucleotides;
   a 5' complement-reverse complement (CRC) sequence comprising 10 to 50 nucleotides;
   an RNA sequence of at least 300 nucleotides;
   a 3' CRC sequence comprising 10 to 50 nucleotides; and
   a 3' motif comprising 5 to 50 random nucleotides,
   wherein the 5' motif is not complementary to the 3' motif, and
   wherein the 5' CRC sequence is fully complementary to the 3' CRC sequence.

2. The nucleic acid of claim 1, wherein the RNA sequence is capable of being translated into a polypeptide.

3. The nucleic acid of claim 1, wherein the RNA sequence comprises a RNA that is a reverse complement of an endogenous RNA.

4. The nucleic acid of claim 3, wherein the endogenous RNA is an mRNA.

5. The nucleic acid of claim 1, wherein RNA sequence is capable of binding to an RNA-binding protein (RBP).

6. The nucleic acid of claim 1, wherein the 5' motif comprises 10, 15, or 20 random nucleotides and/or the 3' motif comprises 10, 15, or 20 random nucleotides.

7. The nucleic acid of claim 1, wherein the 5' motif and the 3' motif are partially complementary.

8. The nucleic acid of claim 1, wherein at least one of the 5' motif and the 3' motif comprises a polyA sequence.

9. The nucleic acid of claim 8, wherein the polyA sequence comprises 5 to 20 nucleotides.

10. The nucleic acid of claim 1, wherein the 5' CRC sequence comprises 10, 20, 30, or 40 nucleotides and/or the 3' CRC sequence comprises 10, 20, 30, or 40 nucleotides.

11. The nucleic acid of claim 10, wherein the 5' CRC sequence comprises 20 nucleotides and/or the 3' CRC sequence comprises 20 nucleotides.

12. The nucleic acid of claim 11, wherein the 5' CRC sequence comprises tggctgcacgaattgcacaa (SEQ ID NO: 1) and the 3' CRC sequence comprises ttgtgcaattcgtgcagcca (SEQ ID NO: 2).

13. The nucleic acid of claim 2, wherein the polypeptide encodes a therapeutic protein.

14. The nucleic acid of claim 13, wherein the therapeutic protein is preproinsulin, hypocretin, human growth hormone, leptin, oxytocin, vasopressin, factor VII, factor VIII, factor IX, erythropoietin, G-CSF, alpha-galactosidase A, iduronidase, N-acetylgalactosamine-4-sulfatase, FSH, DNase, tissue plasminogen activator, glucocerebrosidase, interferon, or IGF-1.

15. The nucleic acid of claim 1, wherein the nucleic acid comprises a modified nucleotide.

16. The nucleic acid of claim 15, wherein the modified nucleotide is a nucleotide analog selected from the group consisting of 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, 7-deazaadenosine, 6-azouridine, 6-azocytidine, 6-azothymidine, 5-methyl-2-thiouridine, 2-thiouridine, 4-thiouridine, 2-thiocytidine, dihydrouridine, pseudouridine, queuosine, archaeosine, naphthyl substituted naphthyl groups, an O- and N-alkylated purines and pyrimidines, N6-methyladenosine, 5-methylcarbonylmethyluridine, uridine 5-oxyacetic acid, pyridine-4-one, pyridine-2-one, aminophenol, 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

17. The nucleic acid of claim 16, wherein the modified nucleotide is 5-methylcytidine (5mC).

18. The nucleic acid of claim 1, wherein the nucleic acid's 5' and 3' termini are ligated such that the nucleic acid is circularized.

19. The nucleic acid of claim 18, wherein the circularized nucleic acid has greater stability relative to a non-circularized nucleic acid.

20. The nucleic acid of claim 19, wherein the greater stability is in vitro or in vivo.

21. The nucleic acid of claim 18, wherein the circularized nucleic acid provides greater polypeptide translation relative to a non-circularized nucleic acid.

22. The nucleic acid of claim 21, wherein the greater polypeptide translation is in vitro or in vivo.

23. An isolated cell comprising the nucleic acid of claim 18.

24. The nucleic acid of claim 1, further comprising at least one of a 5' UTR and a 3' UTR, wherein the 5' UTR is located between the 5' CRC sequence and the RNA sequence and the 3' UTR is located between the RNA sequence and the 3' CRC sequence.

25. The nucleic acid of claim 24, wherein the 5' UTR is polyAx30, polyAx120, PPT19, PPT19x4, GAAAx7, or polyAx30-EMCV.

26. The nucleic acid of claim 24, wherein the 3' UTR is HbB1-PolyAx10, HbB1, HbB1x2, or a motif from the Elastin 3' UTR.

27. The nucleic acid of claim 26, wherein the Elastin 3' UTR or a motif thereof is repeated twice or three times.

28. The nucleic acid of claim 25, wherein the 5' UTR is PPT19 or repeats thereof and the 3' UTR is derived from Elastin or a motif thereof and/or repeats thereof.

29. The nucleic acid of claim 24, wherein the 5' UTR comprises an internal ribosome entry site (IRES).

30. The nucleic acid of claim 29, wherein the IRES is an encephalomyocarditis virus (EMCV) IRES or a PPT19 IRES.

* * * * *